(12) United States Patent
Ibrahim et al.

(10) Patent No.: US 10,316,032 B2
(45) Date of Patent: Jun. 11, 2019

(54) SOLID FORMS OF A COMPOUND FOR MODULATING KINASES

(71) Applicant: Plexxikon Inc., Berkeley, CA (US)

(72) Inventors: Prabha N. Ibrahim, Mountain View, CA (US); Gary Conard Visor, Castro Valley, CA (US)

(73) Assignee: Plexxikon Inc., Berkeley, CA (US)

( * ) Notice: Subject to any disclaimer, the term of this patent is extended or adjusted under 35 U.S.C. 154(b) by 12 days.

(21) Appl. No.: 15/160,551

(22) Filed: May 20, 2016

(65) Prior Publication Data
US 2016/0340357 A1 Nov. 24, 2016

Related U.S. Application Data

(60) Provisional application No. 62/165,808, filed on May 22, 2015.

(51) Int. Cl.
*C07D 471/04* (2006.01)
*C07D 403/04* (2006.01)

(52) U.S. Cl.
CPC ......... *C07D 471/04* (2013.01); *C07D 403/04* (2013.01)

(58) Field of Classification Search
USPC ........................................................ 514/256
See application file for complete search history.

(56) References Cited

U.S. PATENT DOCUMENTS

| | | | |
|---|---|---|---|
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 2014/0128390 A1 | 5/2014 | Lin et al. |
| 2016/0326162 A1 | 11/2016 | Lin et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0349572 A1 | 12/2017 | Wu et al. |
| 2018/0030051 A1 | 2/2018 | Ibrahim et al. |
| 2018/0055828 A1 | 3/2018 | Bollag et al. |
| 2018/0072722 A1 | 3/2018 | Zhang et al. |
| 2018/0099939 A1 | 4/2018 | Zhang et al. |
| 2018/0099975 A1 | 4/2018 | Zhang et al. |

(Continued)

FOREIGN PATENT DOCUMENTS

WO  WO 2012/109075  *  8/2012
WO  WO-2012/109075 A1   8/2012

OTHER PUBLICATIONS

Norris (Experimental Organic Chemistry, McGraw-Hill 2nd Edition (1924)). (Year: 1924).*
U.S. Appl. No. 15/605,856, filed May 25, 2017, Ibrahim et al.
U.S. Appl. No. 15/606,682, filed May 26, 2017, Desai et al.
U.S. Appl. No. 15/620,396, filed Jun. 12, 2017, Wu et al.
U.S. Appl. No. 15/654,538, filed Jul. 19, 2017, Zhang et al.
U.S. Appl. No. 15/656,990, filed Jul., 21, 2017, Wu et al.
U.S. Appl. No. 15/665,804, filed Aug. 1, 2017, Ibrahim et al.
U.S. Appl. No. 15/669,353, filed Aug. 4, 2017, Bollag et al.

(Continued)

*Primary Examiner* — Marcos L Sznaidman
(74) *Attorney, Agent, or Firm* — Sheppard Mullin Richter & Hampton LLP

(57) ABSTRACT

Solid forms of Compound I (and its S-enantiomer, Compound II), active on protein kinases, were prepared and characterized:

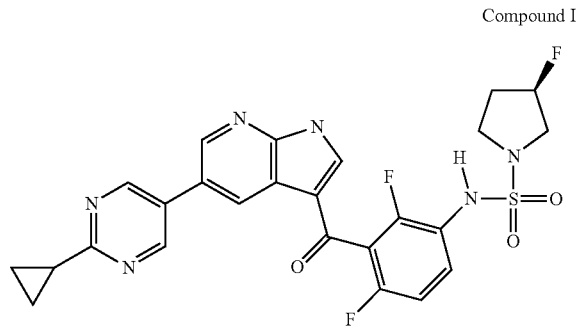

Also provided are methods of using the solid forms.

5 Claims, 25 Drawing Sheets

(56) References Cited

U.S. PATENT DOCUMENTS

| | | |
|---|---|---|
| 2018/0111929 A1 | 4/2018 | Ibrahim et al. |
| 2018/0111930 A1 | 4/2018 | Desai et al. |
| 2018/0215763 A1 | 8/2018 | Wu et al. |
| 2018/0265508 A1 | 9/2018 | Lin et al. |

OTHER PUBLICATIONS

U.S. Appl. No. 15/689,931, filed Aug. 29, 2017, Ibrahim et al.
U.S. Appl. No. 15/705,097, filed Sep. 14, 2017, Ibrahim et al.
U.S. Appl. No. 15/713,502, filed Sep. 22, 2017, Zhang et al.
U.S. Appl. No. 15725,197, filed Oct. 4, 2017, Ibrahim et al.
Invitation to pay additional fees and, where applicable, protest fee for International Application No. PCT/US2016/033586 dated Jul. 28, 2016.
Caira, "Crystalline Polymorphism of Organic Compounds", Topics in Current Chemistry, vol. 198, 1998, pp. 163-208.
Chhabra et al., "A review of drug isomerism and its significance", International Journal of Applied and Basic Medical Research, 2013, vol. 3, Issue 1.
Zhang et al., "RAF inhibitors that evade paradoxical MAPK pathway activation", 2015 Macmillan Publishers Limited, vol. 526, Nature.
International Search Report and Written Opinion for International Application No. PCT/US2016/033586 dated Sep. 28, 2016. (18 pages).
U.S. Appl. No. 15/851,639, filed Dec. 21, 2017, Wu et al.
U.S. Appl. No. 15/925,270, filed Mar. 19, 2018, Lin et al.
International Preliminary Report on Patentability for International Application No. PCT/US2016/033586 dated Nov. 28, 2017. (11 pages).
U.S. Appl. No. 15/977,772, filed May 11, 2018, Ibrahim et al.
U.S. Appl. No. 16/001,534, filed Jun. 6, 2018, Zhang et al.
U.S. Appl. No. 16/024,197, filed Jun. 29, 2018, Ibrahim et al.
U.S. Appl. No. 16/043,821, filed Jul. 24, 2018, Ibrahim et al.
U.S. Appl. No. 16/058,945, filed Aug. 8, 2018, Wu et al.
U.S. Appl. No. 16/109,199, filed Aug. 22, 2018, Wu et al.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/158,107, filed Oct. 11, 2018, Ibrahim et al.

\* cited by examiner

SOLID FORMS OF A COMPOUND FOR MODULATING KINASES

CROSS-REFERENCE TO RELATED APPLICATIONS

This application claims the benefit under 35 U.S.C. § 119(e) to U.S. Provisional Application Ser. No. 62/165,808, filed on May 22, 2015, which is hereby incorporated by reference in its entirety.

FIELD

The present disclosure relates generally to solid forms of Compounds I and II, named (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I), and (3S)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound II); processes for making the solid forms; and their therapeutic methods of use.

BACKGROUND

There remains a need to develop effective treatments for subjects suffering from or at risk of protein kinase mediated disease or condition. Suitable compounds, including Compound I, for the treatment of such diseases and conditions are disclosed in U.S. Pub. No. 2014/0128373, the disclosure of which is incorporated herein by reference in its entirety.

However, Compound I was not heretofore known in any of the specific crystalline forms A, B, D-M or O as described herein. Compound II, the S-enantiomer of Compound I, was not heretofore known in the specific crystalline form N.

SUMMARY

The present disclosure fulfills these needs and others by providing solid forms of Compound I and Compound II:

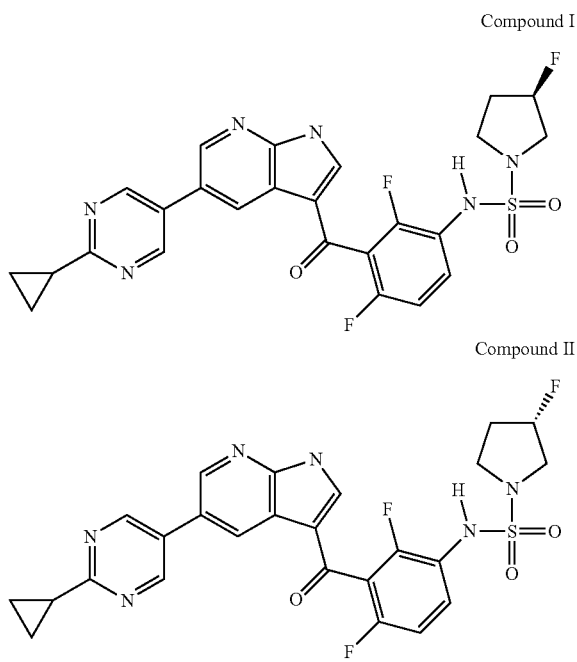

Compound I

Compound II

The present disclosure also provides pharmaceutical compositions comprising the solid forms of Compound I and Compound II. The disclosure also provides processes for making the solid forms and methods for using them in the treatment of Raf kinase mediated diseases or conditions.

Thus, one embodiment is directed to a solid form of Compound I. Another embodiment is directed to a polymorphic form of Compound I. Another embodiment is directed to a crystalline form of Compound I. In one embodiment, the crystalline form of Compound I is Compound I Form A. In another embodiment, the crystalline form of Compound I is Compound I Form B. In another embodiment, the crystalline form of Compound I is Compound I Form D. In another embodiment, the crystalline form of Compound I is Compound I Form E. In another embodiment, the crystalline form of Compound I is Compound I Form F. In another embodiment, the crystalline form of Compound I is Compound I Form G. In another embodiment, the crystalline form of Compound I is Compound I Form H. In another embodiment, the crystalline form of Compound I is Compound I Form I. In another embodiment, the crystalline form of Compound I is Compound I Form J. In another embodiment, the crystalline form of Compound I is Compound I Form K. In another embodiment, the crystalline form of Compound I is Compound I Form L. In another embodiment, the crystalline form of Compound I is Compound I Form M. In another embodiment, the crystalline form of Compound I is Compound I Form O.

Another embodiment is directed to a polymorphic form of Compound II. Another embodiment is directed to a crystalline form of Compound II. In one embodiment, the crystalline form of Compound II is Compound II Form N.

Thus, one embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form A). Compound I Form A is characterized by an X-ray powder diffractogram comprising the following peaks (±0.2°): at 13.0, 17.8, and 23.0, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form B). Compound I Form B is characterized by an X-ray powder diffractogram comprising the following peaks (±0.2°): at 10.4, 16.0, and 18.0 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form D). Compound I Form D is characterized by an X-ray powder diffractogram comprising the following peaks (±0.2°): at 9.0, 21.0, and 22.0 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form E). Compound I Form E is characterized by an X-ray powder diffractogram comprising the following peaks (±0.2°): at 7.2, 9.2, and 20.4 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form F). Compound I Form F is characterized by an X-ray powder diffractogram comprising the following peaks (±0.2°): at 15.1, 19.9, and 22.1 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form G). Compound I Form G is characterized by an X-ray powder diffractogram comprising the following peaks (±0.2°): at 14.8, 15.1, and 21.5 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form H). Compound I Form H is characterized by an X-ray powder diffractogram comprising the following peaks (±0.2°): at 8.5, 17.0, and 23.7 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form I). Compound I Form I is characterized by an X-ray powder diffractogram comprising the following peaks (±0.2°): at 7.2, 9.3, and 20.6 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form J). Compound I Form J is characterized by an X-ray powder diffractogram comprising the following peaks (±0.2°): at 14.9, 20.1, and 21.6 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form K). Compound I Form K is characterized by an X-ray powder diffractogram comprising the following peaks (±0.2°): at 16.0, 18.0, and 20.3 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form L). Compound I Form L is characterized by an X-ray powder diffractogram comprising the following peaks (±0.2°): at 13.2, 17.7, and 23.2 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form M). Compound I Form M is characterized by an X-ray powder diffractogram comprising the following peaks (±0.2°): at 7.5, 15.6, and 23.2 °2θ, as determined on a diffractometer using Cu—Kα radiation.

Another embodiment is directed to crystalline (3S)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound II Form N). Compound II Form N is characterized by an X-ray powder diffractogram comprising the following peaks (±0.2°): at 13.4, 17.6 and 23.4 °2θ, as determined on a diffractometer using Cu—Kα radiation.

Another embodiment is directed to crystalline (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I Form O). Compound I Form O is characterized by an X-ray powder diffractogram comprising the following peaks (±0.2°): at 4.8, 17.1, and 17.7 °2θ, as determined on a diffractometer using Cu—Kα radiation.

One embodiment is a pharmaceutical composition comprising a compound selected from the group consisting of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N, and Compound I Form O, and a pharmaceutically acceptable excipient.

Another embodiment is a pharmaceutical composition comprising a compound selected from Compound I Form B, Compound I Form H or Compound II Form N, and a pharmaceutically acceptable excipient.

Another embodiment is directed to a method for treating a subject suffering from or at risk of a disease or condition mediated by a protein kinase comprising administering to the subject a therapeutically effective amount of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound I Form O or Compound II Form N.

Another embodiment is directed to a method for treating a subject suffering from or at risk of a disease or condition mediated by a protein kinase comprising administering to the subject a therapeutically effective amount of Compound I Form B, Compound I Form H or Compound II Form N.

Another embodiment is directed to a method for treating a subject suffering from or at risk of a disease or condition mediated by B-Raf or any mutations thereof, comprising administering to the subject a composition comprising a therapeutically effective amount of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M or Compound I Form O, and a pharmaceutically acceptable excipient.

Another embodiment is directed to a method for treating a subject suffering from or at risk of a disease or condition mediated by B-Raf or any mutations thereof, comprising administering to the subject a composition comprising a therapeutically effective amount of Compound I Form B, Compound I Form H or Compound II Form N, and a pharmaceutically acceptable excipient.

Still an additional embodiment includes, optionally in combination with any other embodiment described herein, the use of any one of Compound I Forms as described herein in the manufacture of a medicament for treating subjects suffering from or at risk of a disease or condition mediated by protein kinases.

Another embodiment is directed to a composition comprising two or more compounds selected from the group consisting of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M and Compound I Form O.

Another embodiment is directed to a composition comprising Compound I Form B or Compound I Form H or Compound II Form N. In one embodiment, the composition comprises at least about 50% w/w, at least about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound I Form B. In another embodiment, the composition comprises at least about 50% w/w, at least about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound I Form H. In another embodiment, the composition comprises at least about 50% w/w, at least about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound II Form N.

DETAILED DESCRIPTION

Figure 1:
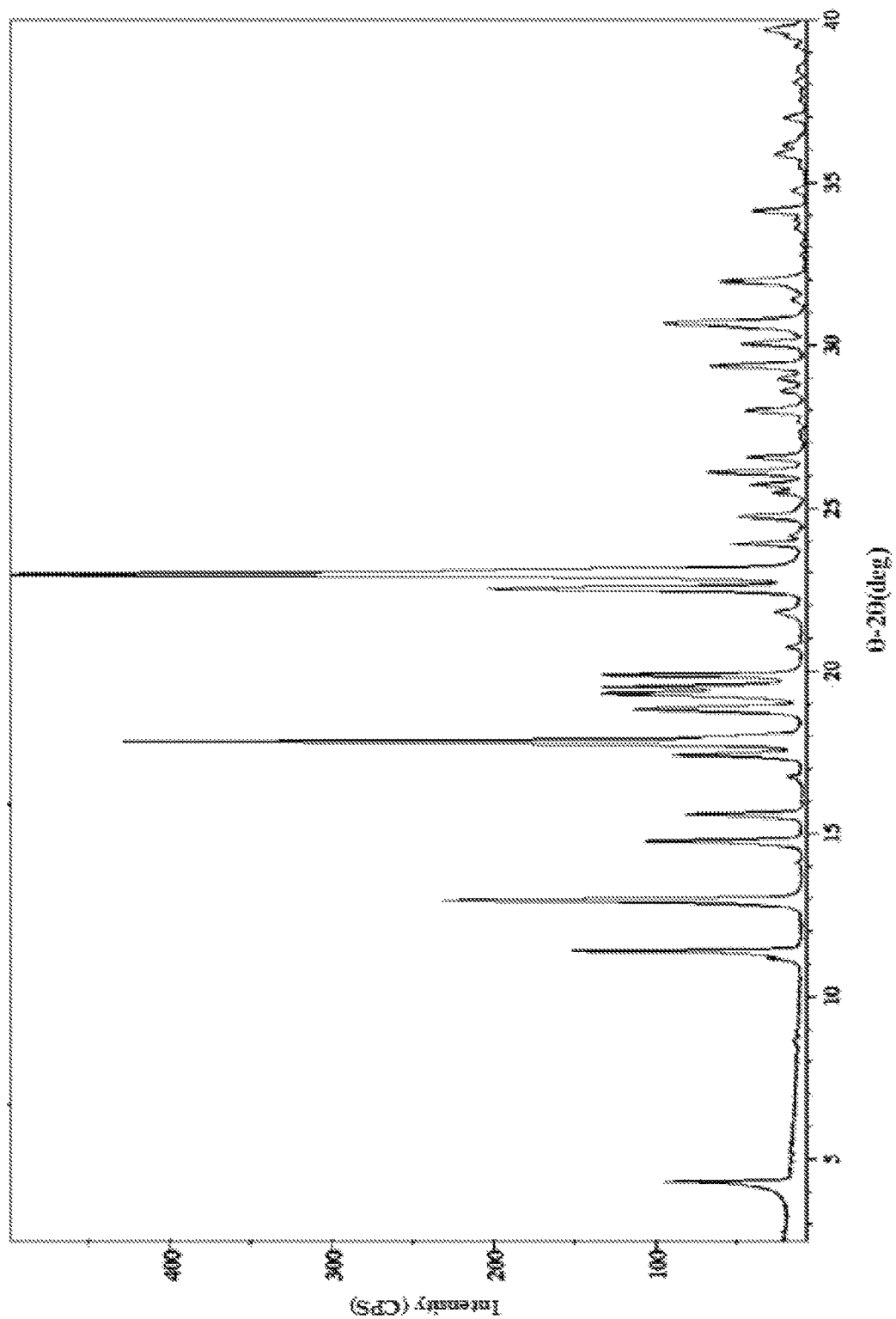
FIG. 1 is an X-ray powder diffraction pattern of Compound I Form A.

The compound named (3R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound I), is useful in treatments for subjects suffering from or at risk of protein kinase mediated disease or condition and has the following structure:

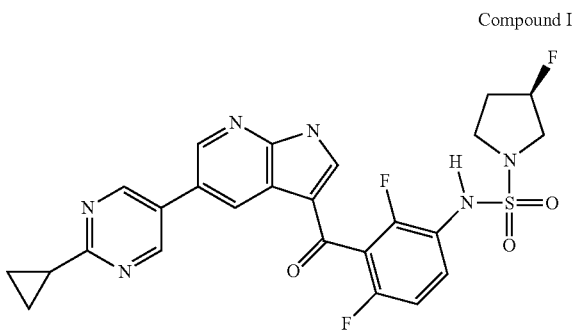 [SMILES: O=C(c1c(F)ccc(NS(=O)(=O)N2CC[C@@H](F)C2)c1F)c1c[nH]c2ncc(-c3cnc(C4CC4)nc3)cc12]

Compound I

The present disclosure relates to solid forms of Compounds I. The present disclosure also relates to polymorphic forms of Compound I. The present disclosure also relates to various crystalline forms of Compound I and processes for making the crystalline forms. The crystalline forms of Compound I are described herein as "Compound I Form A," "Compound I Form B," "Compound I Form D," "Compound I Form E," "Compound I Form F," "Compound I Form G," "Compound I Form H," "Compound I Form I," "Compound I Form J," "Compound I Form K," "Compound I Form L," "Compound I Form M" and "Compound I Form O." In some embodiments, such forms of Compound I may be a solvate.

The compound named (3S)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide (Compound II), is the S-enantiomer of Compound I and has the following structure:

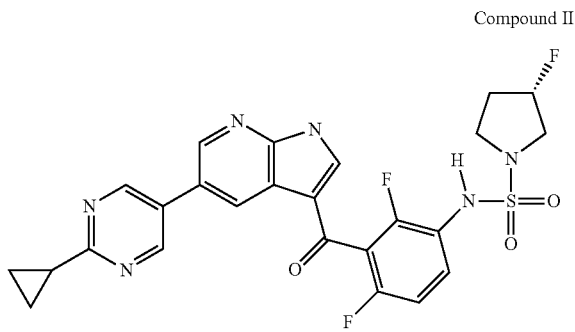 [SMILES: O=C(c1c(F)ccc(NS(=O)(=O)N2CC[C@H](F)C2)c1F)c1c[nH]c2ncc(-c3cnc(C4CC4)nc3)cc12]

Compound II

The present disclosure relates to a solid form of Compounds II. The present disclosure also relates to a polymorphic form of Compound II. The present disclosure also relates to a crystalline form of Compound II. The crystalline form of Compound II is described herein as "Compound II Form N."

Definitions

As used herein the following definitions apply unless clearly indicated otherwise.

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

Certain compounds contemplated for use in accordance with the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds contemplated for use in accordance with the present disclosure may exist in multiple crystalline or amorphous forms. In general, all physical forms are equivalent for the uses contemplated by the present disclosure and are intended to be within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

As used herein, the term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

As used herein, the terms "treat", "treating", "therapy", "therapies", and like terms refer to the administration of material, e.g., any one or more solid, crystalline or polymorphs of Compound I or Compound II as described herein in an amount effective to prevent, alleviate, or ameliorate one or more symptoms of a disease or condition, i.e., indication, and/or to prolong the survival of the subject being treated.

Compound I is an inhibitor of protein kinases. Compound I has $IC_{50}$ value of less than 0.1 µM for B-Raf V600E kinase targets.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

As used herein, the term "protein kinase mediated disease or condition," refers to a disease or condition in which the biological function of a protein kinase, including any mutations thereof, affects the development, course, and/or symptoms of the disease or condition, and/or in which modulation of the protein kinase alters the development, course, and/or symptoms of the disease or condition. The protein kinase mediated disease or condition includes a disease or condition for which inhibition provides a therapeutic benefit, e.g. wherein treatment with protein kinase inhibitor(s), including one or more solid, crystalline or polymorphs of Compound I or as described herein, provides a therapeutic benefit to the subject suffering from or at risk of the disease or condition.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

As used herein, the phrase "substantially as shown in Figure" as applied to DSC thermograms is meant to include a variation of ±3° Celsius and as applied to thermogravimetric analysis (TGA) is meant to include a variation of ±2% in weight loss.

As used herein, the phrase "major peaks" in the XRPD pattern refers to a subset of the entire observed peak list. Major peaks are selected from observed peaks by identifying preferably non-overlapping, low-angle peaks, with strong intensity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| can | acetonitrile |
| DAG | diacylglycerol |
| DCE | dichloroethane |
| DCM | dichloromethane |
| DEA | diethylamine |
| DMAP | 4-dimethylaminopyridine |
| DMF | dimethylformamide |
| DMSO | dimethylsulfoxide |
| DSC | differential scanning calorimetry |
| EtOAc | ethyl acetate |
| EtOH | ethanol |
| HPLC | high pressure liquid chromatography |
| IPA | isopropanol |
| Kg | kilogram |
| MeOH | methanol |
| 2-MeTHF | 2-methyltetrahydrofuran |
| Mg | miligram |
| MTBE | methyl tert-butyl ether |
| N | normal |
| RH | relative humidity |
| RT | room temperature |
| t-BuOH | tert-butanol |
| TEA | triethylamine |
| TGA | thermogravimetric analysis |
| THF | tetrahydrofuran |
| μm | micrometer |
| μM | micromolar |
| V | volume |
| WFI | water for injection |
| XRPD | X-ray powder diffraction |

Compound I

Compound I was synthesized according to the synthetic scheme discussed below.

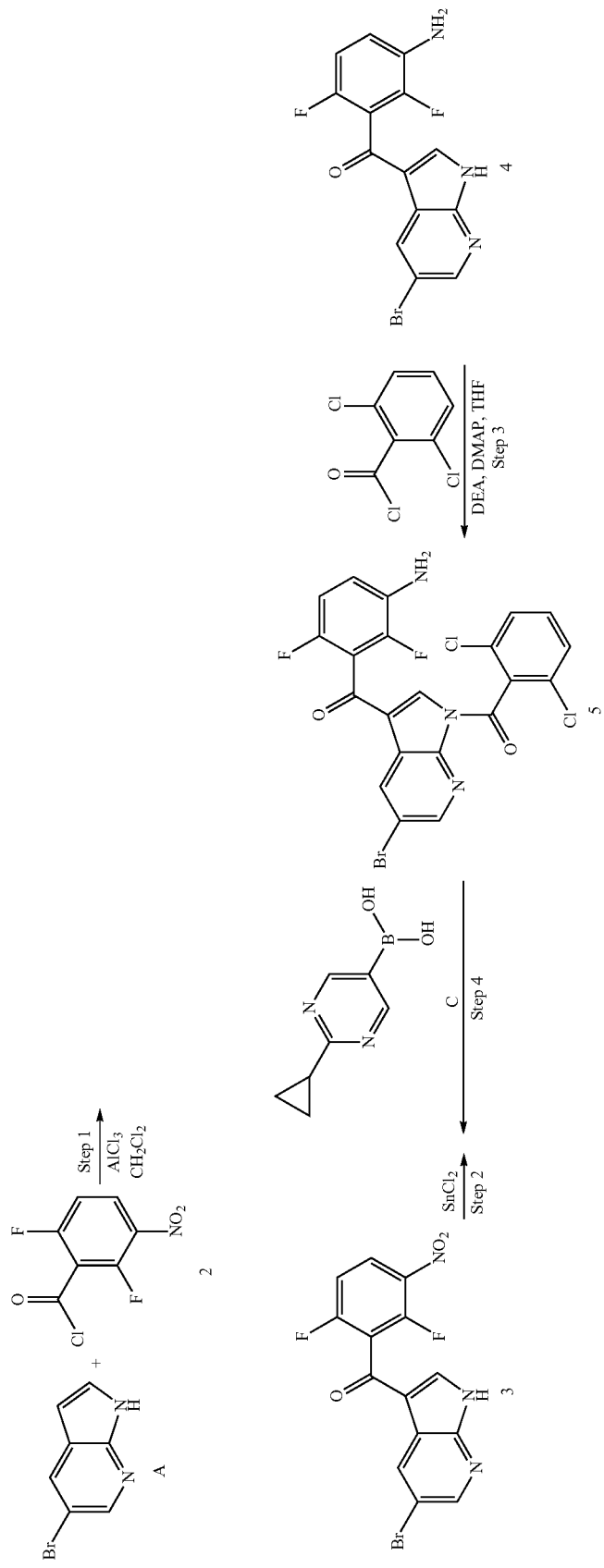

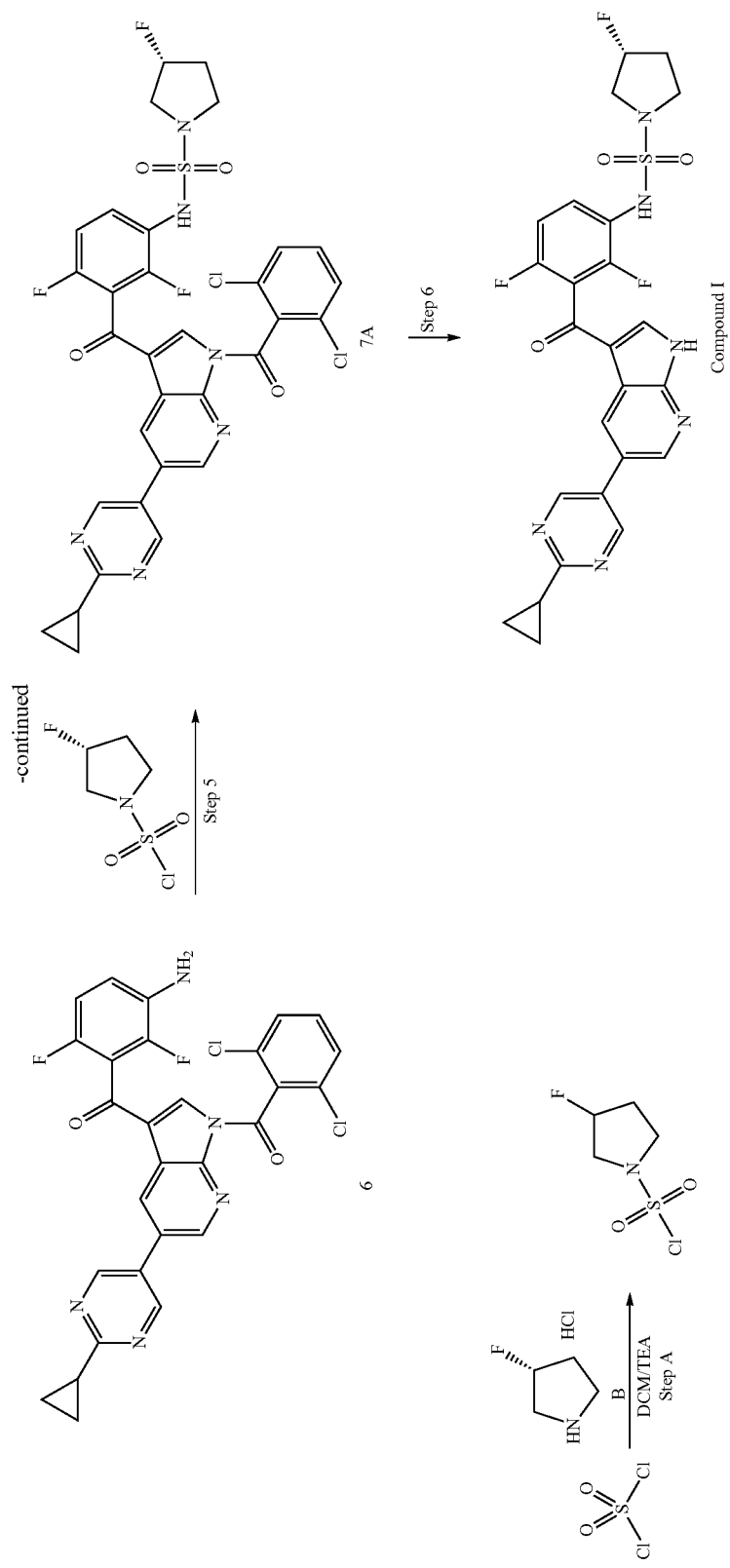

Similarly, Compound II was synthesized using the 3-S-fluropyrrolidine HCl salt in Step 5 of the scheme above.

Step 1

5-Bromo-7-azaindole (Compound A) was coupled with 2,6-difluoro-3-nitrobenzoyl chloride (Compound 2) in the presence of AlCl₃ to produce Compound 3. Dichloroethane was chosen as the solvent after lab experiments demonstrated that no reaction (or incomplete reaction) occurred in other solvents. The DCE mixture was charged to a stirring solution of ACN/water in order to isolate the product via filtration.

Step 2

Compound 3 was treated with SnCl₂ in 2-MeTHF which reduced the nitro group to an amine to give Compound 4. Mixture was worked up by treating with 3N NaOH (pH=13), washing with NaCl, and then with HCl to bring pH down to about 6. The solution was then carried into the next step.

Step 3

Compound 4 in 2-MeTHF was treated with 2,6-dichlorobenzoyl chloride in the presence of TEA/DMAP to make Compound 5 which was isolated from heptane as a yellow solid.

Step 4

Compound 5 and 2-cyclopropylprimidin-5-yl-5-boronic acid (Compound C) in 2-MeTHF were sparged with $N_2$ to which was added 8% NaHCO₃ (sparged) and Bis(triphenylphosphine)palladium(II) dichloride. The mixture was heated to reflux to give Compound 6 which was isolated from EtOAc as a brown solid.

Step A

3-R-fluropyrrolidine HCl salt was dissolved in dichloromethane and triethylamine. The solution was slowly charge to sulfuryl chloride over 4 hours at −25±5° C. then held for 15 hours. The TEA salts were filtered off and the filtrates were concentrated down to dryness in order to isolate the 3-R-fluropyrrolidine sulfonyl chloride (Compound B).

Step 5

Compound 6, dichloromethane, and pyridine were cooled to 10-15° C. then 3-R-fluropyrrolidine sulfonyl chloride (Compound B) was charged and heated to 90±5° C. Once the reaction was deemed complete by HPLC it was cooled to 25° C. and dichloromethane was added to obtain a solution. The compound 7A was then dried onto silica gel and purified via silica plug. Compound 7A was carried forward to an aqueous work up followed by a carbon treatment and isolated from methyl t-butyl ether and heptane.

Step 6

Compound 7A was dissolved in tetrahydrofuran and added 7N ammonia in methanol, once the reaction was deemed complete by HPLC there was a solvent exchanged with dichloromethane to isolate Compound I. Compound I was dissolved in tetrahydrofuran, filtered on the rotovaps for concentration and the isolated material was purified by recrystallization in 3v:1v ethyl acetate:2-propanol. The isolated Compound I was then triturated in WFI water.

Crystalline Forms of Compound I

As described generally above, the present disclosure provides crystalline forms of Compound I and Compound II which are disclosed herein.

Compound I Form A is characterized by an X-ray powder diffractogram comprising peaks (±0.2°) at 12.95, 17.83, and 22.95 °2θ, as determined on a diffractometer using Cu—Kα radiation. The diffractogram comprises additional peaks (±0.2°) at 4.31 and 22.51 °2θ. Form A is also characterized by its full X-ray powder diffractogram as substantially shown in FIG. 1. Major peaks in the XRPD pattern are shown in Table 1 below. In one embodiment, this disclosure provides Compound I Form A comprising two or more peaks (±0.2°) listed in the Table 1 below as determined on a diffractometer using Cu—Kα radiation.

TABLE 1

Major Peaks in the XRPD Pattern for Compound I Form A

| °2θ (±0.2°) | d-space [Å] |
|---|---|
| 4.31 | 20.499 ± 0.951 |
| 11.40 | 7.758 ± 0.136 |
| 12.95 | 6.830 ± 0.105 |
| 14.76 | 5.996 ± 0.081 |
| 15.58 | 5.683 ± 0.072 |
| 17.43 | 5.084 ± 0.058 |
| 17.83 | 4.972 ± 0.055 |
| 18.83 | 4.709 ± 0.050 |
| 19.29 | 4.597 ± 0.047 |
| 19.50 | 4.549 ± 0.046 |
| 19.87 | 4.465 ± 0.045 |
| 22.51 | 3.946 ± 0.035 |
| 22.95 | 3.872 ± 0.033 |

In another embodiment, this disclosure provides Compound I Form A comprising two or more peaks (±0.2°) listed in the Table 1A below as determined on a diffractometer using Cu—Kα radiation. Compound I Form A is characterized by an X-ray powder diffractogram comprising peaks (±0.2°) at 13.0, 17.8, and 23.0 °2θ, as determined on a diffractometer using Cu—Kα radiation. The diffractogram comprises additional peaks (±0.2°) at 4.3 and 22.5 °2θ.

TABLE 1A

Major Peaks in the XRPD Pattern for Compound I Form A

| °2θ (±0.2°) | d-space [Å] |
|---|---|
| 4.3 | 20.499 ± 0.951 |
| 11.4 | 7.758 ± 0.136 |
| 13.0 | 6.830 ± 0.105 |
| 14.8 | 5.996 ± 0.081 |
| 15.6 | 5.683 ± 0.072 |
| 17.4 | 5.084 ± 0.058 |
| 17.8 | 4.972 ± 0.055 |
| 18.8 | 4.709 ± 0.050 |
| 19.3 | 4.597 ± 0.047 |
| 19.5 | 4.549 ± 0.046 |
| 19.9 | 4.465 ± 0.045 |
| 22.5 | 3.946 ± 0.035 |
| 23.0 | 3.872 ± 0.033 |

Figure 2:
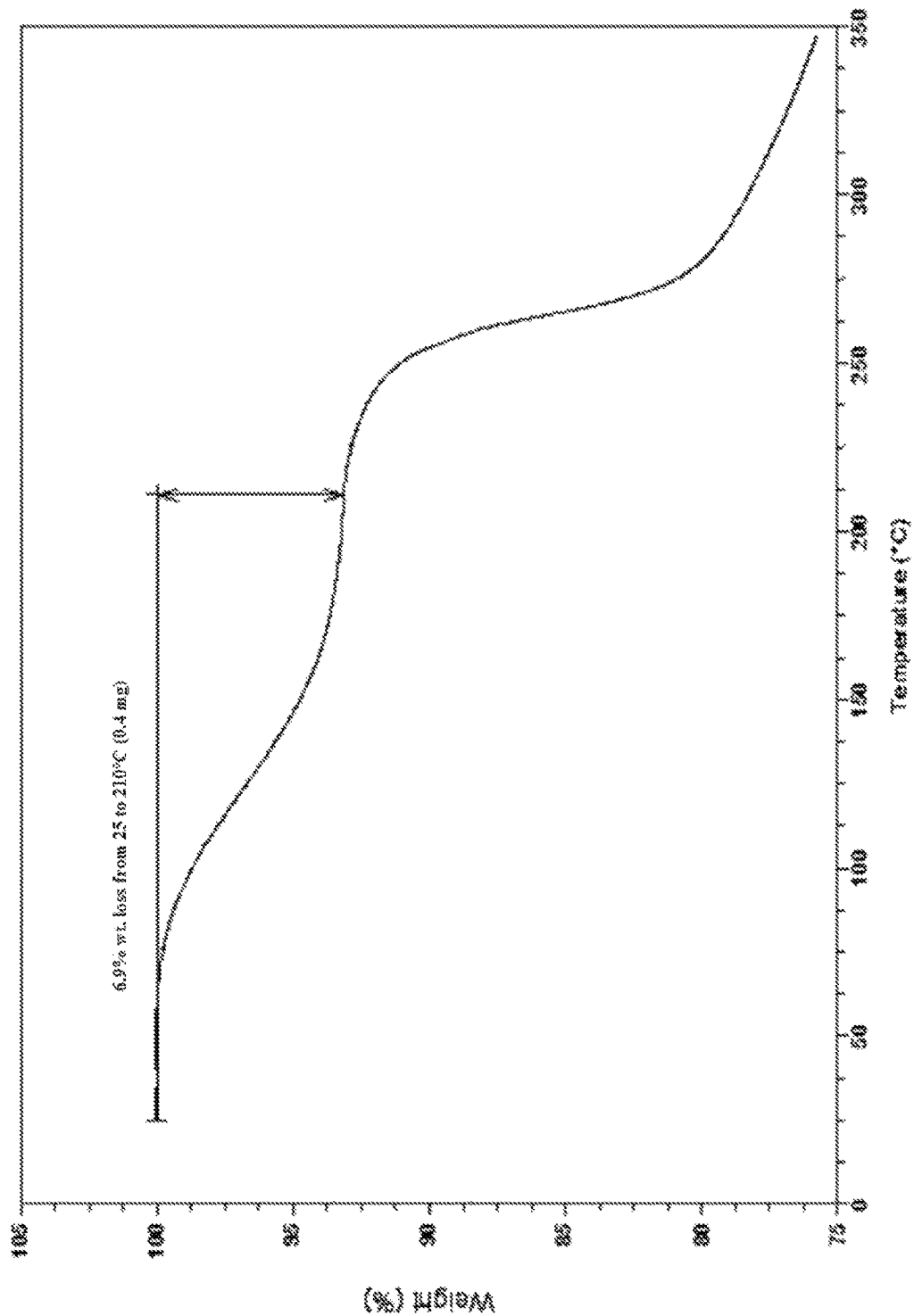
FIG. 2 is thermogravimetric analysis (TGA) of Compound I Form A.

In some embodiments, Form A is also characterized by thermogravimetric analysis (TGA) comprising a thermogram substantially as shown in FIG. 2.

Figure 3:
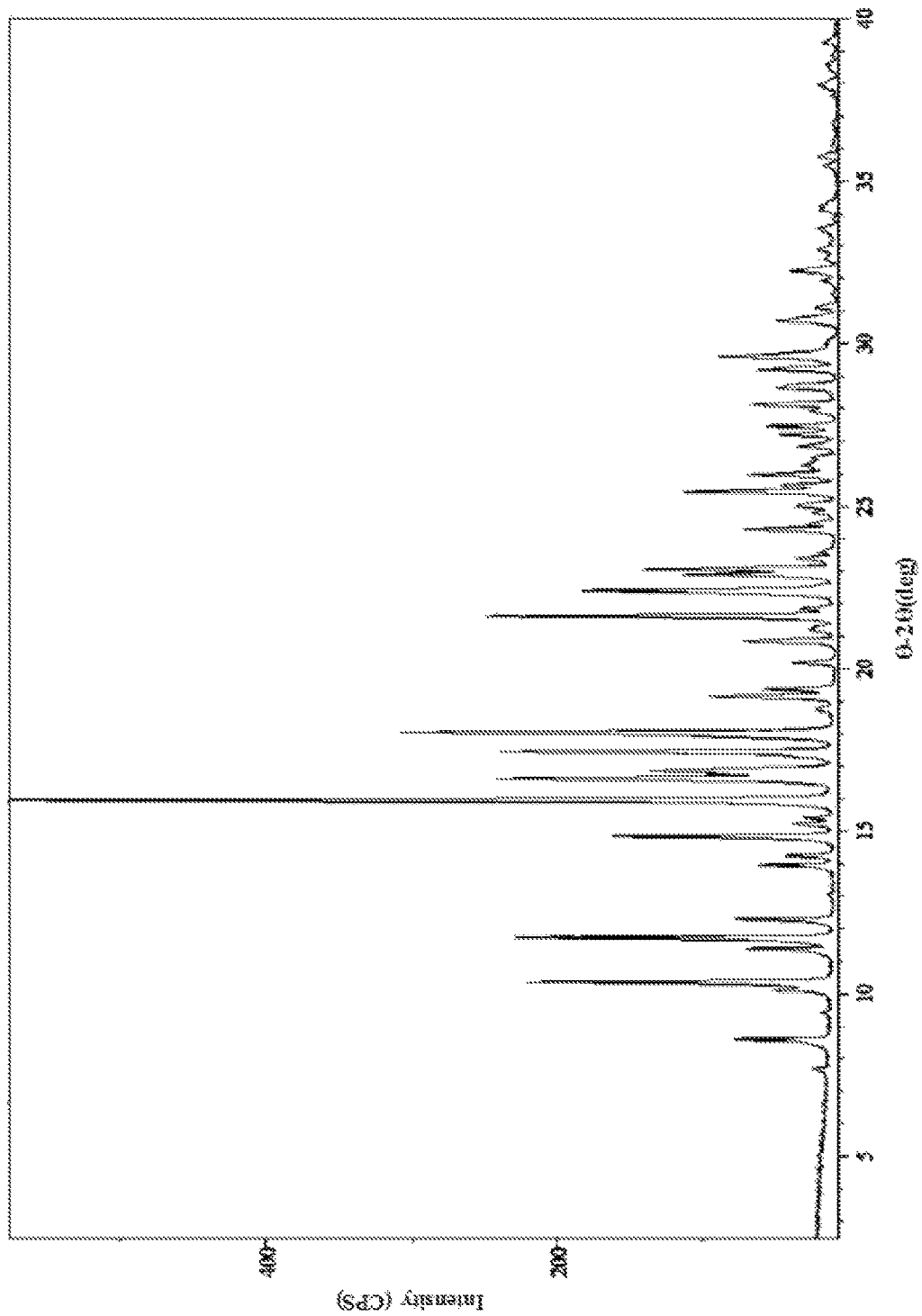
FIG. 3 is an X-ray powder diffraction pattern of Compound I Form B.

Compound I Form B is characterized by an X-ray powder diffractogram comprising peaks (±0.2°) at 10.38, 15.96, and 18.04 °2θ, as determined on a diffractometer using Cu—Kα radiation. The diffractogram comprises additional peaks (±0.2°) at 11.72 and 23.07 °2θ. Form B is also characterized by its full X-ray powder diffractogram as substantially shown in FIG. 3. Major peaks in the XRPD pattern are shown in Table 2 below. In one embodiment, this disclosure provides Compound I Form B comprising two or more peaks (±0.2°) listed in the Table 2 below as determined on a diffractometer using Cu—Kα radiation.

TABLE 2

Major Peaks in the XRPD Pattern for Compound I Form B

| °2θ (±0.2°) | d-space [Å] |
|---|---|
| 8.60 | 10.272 ± 0.238 |
| 10.38 | 8.520 ± 0.164 |
| 11.38 | 7.772 ± 0.136 |
| 11.72 | 7.542 ± 0.128 |
| 12.30 | 7.189 ± 0.116 |
| 13.95 | 6.342 ± 0.090 |
| 14.85 | 5.961 ± 0.080 |
| 15.96 | 5.550 ± 0.069 |
| 16.63 | 5.327 ± 0.064 |
| 16.78 | 5.279 ± 0.062 |
| 16.87 | 5.250 ± 0.062 |
| 17.46 | 5.075 ± 0.058 |
| 18.04 | 4.912 ± 0.054 |
| 19.15 | 4.631 ± 0.048 |
| 20.86 | 4.255 ± 0.040 |
| 21.62 | 4.107 ± 0.038 |
| 22.40 | 3.967 ± 0.035 |
| 22.89 | 3.882 ± 0.033 |
| 23.07 | 3.853 ± 0.033 |
| 24.28 | 3.663 ± 0.030 |
| 25.45 | 3.497 ± 0.027 |
| 25.98 | 3.427 ± 0.026 |
| 28.13 | 3.170 ± 0.022 |
| 29.21 | 3.055 ± 0.020 |
| 29.60 | 3.016 ± 0.020 |

In another embodiment, this disclosure provides this disclosure provides Compound I Form B comprising two or more peaks (±0.2°) listed in the Table 2A below as determined on a diffractometer using Cu—Kα radiation. Compound I Form B is characterized by an X-ray powder diffractogram comprising peaks (±0.2°) at 10.4, 16.0, and 18.0 °2θ, as determined on a diffractometer using Cu—Kα radiation. The diffractogram comprises additional peaks (±0.2°) at 11.7 and 23.1 °2θ.

TABLE 2A

Major Peaks in the XRPD Pattern for Compound I Form B

| °2θ (±0.2°) | d-space [Å] |
|---|---|
| 8.6 | 10.272 ± 0.238 |
| 10.4 | 8.520 ± 0.164 |
| 11.4 | 7.772 ± 0.136 |
| 11.7 | 7.542 ± 0.128 |
| 12.3 | 7.189 ± 0.116 |
| 14.0 | 6.342 ± 0.090 |
| 14.9 | 5.961 ± 0.080 |
| 16.0 | 5.550 ± 0.069 |
| 16.6 | 5.327 ± 0.064 |
| 16.8 | 5.279 ± 0.062 |
| 16.9 | 5.250 ± 0.062 |
| 17.5 | 5.075 ± 0.058 |
| 18.0 | 4.912 ± 0.054 |
| 19.2 | 4.631 ± 0.048 |
| 20.9 | 4.255 ± 0.040 |
| 21.6 | 4.107 ± 0.038 |
| 22.4 | 3.967 ± 0.035 |
| 22.9 | 3.882 ± 0.033 |
| 23.1 | 3.853 ± 0.033 |
| 24.3 | 3.663 ± 0.030 |
| 25.5 | 3.497 ± 0.027 |
| 26.0 | 3.427 ± 0.026 |
| 28.1 | 3.170 ± 0.022 |
| 29.2 | 3.055 ± 0.020 |
| 29.6 | 3.016 ± 0.020 |

Figure 4:
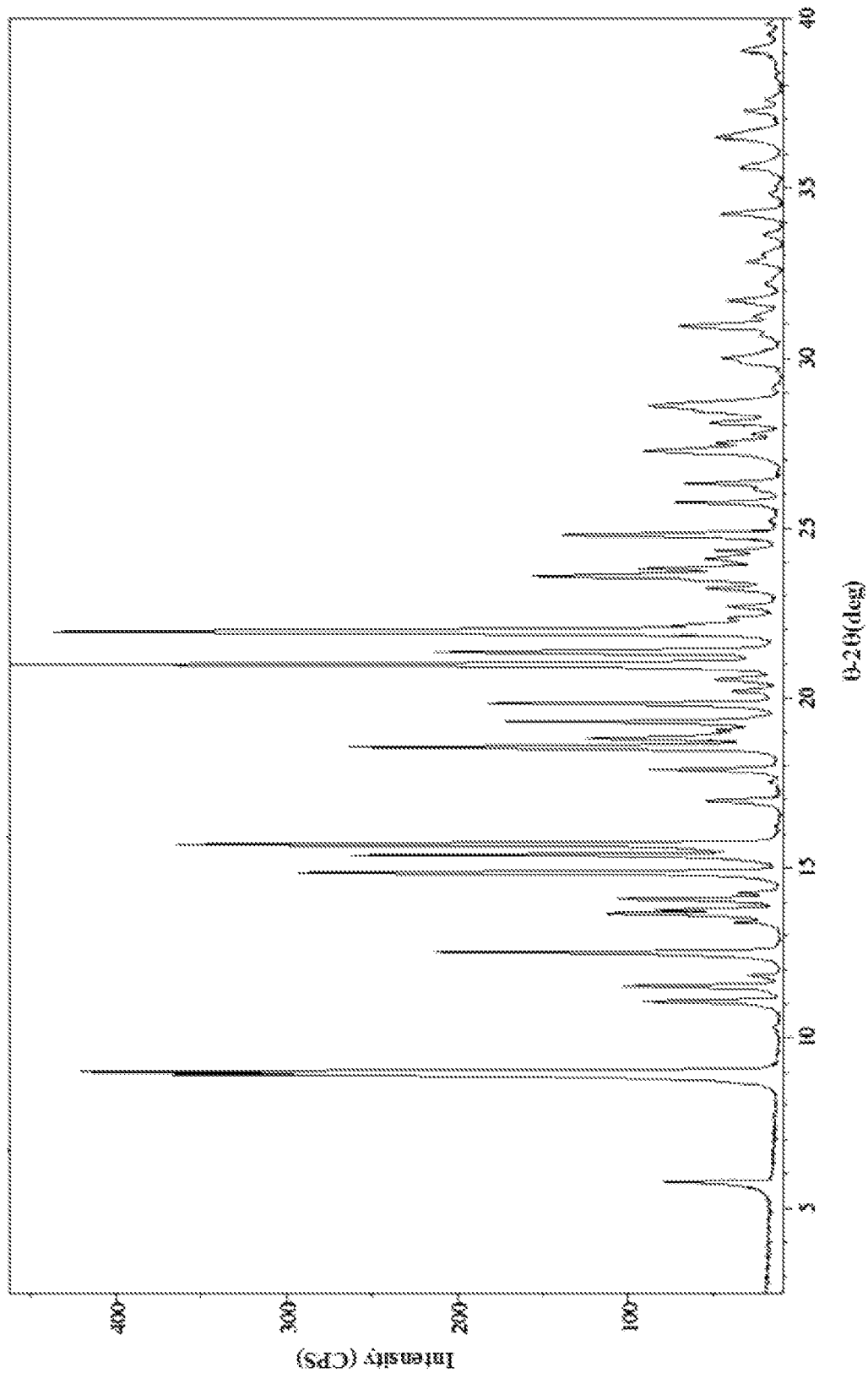
FIG. 4 is an X-ray powder diffraction pattern of Compound I Form D.

Compound I Form D is characterized by an X-ray powder diffractogram comprising peaks (±0.2°) at 9.00, 20.98, and 21.95 °2θ, as determined on a diffractometer using Cu—Kα radiation. The diffractogram comprises additional peaks (±0.2°) at 8.92 and 15.69 °2θ. Form D is also characterized by its full X-ray powder diffractogram as substantially shown in FIG. 4. Major peaks in the XRPD pattern are shown in Table 3 below. In one embodiment, this disclosure provides Compound I Form D comprising two or more peaks (±0.2°) listed in the Table 3 below as determined on a diffractometer using Cu—Kα radiation.

TABLE 3

Major Peaks in the XRPD Pattern for Compound I Form D

| °2θ (±0.2°) | d-space [Å] |
|---|---|
| 5.74 | 15.384 ± 0.536 |
| 8.92 | 9.908 ± 0.222 |
| 9.00 | 9.818 ± 0.218 |
| 11.07 | 7.988 ± 0.144 |
| 11.53 | 7.667 ± 0.133 |
| 12.52 | 7.064 ± 0.112 |
| 13.63 | 6.490 ± 0.095 |
| 13.77 | 6.426 ± 0.093 |
| 14.08 | 6.284 ± 0.089 |
| 14.86 | 5.957 ± 0.080 |
| 15.38 | 5.758 ± 0.074 |
| 15.69 | 5.643 ± 0.071 |
| 16.97 | 5.222 ± 0.061 |
| 17.89 | 4.954 ± 0.055 |
| 18.56 | 4.778 ± 0.051 |
| 18.82 | 4.712 ± 0.050 |
| 19.06 | 4.653 ± 0.048 |
| 19.29 | .597 ± 0.047 |
| 19.82 | 4.475 ± 0.045 |
| 20.55 | 4.319 ± 0.042 |
| 20.98 | 4.230 ± 0.040 |
| 21.36 | 4.157 ± 0.038 |
| 21.95 | 4.046 ± 0.036 |
| 22.13 | 4.014 ± 0.036 |
| 23.21 | 3.829 ± 0.033 |
| 23.59 | 3.768 ± 0.031 |
| 23.80 | 3.736 ± 0.031 |
| 24.10 | 3.690 ± 0.030 |
| 24.33 | 3.656 ± 0.030 |
| 24.79 | 3.589 ± 0.029 |
| 25.74 | 3.458 ± 0.026 |
| 26.32 | 3.384 ± 0.025 |
| 27.27 | 3.268 ± 0.024 |
| 27.51 | 3.239 ± 0.023 |
| 28.10 | 3.173 ± 0.022 |
| 28.59 | 3.119 ± 0.021 |

In another embodiment, this disclosure provides this disclosure provides Compound I Form D comprising two or more peaks (±0.2°) listed in the Table 3A below as determined on a diffractometer using Cu—Kα radiation. Compound I Form D is characterized by an X-ray powder diffractogram comprising peaks (±0.2°) at 9.0, 21.0, and 22.0 °2θ, as determined on a diffractometer using Cu—Kα radiation. The diffractogram comprises additional peaks (±0.2°) at 8.9 and 15.7 °2θ.

TABLE 3A

Major Peaks in the XRPD Pattern for Compound I Form D

| °2θ (±0.2°) | d-space [Å] |
|---|---|
| 5.7 | 15.384 ± 0.536 |
| 8.9 | 9.908 ± 0.222 |
| 9.0 | 9.818 ± 0.218 |
| 11.1 | 7.988 ± 0.144 |
| 11.5 | 7.667 ± 0.133 |

TABLE 3A-continued

Major Peaks in the XRPD Pattern for Compound I Form D

| °2θ (±0.2°) | d-space [Å] |
|---|---|
| 12.5 | 7.064 ± 0.112 |
| 13.6 | 6.490 ± 0.095 |
| 13.8 | 6.426 ± 0.093 |
| 14.1 | 6.284 ± 0.089 |
| 14.9 | 5.957 ± 0.080 |
| 15.4 | 5.758 ± 0.074 |
| 15.7 | 5.643 ± 0.071 |
| 17.0 | 5.222 ± 0.061 |
| 17.9 | 4.954 ± 0.055 |
| 18.6 | 4.778 ± 0.051 |
| 18.8 | 4.712 ± 0.050 |
| 19.1 | 4.653 ± 0.048 |
| 19.3 | .597 ± 0.047 |
| 19.8 | 4.475 ± 0.045 |
| 20.6 | 4.319 ± 0.042 |
| 21.0 | 4.230 ± 0.040 |
| 21.4 | 4.157 ± 0.038 |
| 22.0 | 4.046 ± 0.036 |
| 22.1 | 4.014 ± 0.036 |
| 23.2 | 3.829 ± 0.033 |
| 23.6 | 3.768 ± 0.031 |
| 23.8 | 3.736 ± 0.031 |
| 24.1 | 3.690 ± 0.030 |
| 24.3 | 3.656 ± 0.030 |
| 24.8 | 3.589 ± 0.029 |
| 25.7 | 3.458 ± 0.026 |
| 26.3 | 3.384 ± 0.025 |
| 27.3 | 3.268 ± 0.024 |
| 27.5 | 3.239 ± 0.023 |
| 28.1 | 3.173 ± 0.022 |
| 28.6 | 3.119 ± 0.021 |

Figure 5:
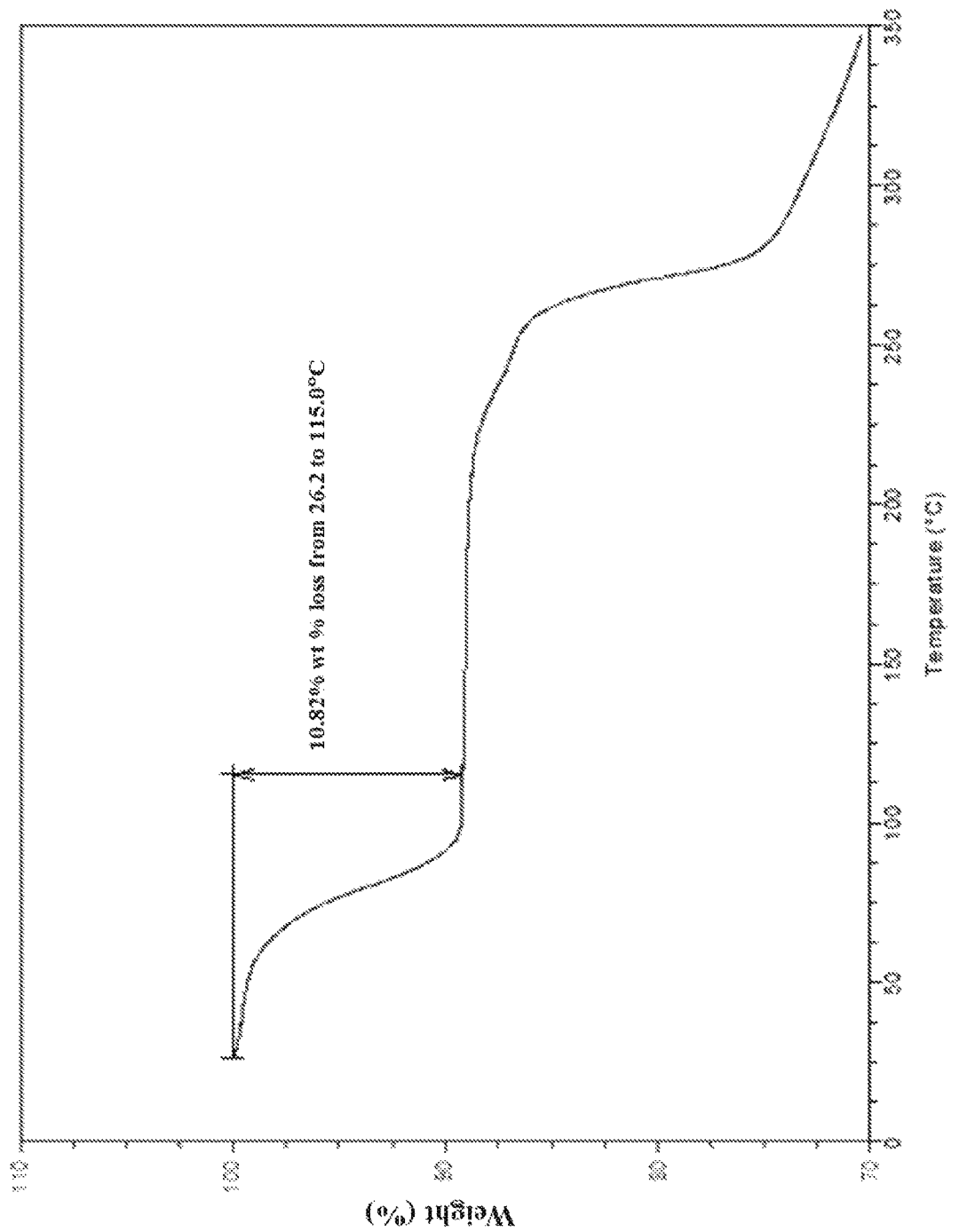
FIG. 5 is thermogravimetric analysis (TGA) of Compound I Form D.

In some embodiments, Form D is also characterized by thermogravimetric analysis (TGA) comprising a thermogram substantially as shown in FIG. 5.

Figure 6:
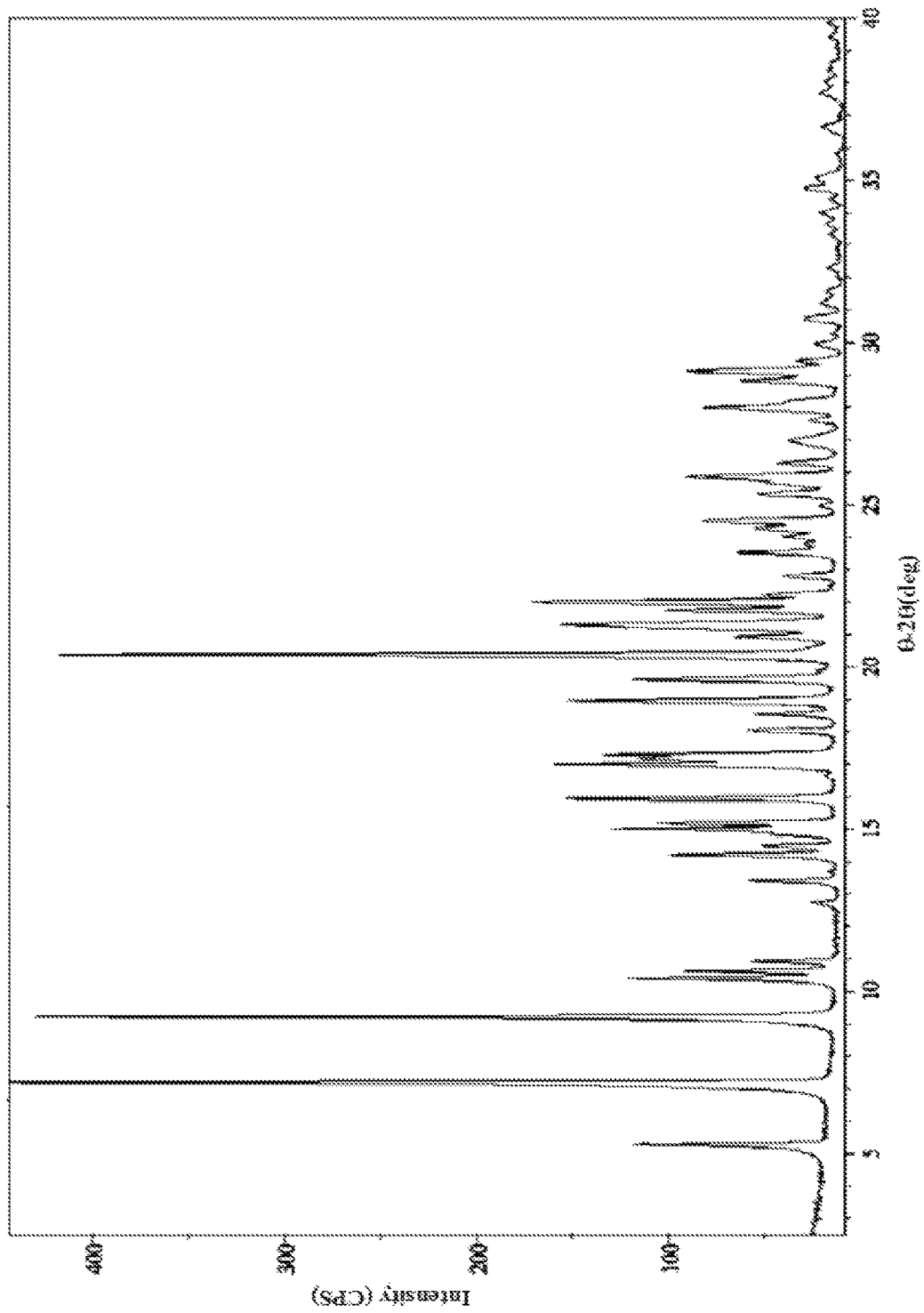
FIG. 6 is an X-ray powder diffraction pattern of Compound I Form E.

In some Compound I Form E is characterized by an X-ray powder diffractogram comprising peaks (±0.2°) at 7.19, 9.23, and 20.38 °2θ, as determined on a diffractometer using Cu—Kα radiation. The diffractogram comprises additional peaks (±0.2°) at 16.99 and 18.94 °2θ. Form E is also characterized by its full X-ray powder diffractogram as substantially shown in FIG. 6. Major peaks in the XRPD pattern are shown in Table 4 below. In one embodiment, this disclosure provides Compound I Form E comprising two or more peaks (±0.2°) listed in the Table 4 below as determined on a diffractometer using Cu—Kα radiation.

TABLE 4

Major Peaks in the XRPD Pattern for Compound I Form E

| °2θ (±0.2°) | d-space [Å] |
|---|---|
| 5.30 | 16.666 ± 0.629 |
| 7.19 | 12.279 ± 0.341 |
| 9.23 | 9.573 ± 0.207 |
| 10.39 | 8.504 ± 0.163 |
| 10.63 | 8.316 ± 0.156 |
| 10.92 | 8.098 ± 0.148 |
| 13.42 | 6.593 ± 0.098 |
| 14.21 | 6.229 ± 0.087 |
| 15.01 | 5.898 ± 0.078 |
| 15.20 | 5.826 ± 0.076 |
| 15.96 | 5.548 ± 0.069 |
| 16.99 | 5.213 ± 0.061 |
| 17.16 | 5.163 ± 0.060 |
| 17.29 | 5.125 ± 0.059 |
| 18.03 | 4.915 ± 0.054 |
| 18.94 | 4.682 ± 0.049 |
| 19.62 | 4.522 ± 0.046 |
| 20.38 | 4.355 ± 0.042 |
| 20.94 | 4.239 ± 0.040 |
| 21.22 | 4.184 ± 0.039 |
| 21.32 | 4.164 ± 0.039 |
| 21.75 | 4.083 ± 0.037 |
| 22.00 | 4.037 ± 0.036 |
| 23.54 | 3.777 ± 0.032 |
| 24.51 | 3.630 ± 0.029 |
| 25.87 | 3.442 ± 0.026 |
| 27.99 | 3.185 ± 0.022 |
| 28.81 | 3.096 ± 0.021 |
| 29.12 | 3.064 ± 0.021 |

In some Compound I Form E is characterized by an X-ray powder diffractogram comprising peaks (±0.2°) at 7.2, 9.2, and 20.4 °2θ, as determined on a diffractometer using Cu—Kα radiation. The diffractogram comprises additional peaks (±0.2°) at 17.0 and 18.9 °2θ. Form E is also characterized by its full X-ray powder diffractogram as substantially shown in FIG. 6. Major peaks in the XRPD pattern are shown in Table 4A below. In one embodiment, this disclosure provides Compound I Form E comprising two or more peaks (±0.2°) listed in the Table 4A below as determined on a diffractometer using Cu—Kα radiation.

TABLE 4A

Major Peaks in the XRPD Pattern for Compound I Form E

| °2θ (±0.2°) | d-space [Å] |
|---|---|
| 5.3 | 16.666 ± 0.629 |
| 7.2 | 12.279 ± 0.341 |
| 9.2 | 9.573 ± 0.207 |
| 10.4 | 8.504 ± 0.163 |
| 10.6 | 8.316 ± 0.156 |
| 10.9 | 8.098 ± 0.148 |
| 13.4 | 6.593 ± 0.098 |
| 14.2 | 6.229 ± 0.087 |
| 15.0 | 5.898 ± 0.078 |
| 15.2 | 5.826 ± 0.076 |
| 16.0 | 5.548 ± 0.069 |
| 17.0 | 5.213 ± 0.061 |
| 17.2 | 5.163 ± 0.060 |
| 17.3 | 5.125 ± 0.059 |
| 18.0 | 4.915 ± 0.054 |
| 18.9 | 4.682 ± 0.049 |
| 19.6 | 4.522 ± 0.046 |
| 20.4 | 4.355 ± 0.042 |
| 20.9 | 4.239 ± 0.040 |
| 21.2 | 4.184 ± 0.039 |
| 21.3 | 4.164 ± 0.039 |
| 21.8 | 4.083 ± 0.037 |
| 22.0 | 4.037 ± 0.036 |
| 23.5 | 3.777 ± 0.032 |
| 24.5 | 3.630 ± 0.029 |
| 25.9 | 3.442 ± 0.026 |
| 28.0 | 3.185 ± 0.022 |
| 28.8 | 3.096 ± 0.021 |
| 29.1 | 3.064 ± 0.021 |

Figure 7:
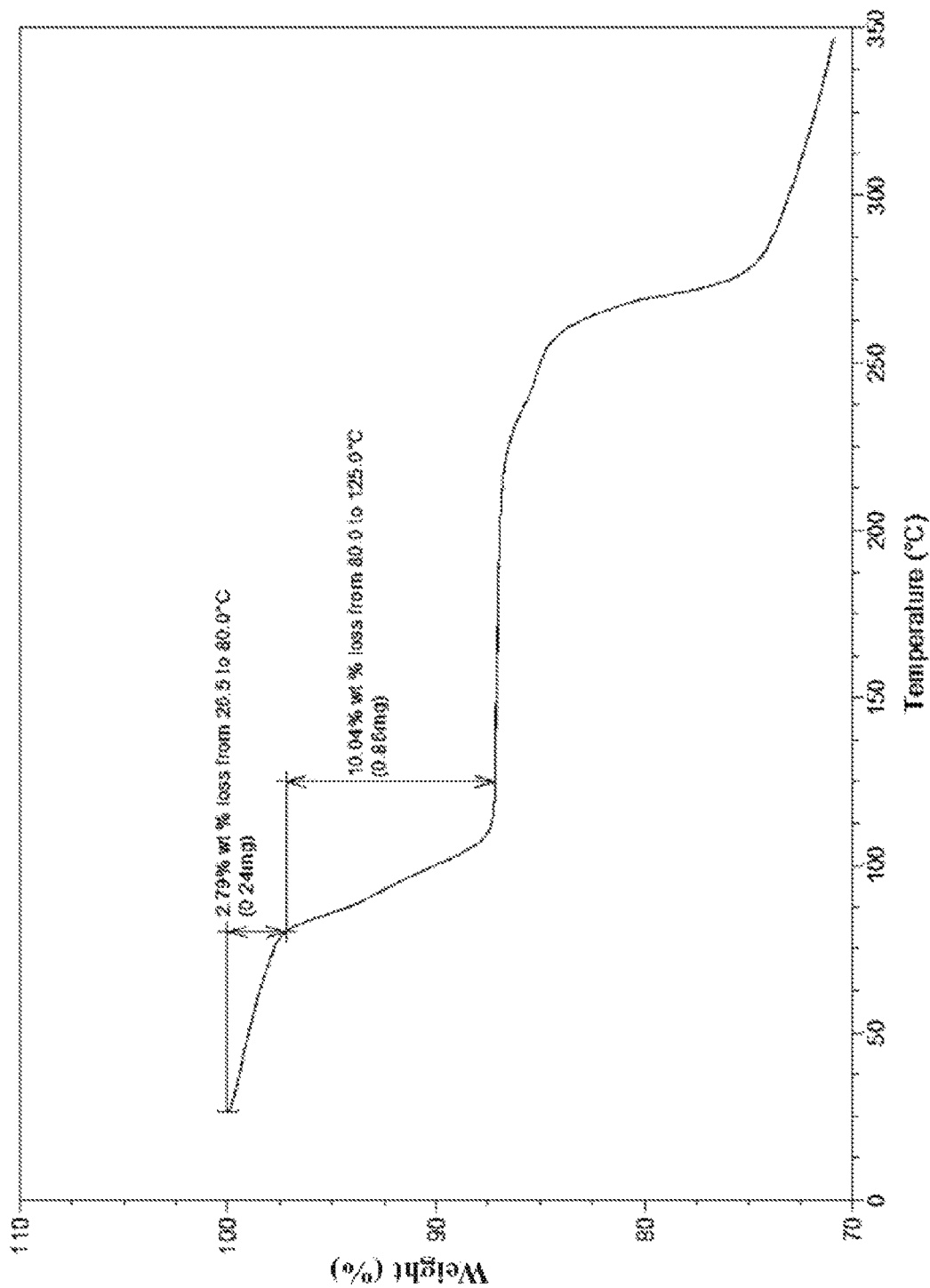
FIG. 7 is thermogravimetric analysis (TGA) of Compound I Form E.

In some embodiments, Form E is also characterized by thermogravimetric analysis (TGA) comprising a thermogram substantially as shown in FIG. 7.

Figure 8:
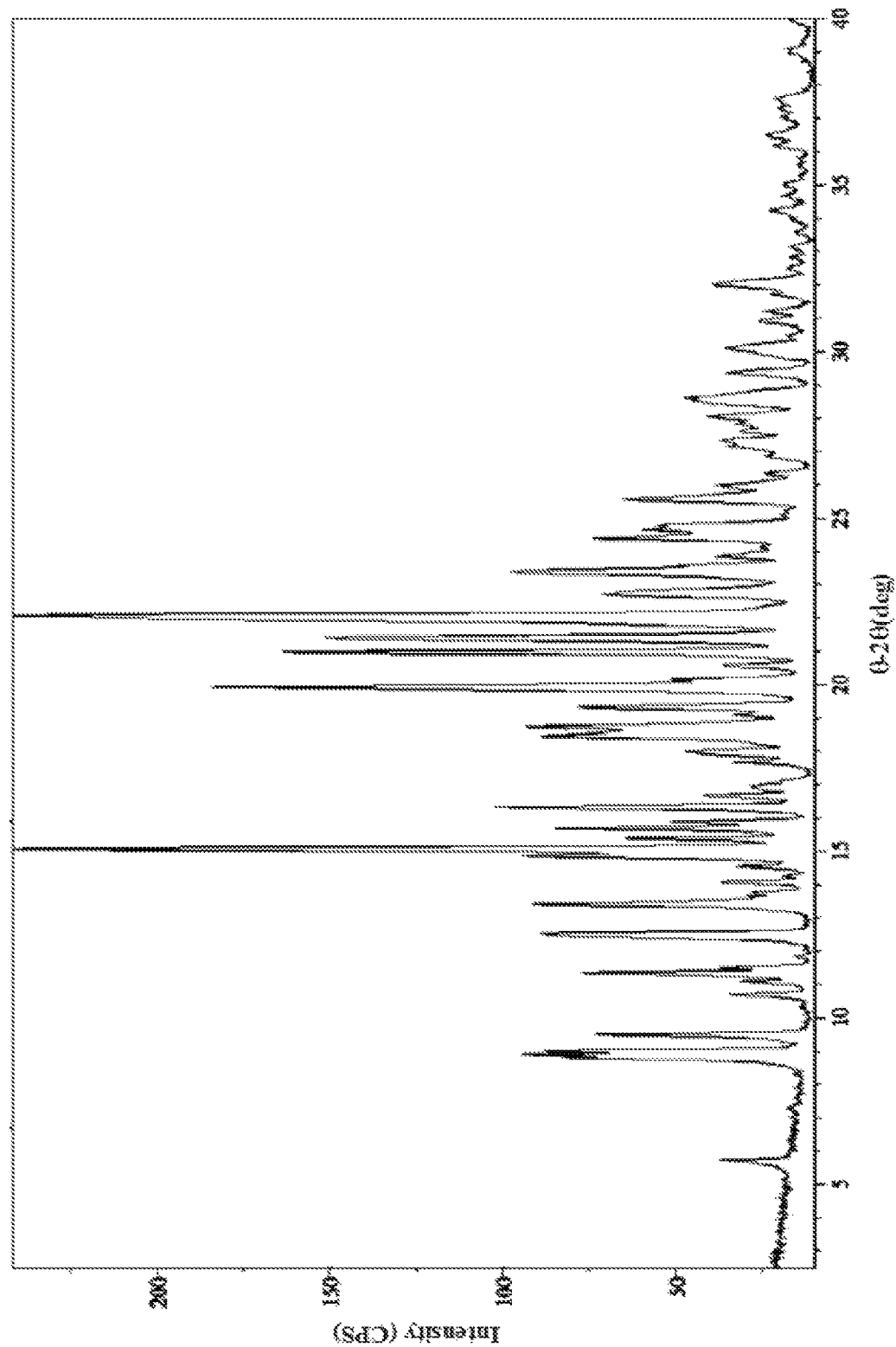
FIG. 8 is an X-ray powder diffraction pattern of Compound I Form F.

Compound I Form F is characterized by an X-ray powder diffractogram comprising peaks (±0.2°) at 15.08, 19.93, and 22.07 °2θ, as determined on a diffractometer using Cu—Kα radiation. The diffractogram comprises additional peaks (±0.2°) at 8.91 and 21.42 °2θ. Form F is also characterized by its full X-ray powder diffractogram as substantially shown in FIG. 8. Major peaks in the XRPD pattern are shown in Table 5 below. In one embodiment, this disclosure provides Compound I Form E comprising two or more peaks (±0.2°) listed in the Table 5 below as determined on a diffractometer using Cu—Kα radiation.

TABLE 5

Major Peaks in the XRPD Pattern for Compound I Form F

| °2θ (±0.2°) | d-space [Å] |
|---|---|
| 5.73 | 15.413 ± 0.538 |
| 8.81 | 10.025 ± 0.227 |
| 8.91 | 9.916 ± 0.222 |
| 9.01 | 9.811 ± 0.217 |
| 9.50 | 9.306 ± 0.196 |
| 11.34 | 7.798 ± 0.137 |
| 11.51 | 7.682 ± 0.133 |
| 12.50 | 7.078 ± 0.113 |
| 13.42 | 6.592 ± 0.098 |
| 14.08 | 6.286 ± 0.089 |
| 14.86 | 5.957 ± 0.080 |
| 15.08 | 5.871 ± 0.077 |
| 15.39 | 5.753 ± 0.074 |
| 15.70 | 5.640 ± 0.071 |
| 15.88 | 5.577 ± 0.070 |
| 16.33 | 5.425 ± 0.066 |
| 16.66 | 5.318 ± 0.063 |
| 17.93 | 4.943 ± 0.055 |
| 17.99 | 4.927 ± 0.054 |
| 18.45 | 4.806 ± 0.052 |
| 18.55 | 4.778 ± 0.051 |
| 18.73 | 4.733 ± 0.050 |
| 19.10 | 4.643 ± 0.048 |
| 19.32 | 4.591 ± 0.047 |
| 19.93 | 4.452 ± 0.044 |
| 20.15 | 4.404 ± 0.043 |
| 20.58 | 4.313 ± 0.041 |
| 20.99 | 4.230 ± 0.040 |
| 21.42 | 4.146 ± 0.038 |
| 22.07 | 4.025 ± 0.036 |
| 22.75 | 3.906 ± 0.034 |
| 23.39 | 3.800 ± 0.032 |
| 23.86 | 3.726 ± 0.031 |
| 24.41 | 3.644 ± 0.029 |
| 25.56 | 3.483 ± 0.027 |
| 25.96 | 3.429 ± 0.026 |
| 27.32 | 3.262 ± 0.023 |
| 28.07 | 3.176 ± 0.022 |
| 28.60 | 3.118 ± 0.021 |

Compound I Form F is characterized by an X-ray powder diffractogram comprising peaks (±0.2°) at 15.1, 19.9, and 22.1 °2θ, as determined on a diffractometer using Cu—Kα radiation. The diffractogram comprises additional peaks (±0.2°) at 8.9 and 21.4 °2θ. Form F is also characterized by its full X-ray powder diffractogram as substantially shown in FIG. 8. Major peaks in the XRPD pattern are shown in Table 5A below. In one embodiment, this disclosure provides Compound I Form E comprising two or more peaks (±0.2°) listed in the Table 5A below as determined on a diffractometer using Cu—Kα radiation.

TABLE 5A

Major Peaks in the XRPD Pattern for Compound I Form F

| °2θ (±0.2°) | d-space [Å] |
|---|---|
| 5.7 | 15.413 ± 0.538 |
| 8.8 | 10.025 ± 0.227 |
| 8.9 | 9.916 ± 0.222 |
| 9.0 | 9.811 ± 0.217 |
| 9.5 | 9.306 ± 0.196 |
| 11.3 | 7.798 ± 0.137 |

TABLE 5A-continued

Major Peaks in the XRPD Pattern for Compound I Form F

| °2θ (±0.2°) | d-space [Å] |
|---|---|
| 11.5 | 7.682 ± 0.133 |
| 12.5 | 7.078 ± 0.113 |
| 13.4 | 6.592 ± 0.098 |
| 14.1 | 6.286 ± 0.089 |
| 14.9 | 5.957 ± 0.080 |
| 15.1 | 5.871 ± 0.077 |
| 15.4 | 5.753 ± 0.074 |
| 15.7 | 5.640 ± 0.071 |
| 15.9 | 5.577 ± 0.070 |
| 16.3 | 5.425 ± 0.066 |
| 16.7 | 5.318 ± 0.063 |
| 17.9 | 4.943 ± 0.055 |
| 18.0 | 4.927 ± 0.054 |
| 18.5 | 4.806 ± 0.052 |
| 18.6 | 4.778 ± 0.051 |
| 18.7 | 4.733 ± 0.050 |
| 19.1 | 4.643 ± 0.048 |
| 19.3 | 4.591 ± 0.047 |
| 19.9 | 4.452 ± 0.044 |
| 20.2 | 4.404 ± 0.043 |
| 20.6 | 4.313 ± 0.041 |
| 21.0 | 4.230 ± 0.040 |
| 21.4 | 4.146 ± 0.038 |
| 22.1 | 4.025 ± 0.036 |
| 22.8 | 3.906 ± 0.034 |
| 23.4 | 3.800 ± 0.032 |
| 23.9 | 3.726 ± 0.031 |
| 24.4 | 3.644 ± 0.029 |
| 25.6 | 3.483 ± 0.027 |
| 26.0 | 3.429 ± 0.026 |
| 27.3 | 3.262 ± 0.023 |
| 28.1 | 3.176 ± 0.022 |
| 28.6 | 3.118 ± 0.021 |

Figure 9:
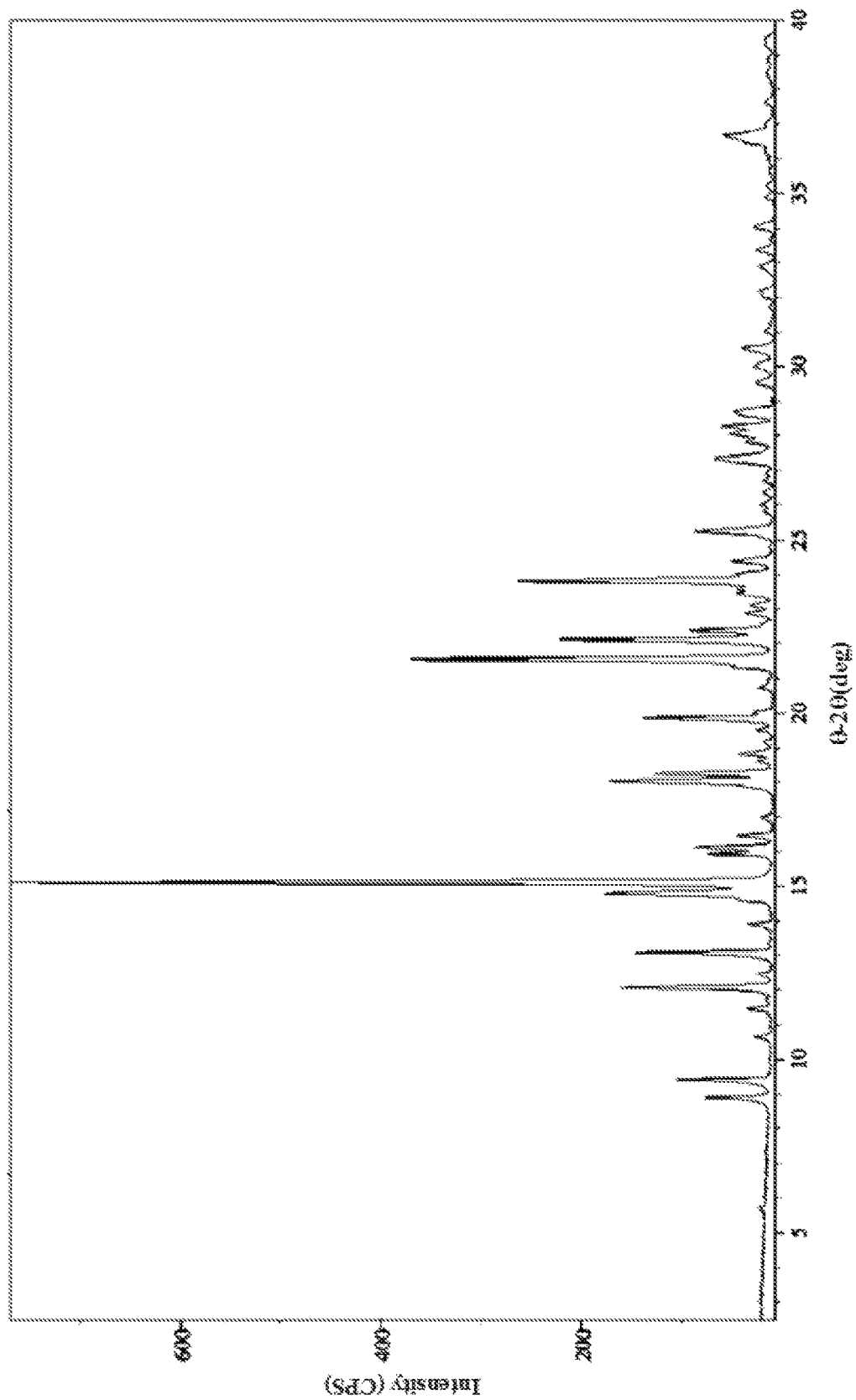
FIG. 9 is an X-ray powder diffraction pattern of Compound I Form G.

Compound I Form G is characterized by an X-ray powder diffractogram comprising peaks (±0.2°) at 14.77, 15.12, and 21.54 °2θ, as determined on a diffractometer using Cu—Kα radiation. The diffractogram comprises additional peaks (±0.2°) at 12.09 and 18.26 °2θ. Form G is also characterized by its full X-ray powder diffractogram as substantially shown in FIG. 9. Major peaks in the XRPD pattern are shown in Table 6 below. In one embodiment, this disclosure provides Compound I Form G comprising two or more peaks (±0.2°) listed in the Table 6 below as determined on a diffractometer using Cu—Kα radiation.

TABLE 6

Major Peaks in the XRPD Pattern for Compound I Form G

| °2θ (±0.2°) | d-space [Å] |
|---|---|
| 8.90 | 9.933 ± 0.223 |
| 9.42 | 9.377 ± 0.199 |
| 12.09 | 7.317 ± 0.121 |
| 13.08 | 6.764 ± 0.103 |
| 14.77 | 5.993 ± 0.081 |
| 14.81 | 5.975 ± 0.080 |
| 15.12 | 5.854 ± 0.077 |
| 15.93 | 5.559 ± 0.069 |
| 16.11 | 5.497 ± 0.068 |
| 18.03 | 4.916 ± 0.054 |
| 18.26 | 4.854 ± 0.053 |
| 19.84 | 4.471 ± 0.045 |
| 21.54 | 4.121 ± 0.038 |
| 22.11 | 4.017 ± 0.036 |
| 22.38 | 3.970 ± 0.035 |
| 23.81 | 3.734 ± 0.031 |
| 25.26 | 3.523 ± 0.027 |

Compound I Form G is characterized by an X-ray powder diffractogram comprising peaks (±0.2°) at 14.8, 15.1, and 21.5 °2θ, as determined on a diffractometer using Cu—Kα radiation. The diffractogram comprises additional peaks (±0.2°) at 12.1 and 18.3 °2θ. Form G is also characterized by its full X-ray powder diffractogram as substantially shown in FIG. 9. Major peaks in the XRPD pattern are shown in Table 6A below. In one embodiment, this disclosure provides Compound I Form G comprising two or more peaks (±0.2°) listed in the Table 6A below as determined on a diffractometer using Cu—Kα radiation.

TABLE 6A

Major Peaks in the XRPD Pattern for Compound I Form G

| °2θ (±0.2°) | d-space [Å] |
|---|---|
| 8.9 | 9.933 ± 0.223 |
| 9.4 | 9.377 ± 0.199 |
| 12.1 | 7.317 ± 0.121 |
| 13.1 | 6.764 ± 0.103 |
| 14.8 | 5.993 ± 0.081 |
| 14.8 | 5.975 ± 0.080 |
| 15.1 | 5.854 ± 0.077 |
| 15.9 | 5.559 ± 0.069 |
| 16.1 | 5.497 ± 0.068 |
| 18.1 | 4.916 ± 0.054 |
| 18.7 | 4.854 ± 0.053 |
| 19.8 | 4.471 ± 0.045 |
| 21.5 | 4.121 ± 0.038 |
| 22.1 | 4.017 ± 0.036 |
| 22.4 | 3.970 ± 0.035 |
| 23.8 | 3.734 ± 0.031 |
| 25.3 | 3.523 ± 0.027 |

Figure 10:
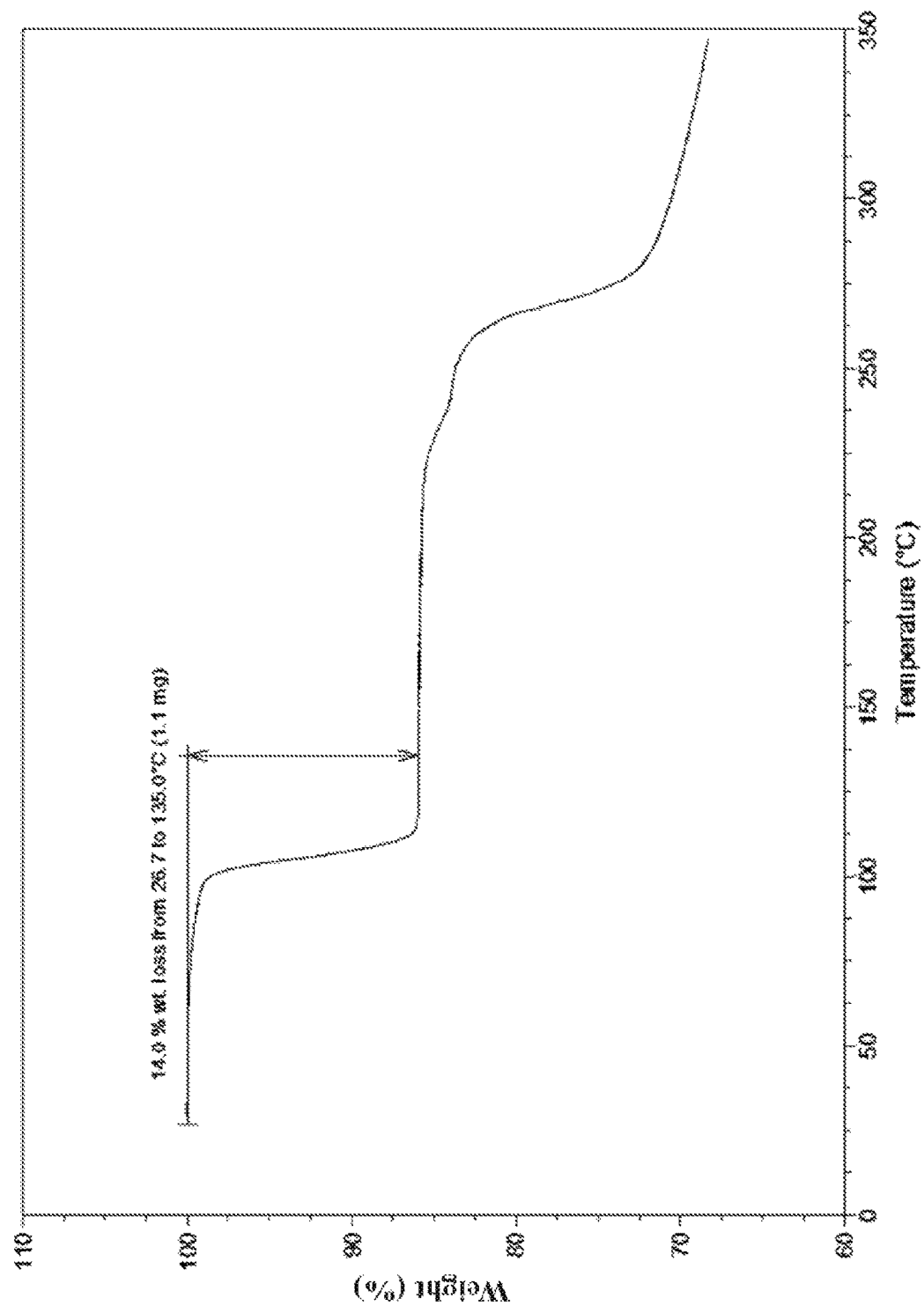
FIG. 10 is thermogravimetric analysis (TGA) of Compound I Form G.

In some embodiments, Form G is also characterized by thermogravimetric analysis (TGA) comprising a thermogram substantially as shown in FIG. 10.

Figure 11:
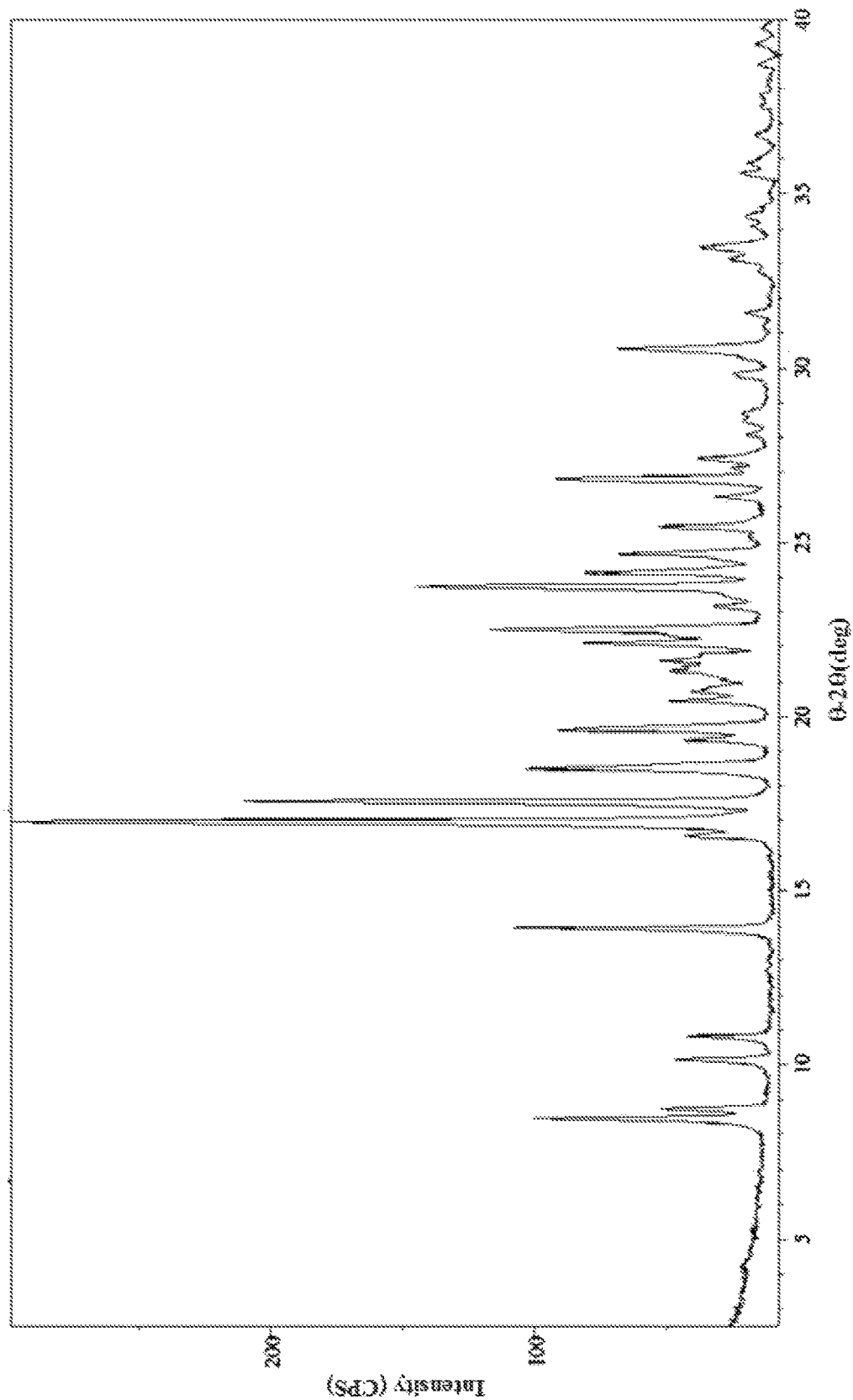
FIG. 11 is an X-ray powder diffraction pattern of Compound I Form H.

Compound I Form H is characterized by an X-ray powder diffractogram comprising peaks (±0.2°) at 8.46, 16.97, and 23.72 °2θ, as determined on a diffractometer using Cu—Kα radiation. The diffractogram comprises additional peaks (±0.2°) at 17.55 and 18.50 °2θ. Form H is also characterized by its full X-ray powder diffractogram as substantially shown in FIG. 11. Major peaks in the XRPD pattern are shown in Table 7 below. In one embodiment, this disclosure provides Compound I Form H comprising two or more peaks (±0.2°) listed in the Table 7 below as determined on a diffractometer using Cu—Kα radiation.

TABLE 7

Major Peaks in the XRPD Pattern for Compound I Form H

| °2θ (±0.2°) | d-space [Å] |
|---|---|
| 8.46 | 10.439 ± 0.246 |
| 8.73 | 10.120 ± 0.231 |
| 10.15 | 8.712 ± 0.171 |
| 10.82 | 8.172 ± 0.151 |
| 13.93 | 6.352 ± 0.091 |
| 16.97 | 5.219 ± 0.061 |
| 17.55 | 5.050 ± 0.057 |
| 18.50 | 4.791 ± 0.051 |
| 19.64 | 4.516 ± 0.046 |
| 20.46 | 4.338 ± 0.042 |
| 21.31 | 4.167 ± 0.039 |
| 21.43 | 4.144 ± 0.038 |
| 21.60 | 4.111 ± 0.038 |
| 22.10 | 4.020 ± 0.036 |
| 22.49 | 3.950 ± 0.035 |
| 23.72 | 3.748 ± 0.031 |
| 24.13 | 3.686 ± 0.030 |
| 24.67 | 3.606 ± 0.029 |

TABLE 7-continued

Major Peaks in the XRPD Pattern for Compound I Form H

| °2θ (±0.2°) | d-space [Å] |
|---|---|
| 25.44 | 3.498 ± 0.027 |
| 26.82 | 3.322 ± 0.024 |

Compound I Form H is characterized by an X-ray powder diffractogram comprising peaks (±0.2°) at 8.5, 17.0, and 23.7° 2°, as determined on a diffractometer using Cu—Kα radiation. The diffractogram comprises additional peaks (±0.2°) at 17.6 and 18.5 °2θ. Form H is also characterized by its full X-ray powder diffractogram as substantially shown in FIG. 11. Major peaks in the XRPD pattern are shown in Table 7A below. In one embodiment, this disclosure provides Compound I Form H comprising two or more peaks (±0.2°) listed in the Table 7A below as determined on a diffractometer using Cu—Kα radiation.

TABLE 7A

Major Peaks in the XRPD Pattern for Compound I Form H

| °2θ (±0.2°) | d-space [Å] |
|---|---|
| 8.5 | 10.439 ± 0.246 |
| 8.7 | 10.120 ± 0.231 |
| 10.2 | 8.712 ± 0.171 |
| 10.8 | 8.172 ± 0.151 |
| 13.9 | 6.352 ± 0.091 |
| 17.0 | 5.219 ± 0.061 |
| 17.6 | 5.050 ± 0.057 |
| 18.5 | 4.791 ± 0.051 |
| 19.6 | 4.516 ± 0.046 |
| 20.5 | 4.338 ± 0.042 |
| 21.3 | 4.167 ± 0.039 |
| 21.4 | 4.144 ± 0.038 |
| 21.6 | 4.111 ± 0.038 |
| 22.1 | 4.020 ± 0.036 |
| 22.5 | 3.950 ± 0.035 |
| 23.7 | 3.748 ± 0.031 |
| 24.1 | 3.686 ± 0.030 |
| 24.7 | 3.606 ± 0.029 |
| 25.4 | 3.498 ± 0.027 |
| 26.8 | 3.322 ± 0.024 |

Figure 12:
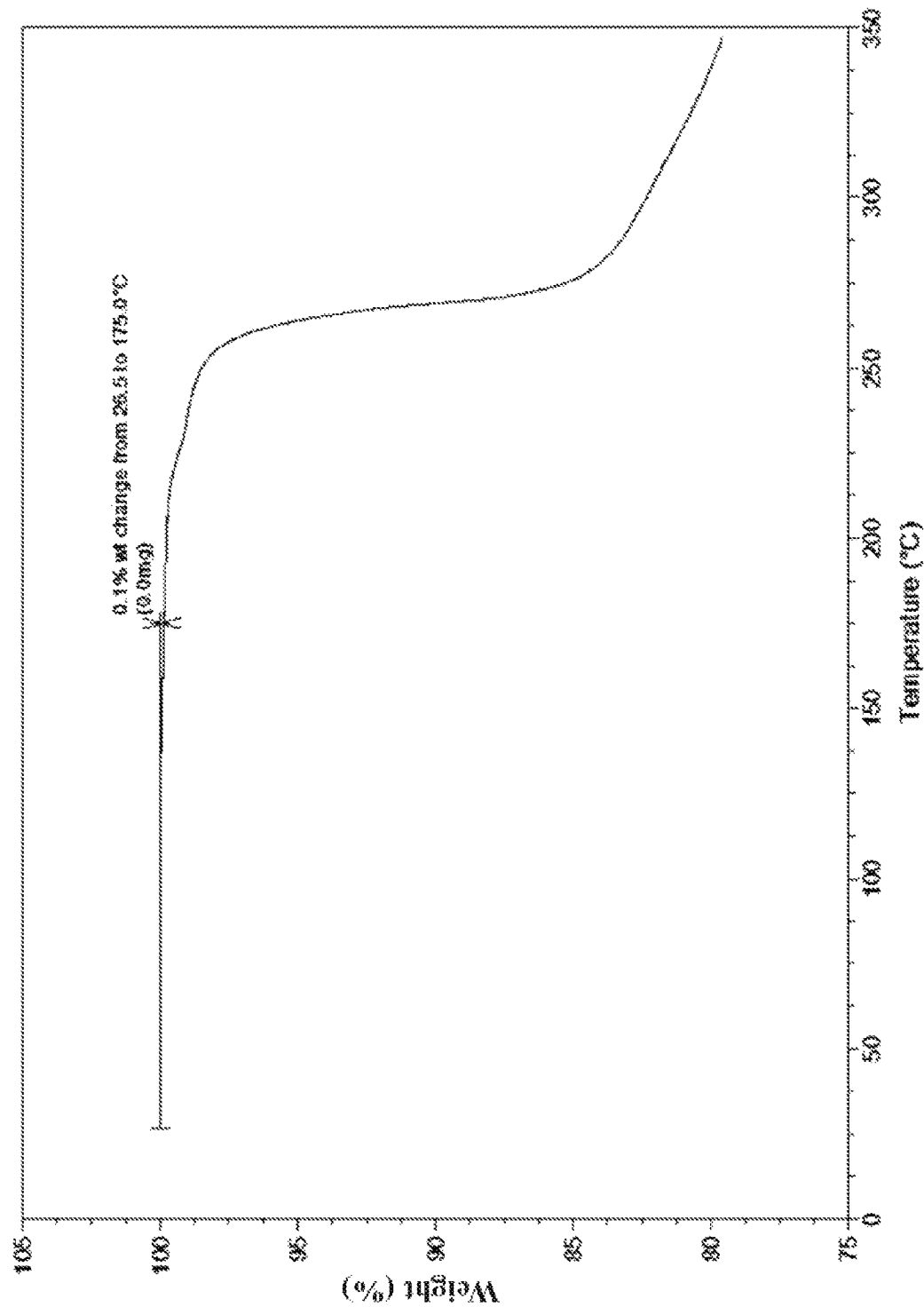
FIG. 12 is thermogravimetric analysis (TGA) of Compound I Form H.

In some embodiments, Form H is also characterized by thermogravimetric analysis (TGA) comprising a thermogram substantially as shown in FIG. 12.

Figure 13:
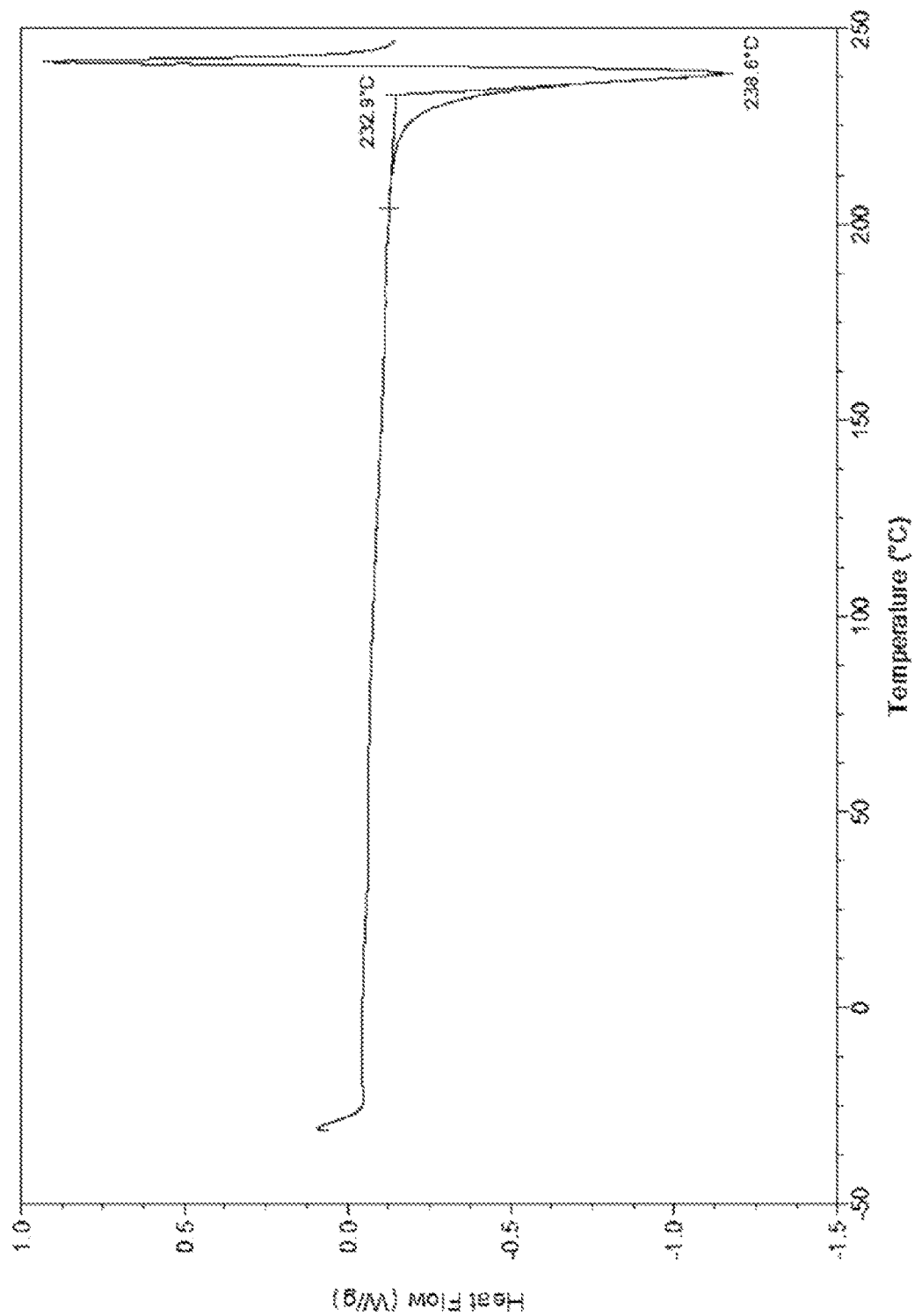
FIG. 13 is differential scanning calorimetry (DSC) curve of Compound I Form H.

In some embodiments, Form H is also characterized by its differential scanning calorimetry (DSC) curve comprising an endotherm at about 238° C. In another embodiment, the DSC curve is substantially as shown in FIG. 13.

Figure 14:
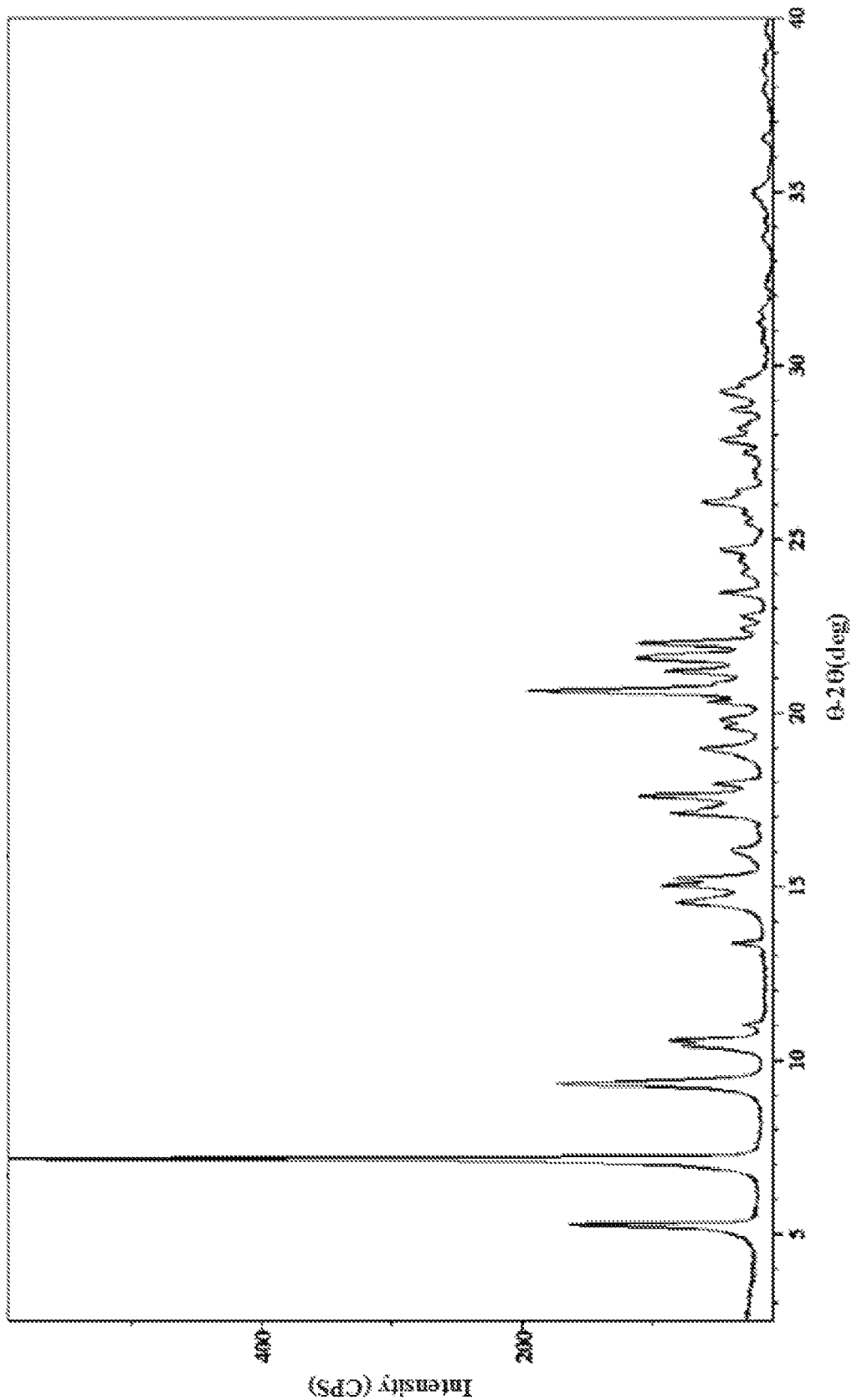
FIG. 14 is an X-ray powder diffraction pattern of Compound I Form I.

Compound I Form I is characterized by an X-ray powder diffractogram comprising peaks (±0.2°) at 7.17, 9.33, and 20.63 °2θ, as determined on a diffractometer using Cu—Kα radiation. The diffractogram comprises additional peaks (±0.2°) at 5.27 and 17.60 °2θ. Form I is also characterized by its full X-ray powder diffractogram as substantially shown in FIG. 14. Major peaks in the XRPD pattern are shown in Table 8 below. In one embodiment, this disclosure provides Compound I Form I comprising two or more peaks (±0.2°) listed in the Table 8 below as determined on a diffractometer using Cu—Kα radiation.

TABLE 8

Major Peaks in the XRPD Pattern for Compound I Form I

| °2θ (±0.2°) | d-space [Å] |
|---|---|
| 5.27 | 16.760 ± 0.636 |
| 7.17 | 12.319 ± 0.343 |
| 9.33 | 9.4733 ± 0.203 |
| 10.41 | 8.488 ± 0.163 |
| 10.58 | 8.357 ± 0.158 |
| 14.55 | 6.083 ± 0.083 |
| 15.03 | 5.891 ± 0.078 |
| 15.24 | 5.811 ± 0.076 |
| 17.11 | 5.177 ± 0.060 |
| 17.60 | 5.034 ± 0.057 |
| 20.63 | 4.302 ± 0.041 |
| 21.19 | 4.189 ± 0.039 |
| 21.57 | 4.116 ± 0.038 |
| 22.00 | 4.037 ± 0.036 |

Compound I Form I is characterized by an X-ray powder diffractogram comprising peaks (±0.2°) at 7.2, 9.3, and 20.6 °2θ, as determined on a diffractometer using Cu—Kα radiation. The diffractogram comprises additional peaks (±0.2°) at 5.3 and 17.6 °2θ. Form I is also characterized by its full X-ray powder diffractogram as substantially shown in FIG. 14. Major peaks in the XRPD pattern are shown in Table 8A below. In one embodiment, this disclosure provides Compound I Form I comprising two or more peaks (±0.2°) listed in the Table 8A below as determined on a diffractometer using Cu—Kα radiation.

TABLE 8A

Major Peaks in the XRPD Pattern for Compound I Form I

| °2θ (±0.2°) | d-space [Å] |
|---|---|
| 5.3 | 16.760 ± 0.636 |
| 7.2 | 12.319 ± 0.343 |
| 9.3 | 9.4733 ± 0.203 |
| 10.4 | 8.488 ± 0.163 |
| 10.6 | 8.357 ± 0.158 |
| 14.6 | 6.083 ± 0.083 |
| 15.0 | 5.891 ± 0.078 |
| 15.2 | 5.811 ± 0.076 |
| 17.1 | 5.177 ± 0.060 |
| 17.6 | 5.034 ± 0.057 |
| 20.6 | 4.302 ± 0.041 |
| 21.2 | 4.189 ± 0.039 |
| 21.6 | 4.116 ± 0.038 |
| 22.0 | 4.037 ± 0.036 |

Figure 15:
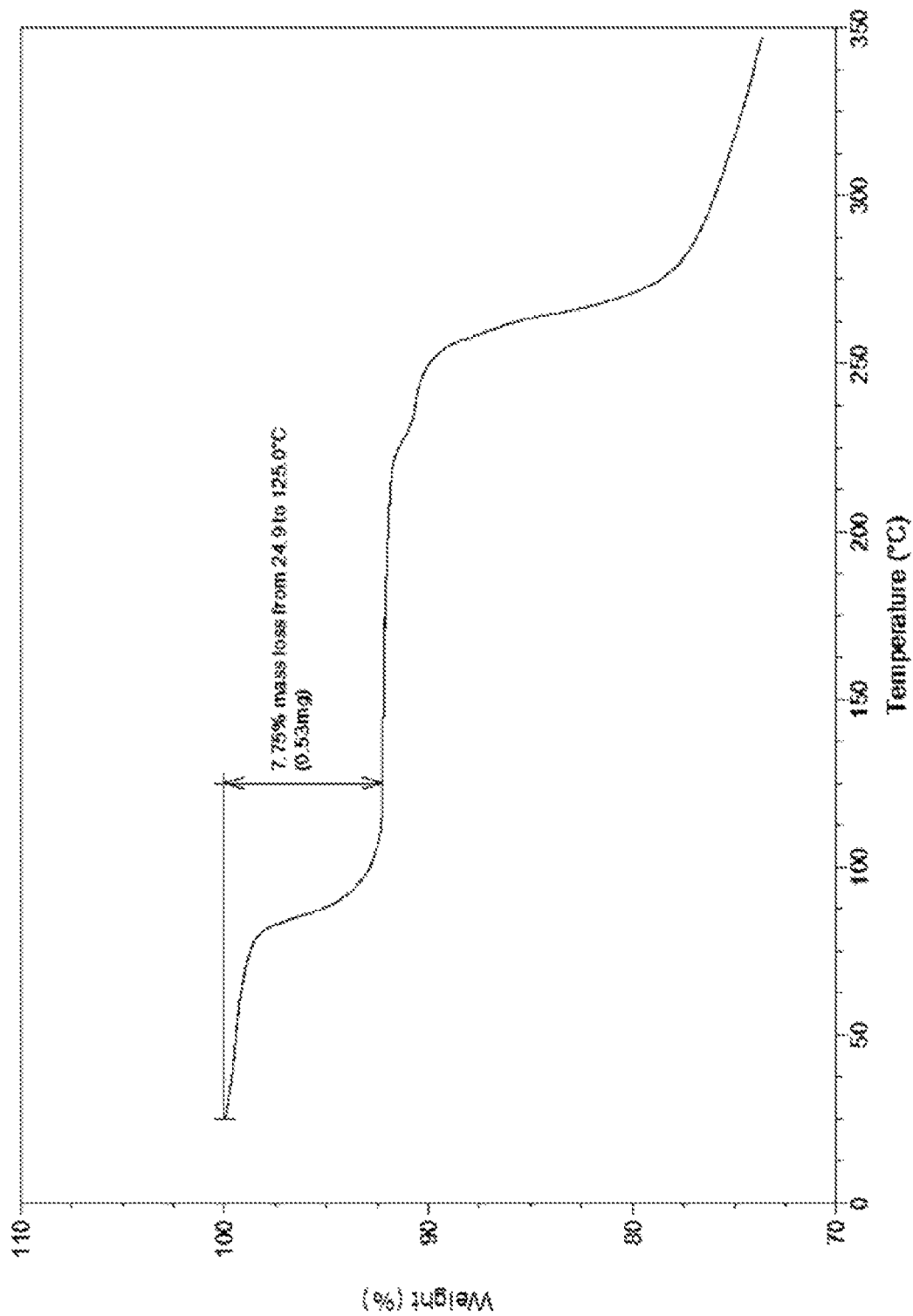
FIG. 15 is thermogravimetric analysis (TGA) of Compound I Form I.

In some embodiments, Form I is also characterized by thermogravimetric analysis (TGA) comprising a thermogram substantially as shown in FIG. 15.

Figure 16:
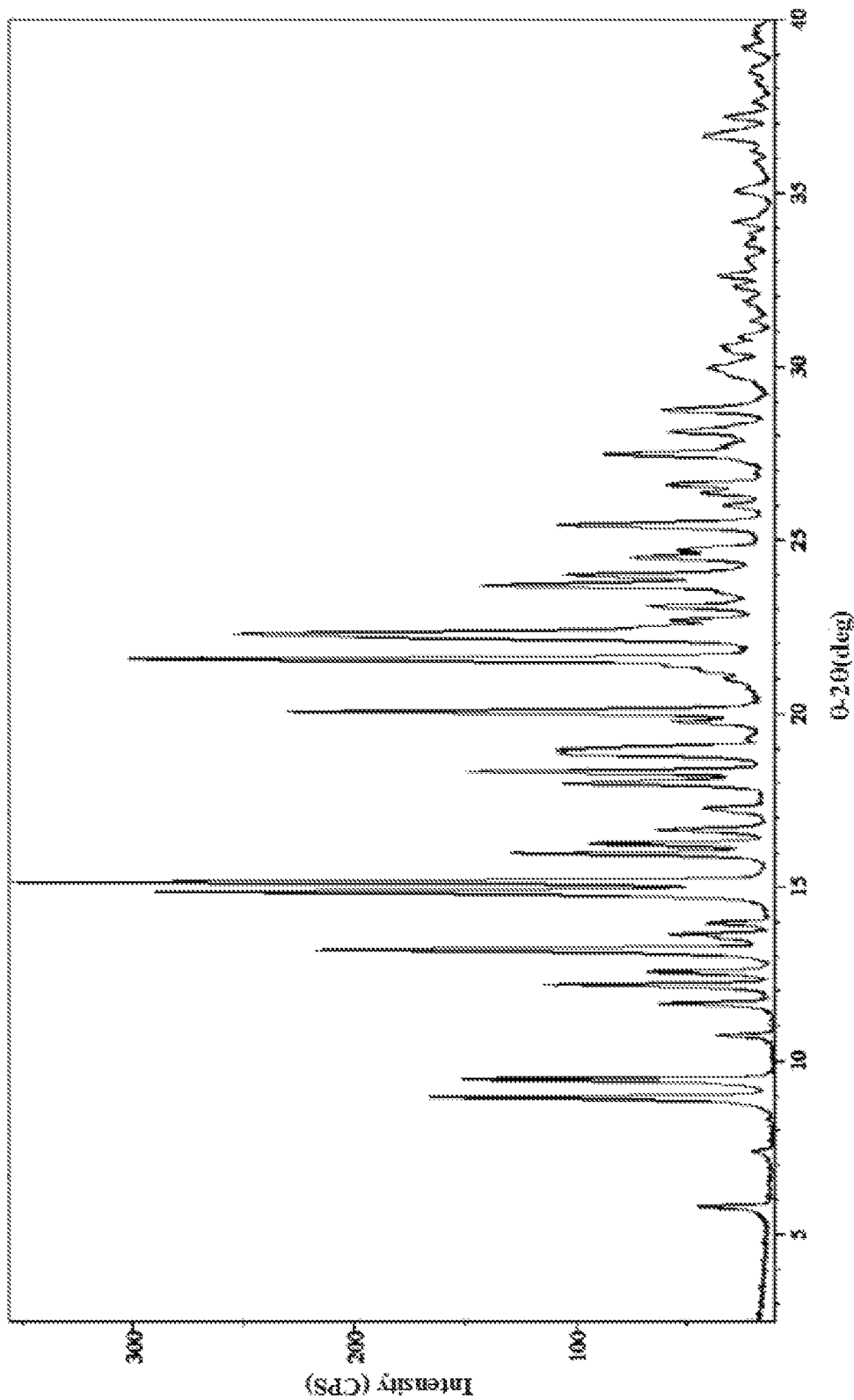
FIG. 16 is an X-ray powder diffraction pattern of Compound I Form J.

Compound I Form J is characterized by an X-ray powder diffractogram comprising peaks (±0.2°) at 14.87, 20.06, and 21.58 °2θ, as determined on a diffractometer using Cu—Kα radiation. The diffractogram comprises additional peaks (±0.2°) at 13.20 and 22.30 °2θ. Form J is also characterized by its full X-ray powder diffractogram as substantially shown in FIG. 16. Major peaks in the XRPD pattern are shown in Table 9 below. In one embodiment, this disclosure provides Compound I Form J comprising two or more peaks (±0.2°) listed in the Table 9 below as determined on a diffractometer using Cu—Kα radiation.

TABLE 9

Major Peaks in the XRPD Pattern for Compound I Form J

| °2θ (±0.2°) | d-space [Å] |
|---|---|
| 5.81 | 15.204 ± 0.523 |
| 8.95 | 9.870 ± 0.220 |
| 9.47 | 9.335 ± 0.197 |
| 11.66 | 7.585 ± 0.130 |
| 12.18 | 7.258 ± 0.119 |
| 12.57 | 7.037 ± 0.112 |
| 13.20 | 6.704 ± 0.101 |
| 13.63 | 6.491 ± 0.095 |
| 14.87 | 5.954 ± 0.080 |
| 15.16 | 5.841 ± 0.077 |
| 15.98 | 5.540 ± 0.069 |
| 16.25 | 5.452 ± 0.067 |
| 16.65 | 5.320 ± 0.063 |
| 18.00 | 4.925 ± 0.054 |
| 18.33 | 4.835 ± 0.052 |
| 18.85 | 4.705 ± 0.049 |
| 18.96 | 4.678 ± 0.049 |
| 19.76 | 4.490 ± 0.045 |
| 20.06 | 4.424 ± 0.044 |
| 21.38 | 4.152 ± 0.038 |
| 21.58 | 4.115 ± 0.038 |
| 22.30 | 3.983 ± 0.035 |
| 22.68 | 3.917 ± 0.034 |
| 23.09 | 3.849 ± 0.033 |
| 23.70 | 3.752 ± 0.031 |
| 23.99 | 3.707 ± 0.030 |
| 24.52 | 3.628 ± 0.029 |
| 24.72 | 3.598 ± 0.029 |
| 25.43 | 3.500 ± 0.027 |
| 26.36 | 3.378 ± 0.025 |
| 26.59 | 3.349 ± 0.025 |
| 27.48 | 3.243 ± 0.023 |
| 28.13 | 3.170 ± 0.022 |
| 28.75 | 3.103 ± 0.021 |

Compound I Form J is characterized by an X-ray powder diffractogram comprising peaks (±0.2°) at 14.8, 20.1, and 21.6 °2θ, as determined on a diffractometer using Cu—Kα radiation. The diffractogram comprises additional peaks (±0.2°) at 13.2 and 22.3 °2θ. Form J is also characterized by its full X-ray powder diffractogram as substantially shown in FIG. 16. Major peaks in the XRPD pattern are shown in Table 9A below. In one embodiment, this disclosure provides Compound I Form J comprising two or more peaks (±0.2°) listed in the Table 9A below as determined on a diffractometer using Cu—Kα radiation.

TABLE 9A

Major Peaks in the XRPD Pattern for Compound I Form J

| °2θ (±0.2°) | d-space [Å] |
|---|---|
| 5.8 | 15.204 ± 0.523 |
| 9.0 | 9.870 ± 0.220 |
| 9.5 | 9.335 ± 0.197 |
| 11.7 | 7.585 ± 0.130 |
| 12.2 | 7.258 ± 0.119 |
| 12.6 | 7.037 ± 0.112 |
| 13.2 | 6.704 ± 0.101 |
| 13.6 | 6.491 ± 0.095 |
| 14.8 | 5.954 ± 0.080 |
| 15.2 | 5.841 ± 0.077 |
| 16.0 | 5.540 ± 0.069 |
| 16.3 | 5.452 ± 0.067 |
| 16.7 | 5.320 ± 0.063 |
| 18.0 | 4.925 ± 0.054 |
| 18.3 | 4.835 ± 0.052 |
| 18.9 | 4.705 ± 0.049 |
| 19.0 | 4.678 ± 0.049 |
| 19.8 | 4.490 ± 0.045 |
| 20.1 | 4.424 ± 0.044 |

TABLE 9A-continued

Major Peaks in the XRPD Pattern for Compound I Form J

| °2θ (±0.2°) | d-space [Å] |
|---|---|
| 21.4 | 4.152 ± 0.038 |
| 21.6 | 4.115 ± 0.038 |
| 22.3 | 3.983 ± 0.035 |
| 22.7 | 3.917 ± 0.034 |
| 23.1 | 3.849 ± 0.033 |
| 23.7 | 3.752 ± 0.031 |
| 24.0 | 3.707 ± 0.030 |
| 24.5 | 3.628 ± 0.029 |
| 24.7 | 3.598 ± 0.029 |
| 25.4 | 3.500 ± 0.027 |
| 26.4 | 3.378 ± 0.025 |
| 26.6 | 3.349 ± 0.025 |
| 27.5 | 3.243 ± 0.023 |
| 28.1 | 3.170 ± 0.022 |
| 28.8 | 3.103 ± 0.021 |

Figure 17:
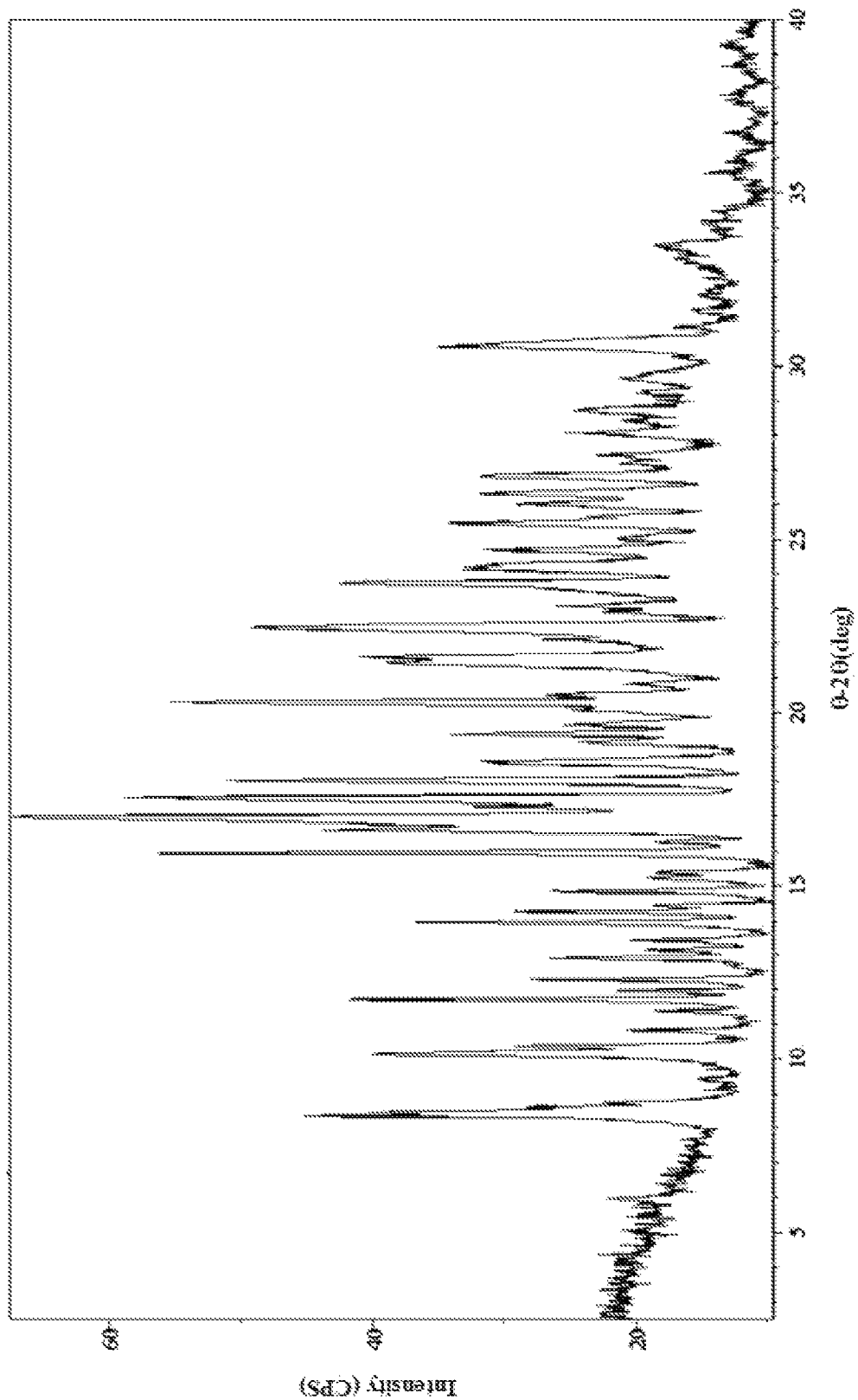
FIG. 17 is an X-ray powder diffraction pattern of Compound I Form K.

Compound I Form K is characterized by an X-ray powder diffractogram comprising peaks (±0.2°) at 15.95, 18.03, and 20.29 °2θ, as determined on a diffractometer using Cu—Kα radiation. The diffractogram comprises additional peaks (±0.2°) at 8.37 and 11.71 °2θ. Form K is also characterized by its full X-ray powder diffractogram as substantially shown in FIG. 17. Major peaks in the XRPD pattern are shown in Table 10 below. In one embodiment, this disclosure provides Compound I Form K comprising two or more peaks (±0.2°) listed in the Table 10 below as determined on a diffractometer using Cu—Kα radiation.

TABLE 10

Major Peaks in the XRPD Pattern for Compound I Form K (+Form H)

| °2θ (±0.2°) | d-space [Å] |
|---|---|
| 8.37 | 10.559 ± 0.252 |
| 8.46 | 10.440 ± 0.246 |
| 8.61 | 10.267 ± 0.238 |
| 10.15 | 8.709 ± 0.171 |
| 10.37 | 8.521 ± 0.164 |
| 11.71 | 7.549 ± 0.128 |
| 12.30 | 7.191 ± 0.116 |
| 13.93 | 6.351 ± 0.091 |
| 14.25 | 6.209 ± 0.087 |
| 14.84 | 5.965 ± 0.080 |
| 15.95 | 5.551 ± 0.069 |
| 16.62 | 5.331 ± 0.064 |
| 16.97 | 5.220 ± 0.061 |
| 17.27 | 5.129 ± 0.059 |
| 17.53 | 5.055 ± 0.057 |
| 18.03 | 4.916 ± 0.054 |
| 18.56 | 4.776 ± 0.051 |
| 19.38 | 4.576 ± 0.047 |
| 20.29 | 4.374 ± 0.043 |
| 21.43 | 4.143 ± 0.038 |
| 21.60 | 4.111 ± 0.038 |
| 22.11 | 4.018 ± 0.036 |
| 22.45 | 3.957 ± 0.035 |
| 23.73 | 3.747 ± 0.031 |

Compound I Form K is characterized by an X-ray powder diffractogram comprising peaks (±0.2°) at 16.0, 18.0, and 20.3 °2θ, as determined on a diffractometer using Cu—Kα radiation. The diffractogram comprises additional peaks (±0.2°) at 8.4 and 11.7 °2θ. Form K is also characterized by its full X-ray powder diffractogram as substantially shown in FIG. 17. Major peaks in the XRPD pattern are shown in Table 10A below. In one embodiment, this disclosure provides Compound I Form K comprising two or more peaks (±0.2°) listed in the Table 10A below as determined on a diffractometer using Cu—Kα radiation.

TABLE 10A

Major Peaks in the XRPD Pattern for Compound I Form K (+Form H)

| °2θ (±0.2°) | d-space [Å] |
|---|---|
| 8.4 | 10.559 ± 0.252 |
| 8.5 | 10.440 ± 0.246 |
| 8.6 | 10.267 ± 0.238 |
| 10.2 | 8.709 ± 0.171 |
| 10.4 | 8.521 ± 0.164 |
| 11.7 | 7.549 ± 0.128 |
| 12.3 | 7.191 ± 0.116 |
| 14.0 | 6.351 ± 0.091 |
| 14.3 | 6.209 ± 0.087 |
| 14.8 | 5.965 ± 0.080 |
| 16.0 | 5.551 ± 0.069 |
| 16.6 | 5.331 ± 0.064 |
| 17.0 | 5.220 ± 0.061 |
| 17.3 | 5.129 ± 0.059 |
| 17.5 | 5.055 ± 0.057 |
| 18.0 | 4.916 ± 0.054 |
| 18.6 | 4.776 ± 0.051 |
| 19.4 | 4.576 ± 0.047 |
| 20.3 | 4.374 ± 0.043 |
| 21.4 | 4.143 ± 0.038 |
| 21.6 | 4.111 ± 0.038 |
| 22.1 | 4.018 ± 0.036 |
| 22.5 | 3.957 ± 0.035 |
| 23.7 | 3.747 ± 0.031 |

Figure 18:
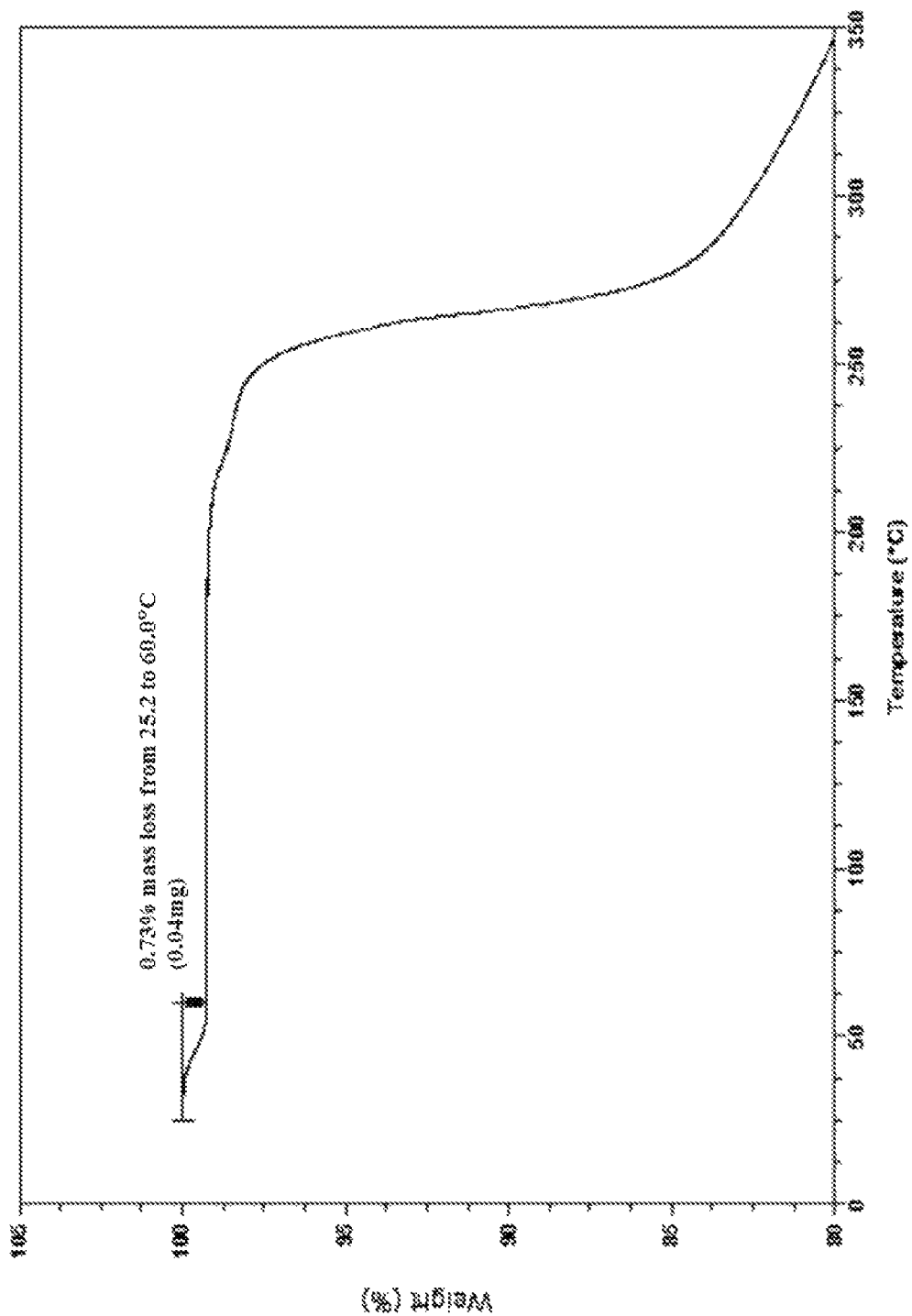
FIG. 18 is thermogravimetric analysis (TGA) of Compound I Form K.

In some embodiments, Form K is also characterized by thermogravimetric analysis (TGA) comprising a thermogram substantially as shown in FIG. 18.

Figure 19:
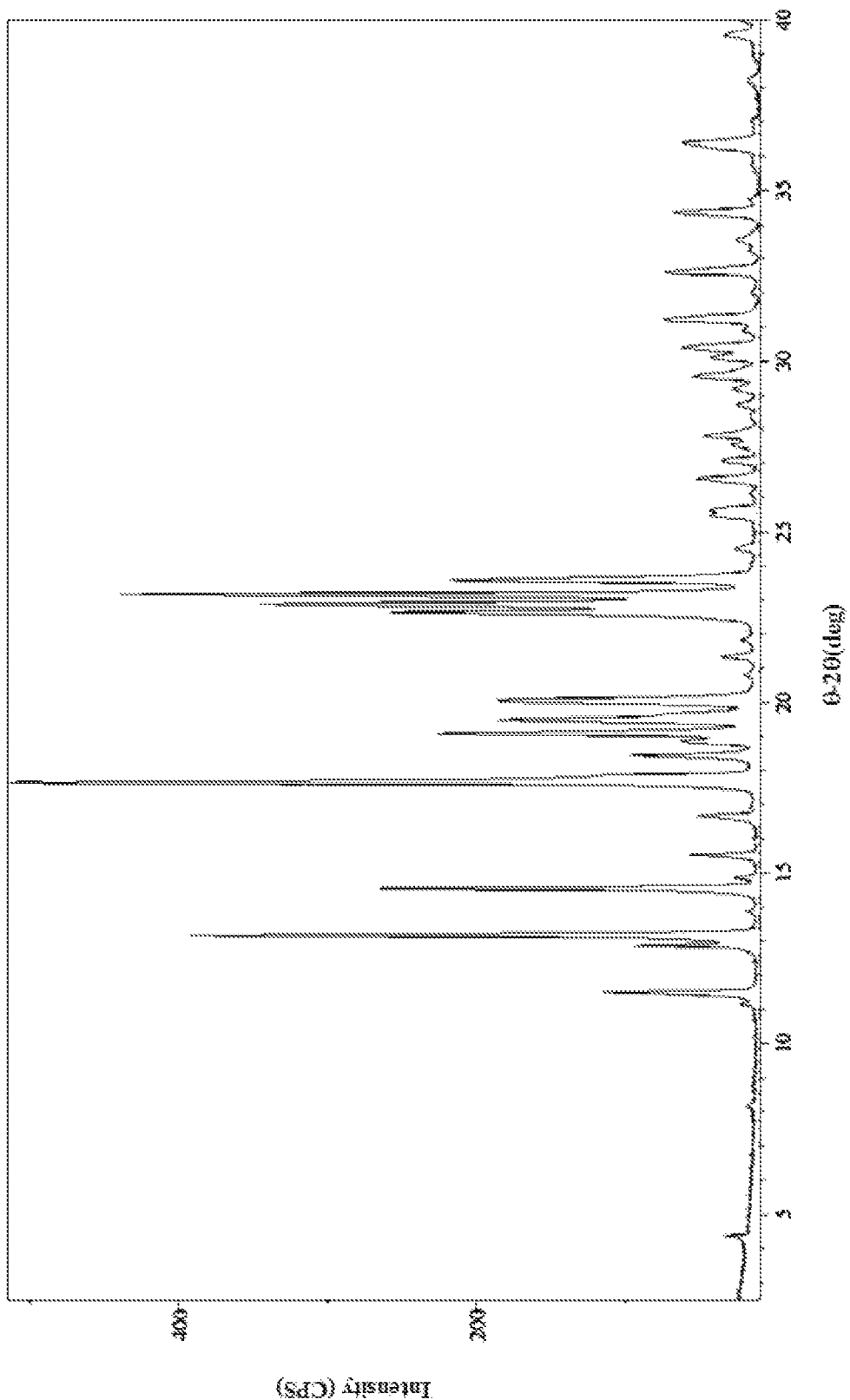
FIG. 19 is an X-ray powder diffraction pattern of Compound I Form L.

Compound I Form L is characterized by an X-ray powder diffractogram comprising peaks (±0.2°) at 13.18, 17.66, and 23.16 °2θ, as determined on a diffractometer using Cu—Kα radiation. The diffractogram comprises additional peaks (±0.2°) at 14.55 and 22.63 °2θ. Form L is also characterized by its full X-ray powder diffractogram as substantially shown in FIG. 19. Major peaks in the XRPD pattern are shown in Table 11 below. In one embodiment, this disclosure provides Compound I Form L comprising two or more peaks (±0.2°) listed in the Table 11 below as determined on a diffractometer using Cu—Kα radiation.

TABLE 11

Major Peaks in the XRPD Pattern for Compound I Form L

| °2θ (±0.2°) | d-space [Å] |
|---|---|
| 11.51 | 7.682 ± 0.133 |
| 12.88 | 6.865 ± 0.106 |
| 13.18 | 6.714 ± 0.101 |
| 14.55 | 6.082 ± 0.083 |
| 17.66 | 5.019 ± 0.056 |
| 18.44 | 4.807 ± 0.052 |
| 19.10 | 4.644 ± 0.048 |
| 19.47 | 4.555 ± 0.046 |
| 20.05 | 4.425 ± 0.044 |
| 22.63 | 3.927 ± 0.034 |
| 22.87 | 3.885 ± 0.034 |
| 23.16 | 3.837 ± 0.033 |
| 23.59 | 3.768 ± 0.031 |

Compound I Form L is characterized by an X-ray powder diffractogram comprising peaks (±0.2°) at 13.2, 17.7, and 23.2 °2θ, as determined on a diffractometer using Cu—Kα radiation. The diffractogram comprises additional peaks (±0.2°) at 14.6 and 22.6 °2θ. Form L is also characterized by its full X-ray powder diffractogram as substantially shown in FIG. 19. Major peaks in the XRPD pattern are shown in Table 11A below. In one embodiment, this disclosure provides Compound I Form L comprising two or more peaks (±0.2°) listed in the Table 11A below as determined on a diffractometer using Cu—Kα radiation.

TABLE 11A

Major Peaks in the XRPD Pattern for Compound I Form L

| °2θ (±0.2°) | d-space [Å] |
|---|---|
| 11.5 | 7.682 ± 0.133 |
| 12.9 | 6.865 ± 0.106 |
| 13.2 | 6.714 ± 0.101 |
| 14.6 | 6.082 ± 0.083 |
| 17.7 | 5.019 ± 0.056 |
| 18.4 | 4.807 ± 0.052 |
| 19.1 | 4.644 ± 0.048 |
| 19.5 | 4.555 ± 0.046 |
| 20.1 | 4.425 ± 0.044 |
| 22.6 | 3.927 ± 0.034 |
| 22.9 | 3.885 ± 0.034 |
| 23.2 | 3.837 ± 0.033 |
| 23.6 | 3.768 ± 0.031 |

Figure 20:
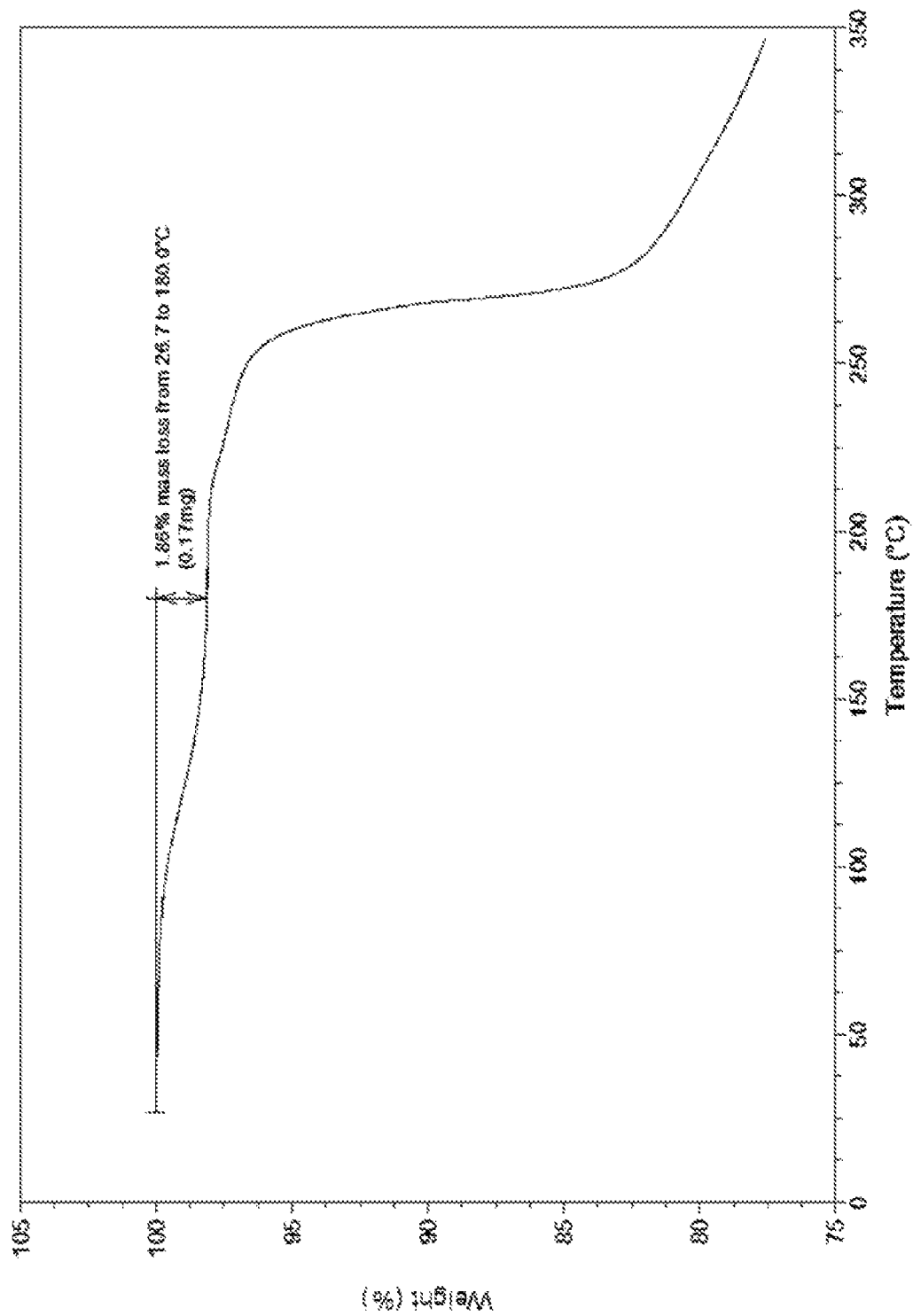
FIG. 20 is thermogravimetric analysis (TGA) of Compound I Form L.

In some embodiments, Form L is also characterized by thermogravimetric analysis (TGA) comprising a thermogram substantially as shown in FIG. 20.

Figure 21:
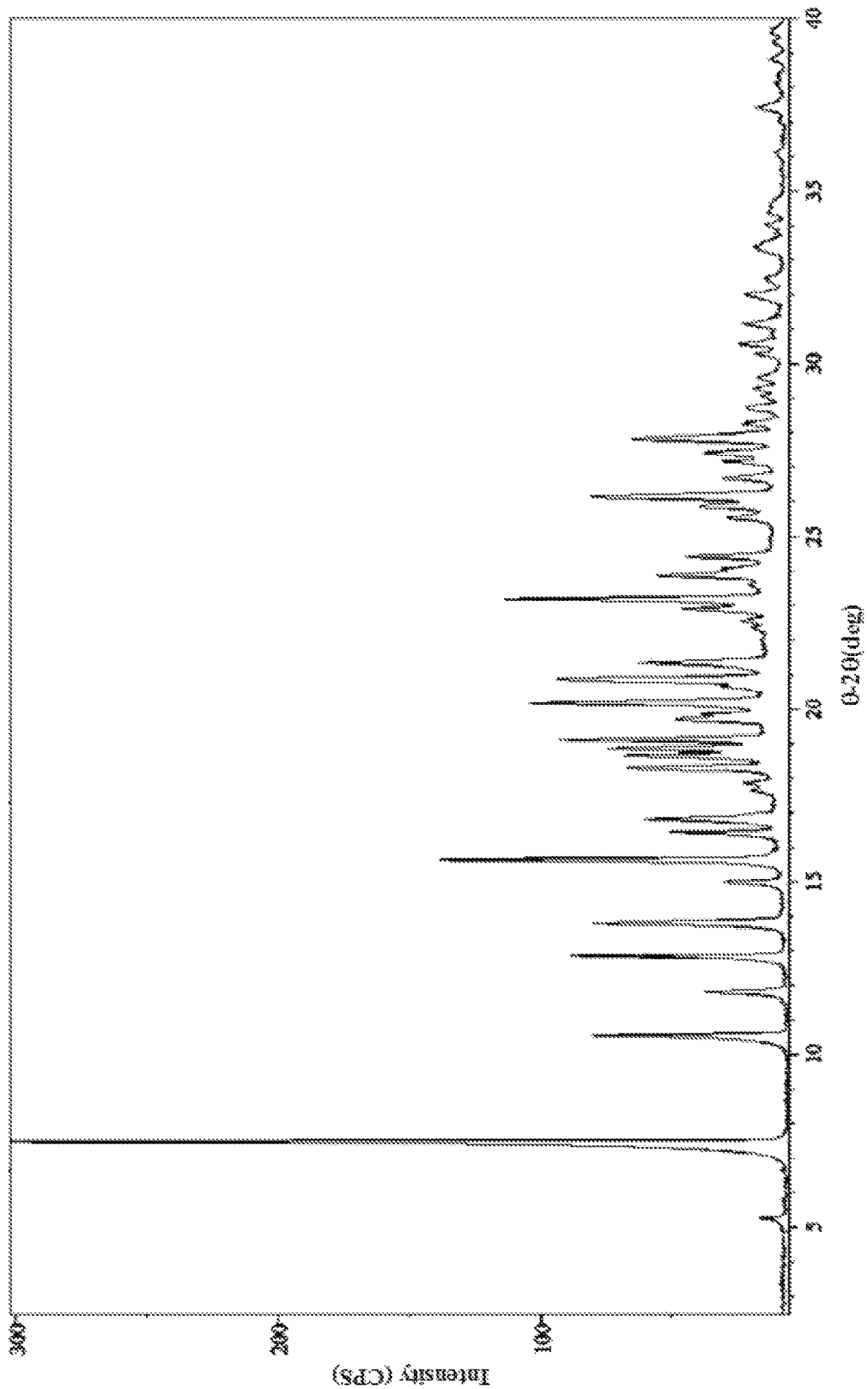
FIG. 21 is an X-ray powder diffraction pattern of Compound I Form M.

Compound I Form M is characterized by an X-ray powder diffractogram comprising peaks (±0.2°) at 7.47, 15.64, and 23.18 °2θ, as determined on a diffractometer using Cu—Kα radiation. The diffractogram comprises additional peaks (±0.2°) at 10.54 and 12.85 °2θ. Form M is also characterized by its full X-ray powder diffractogram as substantially shown in FIG. 21. Major peaks in the XRPD pattern are shown in Table 12 below. In one embodiment, this disclosure provides Compound I Form K comprising two or more peaks (±0.2°) listed in the Table 12 below as determined on a diffractometer using Cu—Kα radiation.

TABLE 12

Major Peaks in the XRPD Pattern for Compound I Form M

| °2θ (±0.2°) | d-space [Å] |
|---|---|
| 7.47 | 11.831 ± 0.316 |
| 10.54 | 8.390 ± 0.159 |
| 11.81 | 7.490 ± 0.126 |
| 12.85 | 6.883 ± 0.107 |
| 13.82 | 6.405 ± 0.092 |
| 15.64 | 5.661 ± 0.072 |
| 16.42 | 5.395 ± 0.065 |
| 16.82 | 5.266 ± 0.062 |
| 18.30 | 4.843 ± 0.052 |
| 18.64 | 4.755 ± 0.051 |
| 18.85 | 4.703 ± 0.049 |
| 19.11 | 4.640 ± 0.048 |
| 20.19 | 4.394 ± 0.043 |
| 20.86 | 4.256 ± 0.040 |
| 21.35 | 4.159 ± 0.039 |
| 22.89 | 3.882 ± 0.033 |
| 23.18 | 3.833 ± 0.033 |
| 23.87 | 3.725 ± 0.031 |
| 24.42 | 3.643 ± 0.029 |
| 25.87 | 3.441 ± 0.026 |
| 26.14 | 3.406 ± 0.026 |
| 27.83 | 3.204 ± 0.023 |

Compound I Form M is characterized by an X-ray powder diffractogram comprising peaks (±0.2°) at 7.5, 15.6, and 23.2 °2θ, as determined on a diffractometer using Cu—Kα radiation. The diffractogram comprises additional peaks (±0.2°) at 10.5 and 12.9 °2θ. Form M is also characterized by its full X-ray powder diffractogram as substantially shown in FIG. 21. Major peaks in the XRPD pattern are shown in Table 12A below. In one embodiment, this disclosure provides Compound I Form K comprising two or more peaks (±0.2°) listed in the Table 12A below as determined on a diffractometer using Cu—Kα radiation.

TABLE 12A

Major Peaks in the XRPD Pattern for Compound I Form M

| °2θ (±0.2°) | d-space [Å] |
|---|---|
| 7.5 | 11.831 ± 0.316 |
| 10.5 | 8.390 ± 0.159 |
| 11.8 | 7.490 ± 0.126 |
| 12.9 | 6.883 ± 0.107 |
| 13.8 | 6.405 ± 0.092 |
| 15.6 | 5.661 ± 0.072 |
| 16.4 | 5.395 ± 0.065 |
| 16.8 | 5.266 ± 0.062 |
| 18.3 | 4.843 ± 0.052 |
| 18.6 | 4.755 ± 0.051 |
| 18.9 | 4.703 ± 0.049 |
| 19.1 | 4.640 ± 0.048 |
| 20.2 | 4.394 ± 0.043 |
| 20.9 | 4.256 ± 0.040 |
| 21.4 | 4.159 ± 0.039 |
| 22.9 | 3.882 ± 0.033 |
| 23.2 | 3.833 ± 0.033 |
| 23.9 | 3.725 ± 0.031 |
| 24.4 | 3.643 ± 0.029 |
| 25.9 | 3.441 ± 0.026 |
| 26.1 | 3.406 ± 0.026 |
| 27.8 | 3.204 ± 0.023 |

Figure 22:
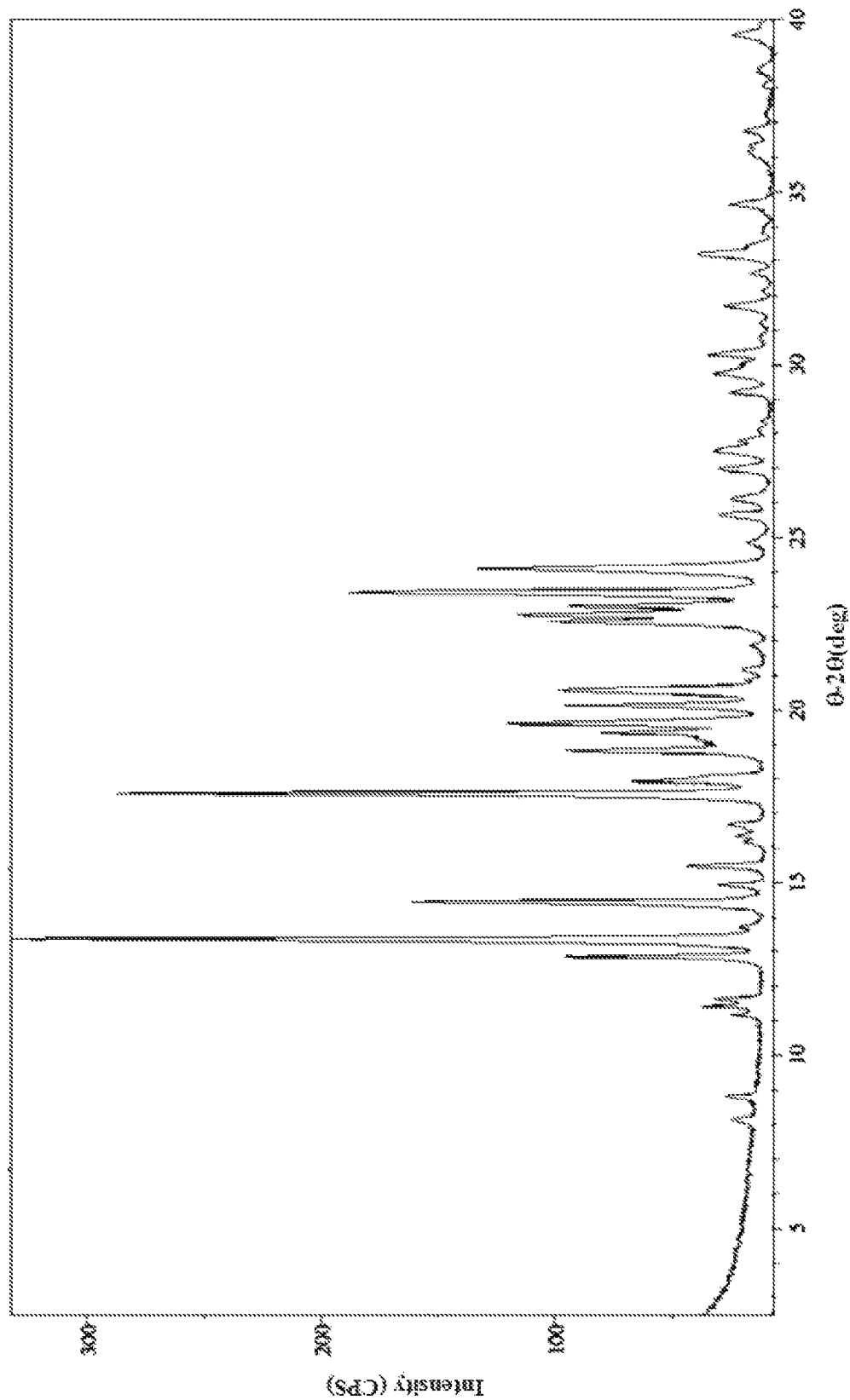
FIG. 22 is an X-ray powder diffraction pattern of Compound II Form N.

Compound II Form N is characterized by an X-ray powder diffractogram comprising peaks (±0.2°) at 13.37, 17.57 and 23.40 °2θ, as determined on a diffractometer using Cu—Kα radiation. The diffractogram comprises additional peaks (±0.2°) at 14.44 and 24.09 °2θ. Compound II Form N is also characterized by its full X-ray powder diffractogram as substantially shown in FIG. 22. Major peaks in the XRPD pattern are shown in Table 13 below. In one embodiment, this disclosure provides Compound II Form N comprising two or more peaks (±0.2°) listed in the Table 13 below as determined on a diffractometer using Cu—Kα radiation.

TABLE 13

Major Peaks in the XRPD Pattern for Compound II Form N

| °2θ (±0.2°) | d-space [Å] |
|---|---|
| 12.87 | 6.873 ± 0.106 |
| 13.37 | 6.619 ± 0.099 |
| 14.44 | 6.130 ± 0.084 |
| 15.49 | 5.715 ± 0.073 |
| 17.57 | 5.044 ± 0.057 |
| 17.94 | 4.940 ± 0.055 |
| 18.82 | 4.710 ± 0.050 |
| 19.34 | 4.586 ± 0.047 |
| 19.62 | 4.522 ± 0.046 |
| 20.13 | 4.407 ± 0.043 |
| 20.58 | 4.313 ± 0.041 |
| 22.55 | 3.940 ± 0.035 |
| 22.77 | 3.903 ± 0.034 |
| 23.01 | 3.862 ± 0.033 |
| 23.40 | 3.798 ± 0.032 |
| 24.09 | 3.691 ± 0.030 |

Compound II Form N is characterized by an X-ray powder diffractogram comprising peaks (±0.2°) at 13.4, 17.6 and 23.4 °2θ, as determined on a diffractometer using Cu—Kα radiation. The diffractogram comprises additional peaks (±0.2°) at 14.4 and 24.1 °2θ. Compound II Form N is also characterized by its full X-ray powder diffractogram as substantially shown in FIG. 22. Major peaks in the XRPD pattern are shown in Table 13A below. In one embodiment, this disclosure provides Compound II Form N comprising two or more peaks (±0.2°) listed in the Table 13A below as determined on a diffractometer using Cu—Kα radiation.

TABLE 13A

Major Peaks in the XRPD Pattern for Compound II Form N

| °2θ (±0.2°) | d-space [Å] |
|---|---|
| 12.9 | 6.873 ± 0.106 |
| 13.4 | 6.619 ± 0.099 |
| 14.4 | 6.130 ± 0.084 |
| 15.5 | 5.715 ± 0.073 |
| 17.6 | 5.044 ± 0.057 |
| 17.9 | 4.940 ± 0.055 |
| 18.8 | 4.710 ± 0.050 |
| 19.3 | 4.586 ± 0.047 |
| 19.6 | 4.522 ± 0.046 |
| 20.1 | 4.407 ± 0.043 |
| 20.6 | 4.313 ± 0.041 |
| 22.6 | 3.940 ± 0.035 |
| 22.8 | 3.903 ± 0.034 |
| 23.0 | 3.862 ± 0.033 |
| 23.4 | 3.798 ± 0.032 |
| 24.1 | 3.691 ± 0.030 |

Figure 23:
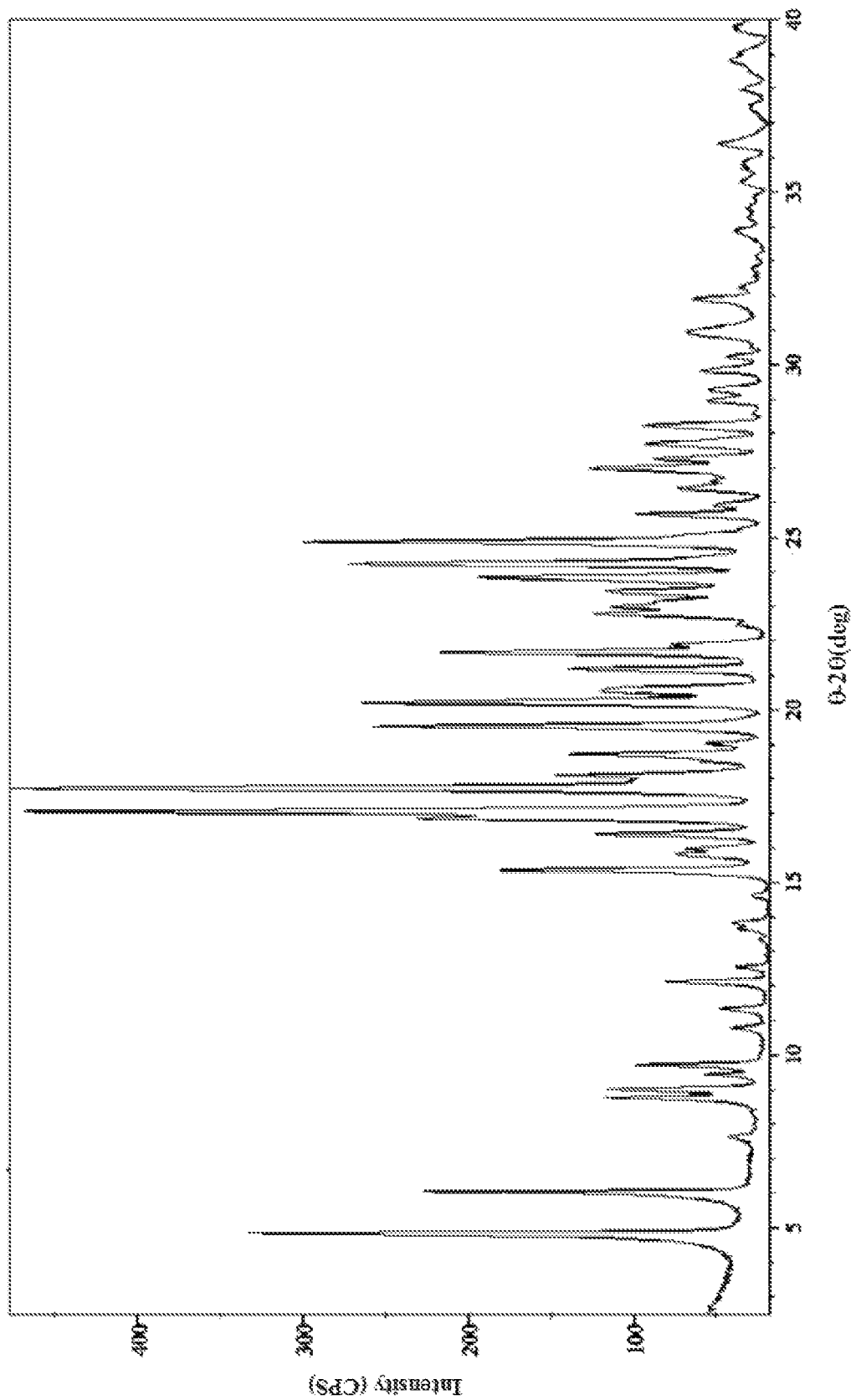
FIG. 23 is an X-ray powder diffraction pattern of Compound I Form O.

Compound I Form O is characterized by an X-ray powder diffractogram comprising peaks (±0.2°) at 4.84, 17.07, and 17.74 °2θ, as determined on a diffractometer using Cu—Kα radiation. The diffractogram comprises additional peaks (±0.2°) at 20.21 and 24.86 °2θ. Form O is also characterized by its full X-ray powder diffractogram as substantially shown in FIG. 23. Major peaks in the XRPD pattern are shown in Table 14 below. In one embodiment, this disclosure provides Compound I Form O comprising two or more peaks (±0.2°) listed in the Table 14 below as determined on a diffractometer using Cu—Kα radiation.

TABLE 14

Major Peaks in the XRPD Pattern for Compound I Form O

| °2θ (±0.2°) | d-space [Å] |
|---|---|
| 4.84 | 18.239 ± 0.753 |
| 6.04 | 14.612 ± 0.483 |
| 8.77 | 10.078 ± 0.229 |
| 9.01 | 9.804 ± 0.217 |
| 9.71 | 9.097 ± 0.187 |
| 12.12 | 7.294 ± 0.120 |
| 15.35 | 5.768 ± 0.075 |
| 16.40 | 5.399 ± 0.065 |
| 16.86 | 5.253 ± 0.062 |
| 17.07 | 5.192 ± 0.060 |
| 17.74 | 4.996 ± 0.056 |
| 18.10 | 4.896 ± 0.054 |
| 18.71 | 4.739 ± 0.050 |
| 19.53 | 4.543 ± 0.046 |
| 20.21 | 4.390 ± 0.043 |
| 20.55 | 4.319 ± 0.042 |
| 21.17 | 4.193 ± 0.039 |
| 21.67 | 4.098 ± 0.037 |
| 22.79 | 3.899 ± 0.034 |
| 22.99 | 3.865 ± 0.033 |
| 23.43 | 3.794 ± 0.032 |
| 23.83 | 3.731 ± 0.031 |
| 24.23 | 3.671 ± 0.030 |
| 24.86 | 3.578 ± 0.028 |

Compound I Form O is characterized by an X-ray powder diffractogram comprising peaks (±0.2°) at 4.8, 17.1, and 17.7 °2θ, as determined on a diffractometer using Cu—Kα radiation. The diffractogram comprises additional peaks (±0.2°) at 20.2 and 24.9 °2θ. Form O is also characterized by its full X-ray powder diffractogram as substantially shown in FIG. 23. Major peaks in the XRPD pattern are shown in Table 14A below. In one embodiment, this disclosure provides Compound I Form O comprising two or more peaks (±0.2°) listed in the Table 14A below as determined on a diffractometer using Cu—Kα radiation.

TABLE 14A

Major Peaks in the XRPD Pattern for Compound I Form O

| °2θ (±0.2°) | d-space [Å] |
|---|---|
| 4.8 | 18.239 ± 0.753 |
| 6.0 | 14.612 ± 0.483 |
| 8.8 | 10.078 ± 0.229 |
| 9.0 | 9.804 ± 0.217 |
| 9.7 | 9.097 ± 0.187 |
| 12.1 | 7.294 ± 0.120 |
| 15.4 | 5.768 ± 0.075 |
| 16.4 | 5.399 ± 0.065 |
| 16.9 | 5.253 ± 0.062 |
| 17.1 | 5.192 ± 0.060 |
| 17.7 | 4.996 ± 0.056 |
| 18.1 | 4.896 ± 0.054 |
| 18.7 | 4.739 ± 0.050 |
| 19.5 | 4.543 ± 0.046 |
| 20.2 | 4.390 ± 0.043 |
| 20.6 | 4.319 ± 0.042 |
| 21.2 | 4.193 ± 0.039 |
| 21.7 | 4.098 ± 0.037 |
| 22.8 | 3.899 ± 0.034 |
| 23.0 | 3.865 ± 0.033 |
| 23.4 | 3.794 ± 0.032 |
| 23.8 | 3.731 ± 0.031 |
| 24.2 | 3.671 ± 0.030 |
| 24.9 | 3.578 ± 0.028 |

Figure 24:
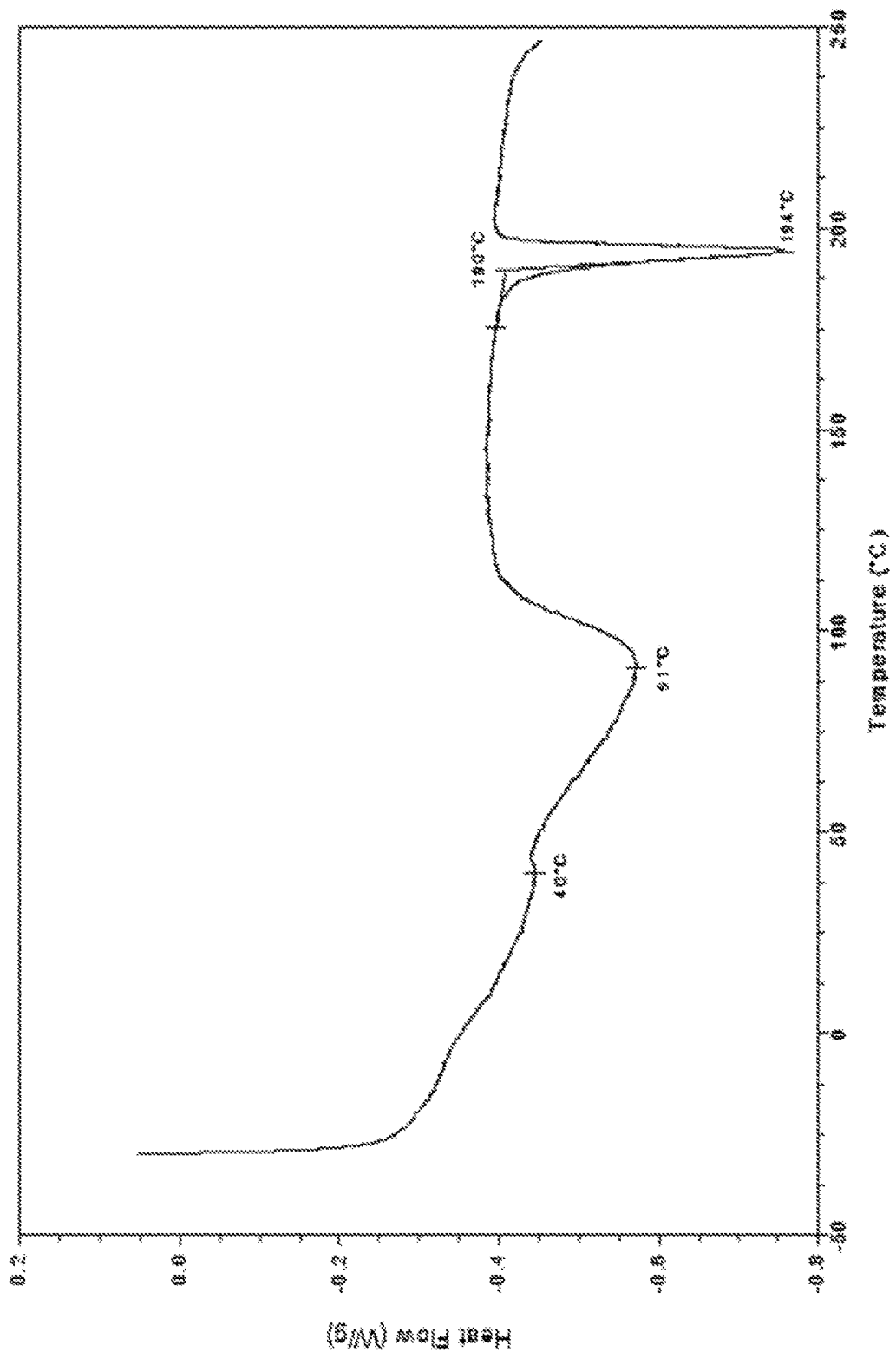
FIG. 24 is differential scanning calorimetry (DSC) curve of Compound I Form O.

In some embodiments, Form O is also characterized by its differential scanning calorimetry (DSC) curve comprising endotherms at about 40° C. and 91° C. In another embodiment, the DSC curve is substantially as shown in FIG. 24.

Figure 25:
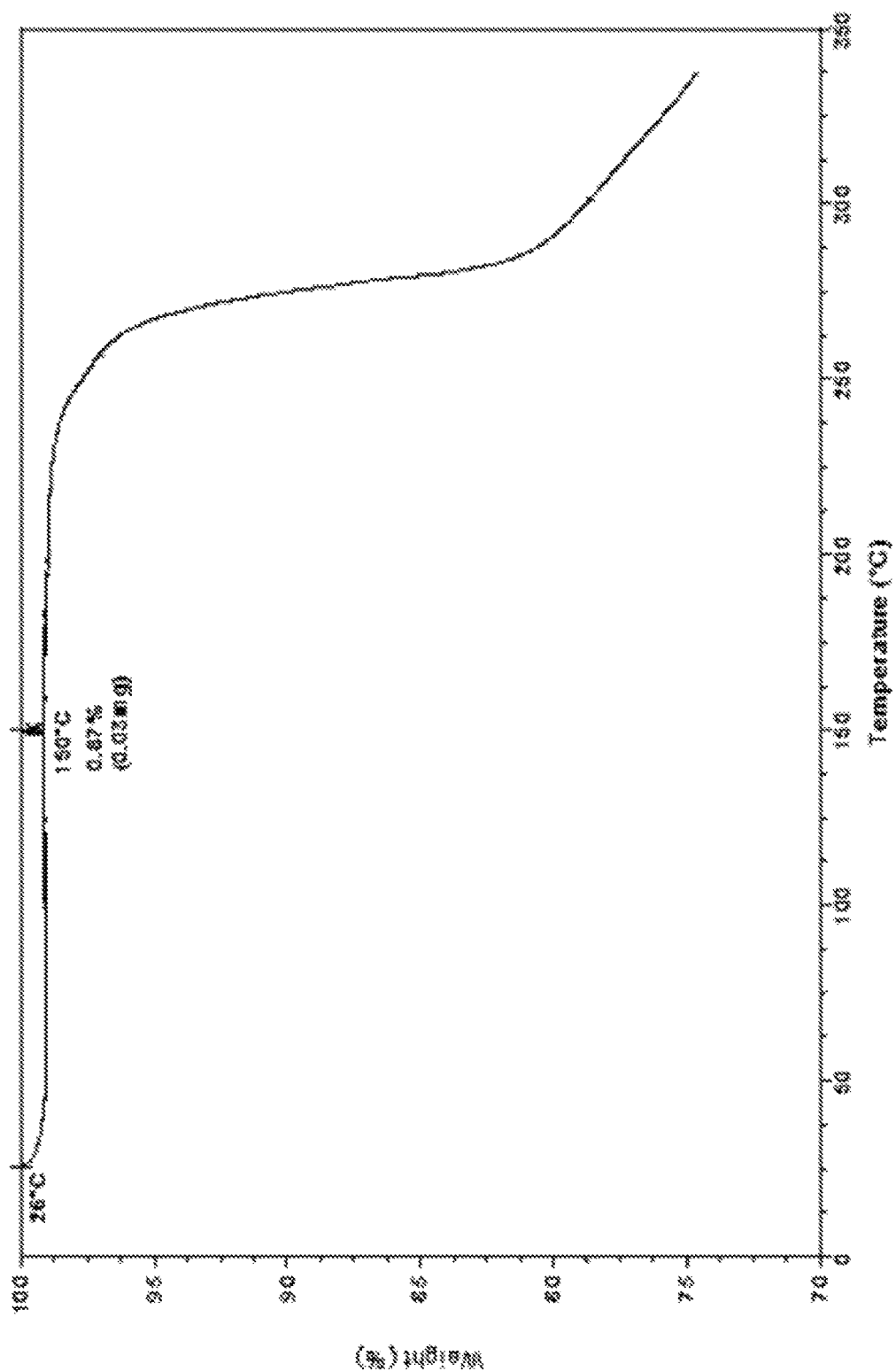
FIG. 25 is thermogravimetric analysis (TGA) of Compound I Form O.

In some embodiments, Form O is also characterized by thermogravimetric analysis (TGA) comprising a thermogram substantially as shown in FIG. 25.

Characterization of Crystalline Forms A, B and D-O of Compound I

All forms discussed below in Table 15 were obtained starting from Compound I, Form B that contained a trace amount of Compound I, Material C, an impurity. Compound I Form B was prepared as shown in the scheme above. Experiments were performed starting with this under kinetic and thermodynamic conditions using a wide range of solvents and solvent mixtures (see Table 15).

TABLE 15

Polymorph Screening Experiments
The starting material was Compound I Form B + trace
Compound I Material C for all the experiments in this table.

| Solvent (vol/vol) | Conditions[a] | Observations | XRPD Result |
|---|---|---|---|
| Acetone | VD of DCM, RT ~11 d | Aggregates, fine particles, B/E | Form A |
|  | SC from ~45 to 24° C., ~1 d | Aggregates, fiber like particles, B/E | Form H |
| ACN | CC from ~80° C. to ice bath, stirred in cold room, ~1 d | Aggregates, fine particles, B/E | Form L |
|  | SC from ~80 to 24° C., ~1 d | Aggregates, very fine particles, B/E | Form H |
|  | Seeded sol of API in ACN at ~70° C., SC from ~70 to 24° C., ~3 d | Agglomerates, fiber like particles, B/E | Form H |
| DCM | Slurry, RT, ~12 d | Aggregates, fine particles, B/E | Form A |
| Dioxane | SE at RT, ~4 d | Aggregates, acicular particles, B/E | Form F |
|  | FE, RT, ~3 min | Agglomerates, fine particles, B/E | Form E |
| Dioxane/DCM (1/5)[b] | S/AS, RT ~4 h, refrigerate ~1 d | Aggregates, fine particles, B/E | Form E |
| DMF | Dissolved ~40° C., sonicated, ~30 min Refrigerated, ~10 d w/FE intervals | Clear soln Agglomerates, fine particles, B/E |  |
| DMF/Water (50/50) $a_w = 0.6$ | Slurry, RT, ~15 d | Aggregates, fine particles, B/E | Form J |
| DMSO | CC from ~60° C. to ice bath Refrigerated, ~15 d, w/FE intervals | Clear soln Agglomerates, fine particles, B/E | Form M |
| EtOAc | SC from ~70 to 24° C., ~1 d Refrigerate ~1 d | Aggregates, fine needle particles, B/E | Form G |
| EtOAc/IPA (75/25) | Slurry, RT, ~13 d | Aggregates, very fine particles, B/E | Form G |
|  | Slurry, ~65° C., ~7 d | Aggregates, fine particles, B/E | Form B |
|  | CC from ~70° C. to ice bath, stirred in cold room, overnight | Aggregates, fine acicular particles, B/E | Form G |
|  | Slurry, RT, ~1 d | Aggregates, fine acicular particles, B/E | Form G |
| EtOH | Slurry, RT, ~14 d | Aggregates, very fine particles, B/E | Form B |
| EtOH/Water (75/25) $a_w = 0.8$ | Dissolved ~65° C., sonicated ~20 min | Aggregates, acicular particles, B/E | Form B |
| IPA | Slurry, RT, ~12 d | Aggregates, fine particles, B/E | Form B |
| MeOH | Slurry, RT, ~12 d | Aggregates, fine particles, B/E | Form B |
| MTBE | Slurry, RT, ~12 d | Aggregates, fine particles, B/E | Form B |
| THF | SE, RT, ~4 d | Agglomerates, plate like particles, B/E | Disordered |
|  | VD of MTBE, RT, ~11 d | Aggregates, acicular particles, B/E | Form D |
|  | FE, RT | Agglomerates, fine particles, B/E | Form D |
| THF/Heptane (1/1.5)[b] | S/AS, RT, ~1 d | Aggregates, very fine particles, B/E | Form D |
| THF/MTBE (1/6)[b] | S/AS, RT ~4 h, refrigerate, ~1 d | Aggregates, very fine particles, B/E | Form I |
| THF/Water (50/50) $a_w = 1.0$ | Slurry, RT, ~15 d | Aggregates, fine particles, B/E | Form D |

[a]Temperatures rounded to the nearest degree.
[b]Final ratio of solvents.

TABLE 16

Polymorph Screening Experiments
Different starting materials were used as indicated
in the footnotes of this table.

| Solvent (vol/vol) | Conditions[a] | Observations | XRPD Result |
|---|---|---|---|
| Water (Form G)[b] | Slurry, RT, ~3 d | Aggregates, very fine particles, B/E | Form H + Form K |
| Water (Form A)[c] | Slurry, RT, ~2 d | Aggregates, fine particles, B/E | Form A + Form H |
| Water (Form G)[b] | Slurry, ~30° C., ~2 d | Agglomerates, very fine particles, B/E | Form H |
| Water (Form G)[b] | Slurry, RT, ~3 h | Aggregates, fine particles, B/E | Form H + Form K |

[a]Temperatures rounded to the nearest degree.
[b]Starting material was Material G Compound I Form A As shown in Table 15, Form A was obtained as an unmixed sample from two experiments, vapor diffusion of dichloromethane into an acetone solution, and a two-week slurry in dichloromethane at ambient temperature. Form A was slurried in water at ambient temperature in an attempt to generate hydrated solids. The resulting sample was characterized by XRPD as a mixture of Form A and Form H. Thermal analysis of Form A showed a 6.9 wt % loss between 25° C. and 210° C. which corresponds to approximately 0.5 mole dichloromethane Data overall are consistent with Form A being a hemi-dichloromethane solvate.

Compound I Form B

Form B as a mixture with a trace amount of Material C was used as a starting material for experiments listed in Table 15. Also, several experiments resulted in pure Form B. A number of interconversion experiments were done using Form B and Form H as input materials at various temperatures and in solvents that did not produce solvates.

TABLE 17

Interconversion Experiments

| Input Materials | Conditions[a] (vol/vol) | Observations | XRPD Result |
|---|---|---|---|
| Form B, Form H | EtOH/water (75/25), ~65° C., ~4 d $a_w$ ~0.76[b] | Aggregates, fine particles, B/E | Form H |
| Form B, Form H | ACN, ~65° C., ~4 d | Agglomerates, very fine particles, B/E | Form H |
| Form B, Form H | Acetone, RT, ~4 d | Aggregates, fine particles, B/E | Form H |
| Form B, Form H | ACN, RT, ~4 d | Aggregates, fine particles, w/B/E | Form H |
| Form B, Form H | EtOH/water (75/25), RT, ~4 d $a_w$ ~0.76[b] | Aggregates, fine particles, B/E | Form H |
| Form B, Form H | 2-BuOH, ~75° C. ~4 d | Aggregates, fine particles, B/E | Form H |

[a]Solvents were pre-saturated with Compound I Form B + trace Compound I Material C prior to the addition of input materials.
[b]Water activities were calculated using UNIFAC calculator (v. 3.0) at 25° C.

All experiments resulted in Form H. While solid form screening results overall show that Form B is a stable anhydrous form of Compound I which can be obtained from a variety of conditions, competitive slurry results indicate that Form B is less stable than Form H within the temperature range evaluated, between ambient temperature and approximately 75° C.

Also, solubility was calculated Form B as a mixture with a trace amount of Material C and the results are shown in Table 18 below.

TABLE 18

Solubility Estimates of Compound
I Form B at Ambient Temperature

| Solvent (vol/vol) | Solubility (mg/mL)[a] |
|---|---|
| Acetone | ~36 |
| ACN | ~5 |
| t-BuOH | <2 |
| DCM | <1 |
| DMF | >97 |
| DMSO | >84 |
| Dioxane | >103 |
| EtOAc | ~5 |
| EtOH | ~1 |
| Heptane | <1 |
| IPA | <1 |
| MeOH | ~4 |
| MTBE | <2 |
| THF | >102 |
| Water | <1 |
| EtOH/Water (75/25) | ~5 |

[a] Solubilities are calculated based on the total solvent used to give a solution. Actual solubilities may be greater because of the volume of the solvent portions or a slow rate of dissolution. Solubilities are rounded to the nearest mg/mL unless otherwise stated.

Compound I Material C

Material C was present in a trace amount of the polymorph screen starting material, Material C appears to be an impurity originating from the synthetic process used to prepare the starting material. Additionally, the observation that Material C was not obtained in any polymorph screening experiments except for one in which the starting material was exposed to 75% RH, at about 40° C. for a period of time supports the impurity assumption. The relative amount of material C in the XRPD pattern did not change from the starting material. Other observations supporting the impurity hypothesis was the result from the pseudo-interconversion slurry between the R and S-enantiomers such that Form B was generated.

Compound I Form D

Form D was obtained from experiments involving THF, both under kinetic and thermodynamic conditions. Thermal analysis of one sample showed a 10.8 wt % loss from 26 to 115° C. which is equivalent to approximately 1 mole of THF. Data overall are consistent with Form D being a THF solvate.

Compound I Form E

Form E was obtained from experiments involving dioxane under kinetic conditions. Antisolvent addition of dichloromethane to a dioxane solution and fast evaporation of a dioxane solution gave Form E by XRPD. Thermal analysis of the sample prepared by fast evaporation showed an initial 3 wt % loss from 27 to 80° C. followed by a 10 wt % loss from 80 to 125.0° C. that is equivalent to approximately 0.7 mole dioxane. Data overall are consistent with Form E being a dioxane solvate of unknown stoichiometry.

Compound I Form F

Form F was obtained from one experiment only, a slow evaporation of a dioxane solution. It was characterized by XRPD.

Compound I Form G

Form G was obtained from several experiments involving ethyl acetate under both thermodynamic and kinetic conditions. Thermal analysis and solution proton NMR spectroscopy were performed on a sample prepared by slow cooling a supersaturated solution in ethyl acetate Thermal analysis showed a 14 wt % loss from 27 to 135° C. that is equivalent to 1 mole of ethyl acetate. This stoichiometry was further confirmed by NMR.

Drying Form G at approximately 60° C. under vacuum for 3 days resulted in a mixture of Form B with a minor amount of Form G. Drying under milder conditions under vacuum at ambient temperature for approximately six hours resulted in unchanged Form G. Slurrying a sample of Form G in water at ambient temperature for one day generated a mixture of Form H and Form K. Data overall are consistent with Form G being an ethyl acetate solvate.

Compound I Form H

Form H was obtained from slow cools of solutions in acetone and acetonitrile from elevated temperatures (approximately 45 and 80° C., respectively). Form H was also obtained as mixtures. Slurrying of Form G in water at ambient temperature for one day gave a mixture of Form H with Form K. A slurry of Form A in water at ambient temperature for approximately two days resulted in a mixture of Form H with Form A. The XRPD pattern of Form H was successfully indexed indicating that it is composed primarily of a single phase and consistent with an anhydrous form of Compound I exhibiting a greater density compared to Form B, 1.510 versus 1.416 g/cm$^3$. Thermal analysis of a sample of Form H showed a minimal weight loss of 0.1 wt % between 27 and 175° C. and a broad endotherm with a peak onset at 233° C. and a peak maximum at 239° C. that was followed immediately by a decomposition exotherm. The NMR spectrum was consistent with the Compound I structure and the presence of water, likely present in the DMSO-d6 solvent.

Data overall are consistent with Form H being an anhydrous form of Compound I, and polymorph of Form B. Competitive slurry experiments conducted in various solvent systems and temperatures indicate that Form H is more stable than Form B within the temperature range evaluated, between ambient temperature and approximately 75° C.

Compound I Form I

Form I was produced from one experiment only, from MTBE antisolvent addition to a solution in THF at ambient temperature. The resulting slurry was placed in the refrigerator for a day before isolating the solids and analyzing by XRPD. Thermal analysis showed 7.8 wt % loss between 25° C. and 125° C. that corresponds to approximately 0.6 mol THF or 0.5 mol MTBE (or a combination of the two solvents). Data overall are consistent with Form I being solvated, containing THF, MTBE, or a mixture of the two solvents.

Compound I Form J

Form J was obtained from all experiments that involved DMF. A solution that was held in the refrigerator with intermittent fast evaporations over 10 days and a 15-day slurry in DMF/water (50/50, vol/vol) both gave Form J. The solids were not further characterized. It is possible that Form J is a DMF solvate.

Compound I Form K

Form K was obtained as mixtures only from experiments starting with Form G (ethyl acetate solvate). Slurrying a sample of Form G in water at ambient temperature for three days produced a mixture of Form H and Form K. By drying a sample of Form G under vacuum at 60° C. for approximately 3 days, Form B with a minor amount of Form K was generated. The sample of Form H and Form K was further analyzed by TGA. The thermogram contains an initial loss of 0.7 wt % between 25 and 60° C. with no further weight loss prior to decomposition. As Form H is anhydrous, it is possible that the weight loss was due to residual surface solvent from the sample or to solvent loss (water or ethyl acetate) from Form K. Several attempts were made to obtain samples enriched with Form K, specifically slurrying of Form G in water over different periods of time. The experiments yielded another mixture of Form K with Form H (3 hour slurry, ambient temperature), a mixture of Form A with Form H (2 day slurry at ambient temperature), or pure Form H (2 day slurry at approximately 30° C.).

Compound I Form L

Form L was obtained from a crash cooling experiment of a solution in acetonitrile which was then stirred at 2 to 8° C. for one day. Thermal analysis showed 1.9 wt % loss between 27° C. and 180° C. that corresponds to approximately 0.3 mol acetonitrile. Data overall are consistent with Form L being an acetonitrile solvate of unknown stoichiometry.

Compound I Form M

Form M was produced from a crash cool of a solution in DMSO from approximately 60° C. followed by refrigeration with intermittent fast evaporation intervals. The solids were characterized by XRPD. Form J is suspected to be a DMSO solvate of Compound I.

Compound II Form N

Compound II was synthesized using the 3-S-fluropyrrolidine HCl salt in Step 5 of the synthetic scheme shown above for Compound I. Compound II can also be synthesized by making the racemic mixture of I and II and by separating out the S-enantiomer.

Compound I Form O

Form O was produced from a mixture of Compound I Form B and Compound I Form O and 15 mL of a 98:2 (v:v) water/ethanol solvent system. The sample was slurried for 8 days, at ambient temperature, prior to harvesting by vacuum filtration to provide Compound I Form O. The XRPD pattern of Form O indicates that the sample is composed primarily of a single crystalline phase. Karl Fischer titration indicated the sample contained approximately 1.7% water, consistent with possibly a hemi-hydrate. This value was higher than the TGA weight loss; however, the TGA weight loss occurred from the beginning of the analysis and may therefore have started during the initial equilibration prior to data collection. Upon drying the starting material, the solids remained as a mixture of Form B and Form O. However, compared to Form O in the starting material, shifts of peak to higher angles were observed in the XRPD pattern of the dried sample. This suggests the contraction of the crystal lattice, and is consistent with dehydration of Form O. Based on this study, Form O is a hemi-hydrate or a variable hydrate.

Compositions

In one embodiment, this disclosure provides a composition comprising two or more compounds selected from the group consisting of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M and Compound I Form O as described herein.

In another embodiment, the composition comprises Compound I Form A and Compound I Form H. In another embodiment, the composition comprises Compound I Form A and at least 10%, 15%, 20%, 25%, 30%, 35%, 40%, 45%, 50%, 55%, 60%, 65%, 70%, 75%, 80%, 85%, 90%, or 95% w/w of Compound I Form H. In yet another embodiment, the composition comprises Compound I Form A and at least 50% of w/w of Compound I Form H.

In another embodiment, the composition comprises Compound I Form H and Compound I Form K. In another embodiment, the composition comprises Compound I Form H and at least 10%, 15%, 20%, 25%, 30%, 35%, 40%, 45%, 50%, 55%, 60%, 65%, 70%, 75%, 80%, 85%, 90%, or 95% w/w of Compound I Form K. In yet another embodiment, the composition comprises Compound I Form H and at least 50% w/w of Compound I Form K.

Another embodiment is directed to a composition comprising Compound I Form B or Compound I Form H. In one embodiment, the composition comprises at least 50% w/w of Compound I Form B. In another embodiment, the composition comprises at least 50% w/w of Compound I Form H.

Another embodiment is directed to a composition comprising Compound I Form B or Compound I Form H or Compound II Form N. In one embodiment, the composition comprises at least about 50% w/w, at least about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound I Form B. In another embodiment, the composition comprises at least about 50% w/w, about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound I Form H. In another embodiment, the composition comprises at least about 50% w/w, at least about 60% w/w, at least about 70% w/w, at least about 80% w/w, at least about 90% w/w, at least about 92% w/w, at least about 94% w/w, at least about 96% w/w, at least about 98% w/w, at least about 99% w/w, at least about 99.5% w/w or at least 99.9% w/w of Compound II Form N.

Another embodiment is directed to a composition comprising Compound I Form B and Compound I Form C. In one embodiment, the composition comprises at least about 50% w/w, at least about 60% w/w, at least about 70% w/w, at least about 80% w/w, at least about 85% w/w, at least about 90% wt/wt, at least about 95% w/w, at least about 97% w/w, at least about 99% w/w, or at least about 99.9% w/w of Compound I Form B. In another embodiment, the composition comprises traces of Compound I Form C.

In another embodiment, this disclosure provides Compound I Form B, Compound I Form H or Compound II Form N, wherein said forms are pure. The term "pure" means said form is having at least 50% w/w purity, at least 60% w/w purity, at least 70% w/w purity, at least 80% w/w/ purity, at least 85% w/w/ purity, at least 90% w/w purity, at least 92% w/w purity, at least 94% w/w purity, at least 96% w/w purity, at least 98% w/w purity, at least 99% w/w purity, at least 99.5% w/w purity or at least 99.9% w/w purity.

Formulations and Administration

In another aspect, the present disclosure provides pharmaceutical compositions comprising/including a pharmaceutically acceptable carrier or excipient and a Compound I form as described herein or a pharmaceutically acceptable salt thereof. In an exemplary embodiment, the present disclosure provides a pharmaceutical formulation comprising Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N, or Compound I Form O as described herein.

The methods and the forms will typically be used in therapy for human subjects. However, they may also be used to treat similar or identical indications in other animal subjects. The solid, crystalline or polymorphs of Compound I or Compound II described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: The Science and Practice of Pharmacy, 21st edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a solid, crystalline or polymorph of Compound I or Compound II of the disclosure (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discrete units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening agent such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the solid, crystalline or polymorph of Compound I or Compound II.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of the solid, crystalline or polymorphs of Compound I or Compound II as described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than C12). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, the solid, crystalline or polymorphs of Compound I or Compound II as described herein are administered as inhalants. Compound I or Compound II forms described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose may be in the range of about 0.01 to 50 mg/kg, also about 0.1 to 20 mg/kg of the subject being treated. Multiple doses may be used.

The solid, crystalline or polymorph of Compound I or Compound II as described herein may also be used in combination with other therapies for treating the same disease. Such combination use includes administration of the compounds and one or more other therapeutics at different times, or co-administration of the compound and one or more other therapies. In some embodiments, dosage may be modified for one or more forms of the Compound I or Compound II or other therapeutics used in combination, e.g., reduction in the amount dosed relative to a compound or therapy used alone, by methods well known to those of ordinary skill in the art.

As discussed further in the "Combination Therapy" section, it is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present disclosure provides for delivery of a compound I or Compound II form as described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

Kinase Targets and Indications

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present disclosure are described in the art, including, without limitation, protein kinases as described in U.S. Pat. No. 7,863,288 (see also, PCT publication WO2007/002433), the disclosure of which is hereby incorporated by reference as it relates to such kinase targets, as well as the following.

p A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

Many cancers associated with dysregulation of the RAS-RAF-ERK pathway, such as cancers having B-Raf V600, such as V600E mutations or NRAS mutations, may be treated with Raf kinase inhibitors, such as the Pan Raf kinase inhibitors as described herein. The ability of these compounds to inhibit multiple Raf kinase targets, including c-Raf-1, B-Raf, and B-Raf V600, such as V600E, provides additional benefits for inhibiting activating mutations in this pathway, with such cancers less likely to develop resistance to such inhibitors as they are targeting several points in the pathway. Pan Raf kinase inhibitors as described herein may be useful in treating a variety of cancers, including, but not limited to, melanoma, glioma, glioblastoma mulitforme, pilocytic astrocytoma, carcinoma (e.g. gastrointestinal, liver, biliary tract, bile duct (cholangiocarcinoma), colorectal, lung, brain, bladder, gallbladder, breast, pancreatic, thyroid, kidney, ovarian, adrenocortical, prostate), gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. See McDermott et al., PNAS, 2007, 104(50): 19936-19941; and Jaiswal et al., PLoS One, 2009, 4(5):e5717.

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). c-Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

Raf inhibitors (A-Raf and/or B-Raf and/or c-Raf-1) may be useful in treating A-Raf-mediated, B-Raf-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, brain, bladder, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, chronic myelomonocytic leukemia, childhood, acute lymphoblastic leukemia, plasma cell leukemia, multiple myeloma, tumor angiogenesis, gastrointestinal stromal tumors, neuroendocrine tumors such as medullary thyroid cancer, carcinoid, small cell lung cancer, Kaposi's sarcoma and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to Helicobacter pylori, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Erk2: Target kinase Erk2 (i.e., extracellular signal-regulated kinase 2) is a 41.4 kDa dual function serine/threonine-tyrosine kinase encoded by chromosome 22q11.2 (symbol: MAPK1). Erk2 is a member of the mitogen-activated protein (MAP) kinase family and is alternatively known as mitogen-activated protein kinase 1 (i.e., MAPK1). MAP kinases act as an integration point for multiple biochemical signals, and are involved in a wide variety of cellular processes such as proliferation, differentiation, transcription regulation and development.

The activation of Erk2 requires phosphorylation by upstream kinases. Upon activation, Erk2 translocates to the nucleus of the stimulated cells, where it phosphorylates nuclear targets, in addition to other targets including microtubule associated protein 2, myelin basic protein and ELK1. MacKenzie et al. state that the cAMP-specific phosphodiesterase family 4, subfamily D, isoform 3 (i.e., PDE4D3) is shown to have FQF (i.e., Phe-Gln-Phe) and KIM (i.e., Kinase Interaction Motif) docking sites for Erk2. These sites straddle the Ser(579) target residue for Erk2 phosphorylation of PDE4D3. Mutation of either or both of these docking sites prevent Erk2 from being co-immunoprecipitated with PDE4D3, ablate the ability of epidermal growth factor (EGF) to inhibit PDE4D3 through Erk2 action in transfected COS cells, and attenuate the ability of Erk2 to phosphorylate PDE4D3 in vitro. The two conserved NH(2)-terminal blocks of sequence, called upstream conserved regions 1 and 2 (i.e., UCR1 and UCR2), that characterize PDE4 long isoforms, are proposed to amplify the small, inherent inhibitory effect that Erk2 phosphorylation exerts on the PDE4D catalytic unit. In contrast to this, the lone intact UCR2 region found in PDE4D1 directs COOH-terminal Erk2 phosphorylation to cause the activation of this short isoform. From the analysis of PDE4D3 truncates, it is suggested that UCR1 and UCR2 provide a regulatory signal integration module that serves to orchestrate the functional consequences of Erk2 phosphorylation. The PDE4D gene thus encodes a series of isoenzymes that are either inhibited or activated by Erk2 phosphorylation and thereby offers the potential for ERK2 activation either to increase or decrease cAMP levels in cellular compartments (MacKenzie et al., J Biol Chem 2000, 275(22):16609-17).

According to OMIM, Pleschka et al. (Nature Cell Biol., 2001, 3: 301-305) proposed that Erk2 regulates a cellular factor involved in the viral nuclear export protein function. They suggested that local application of MEK inhibitors may have only minor toxic effects on the host while inhibiting viral replication without giving rise to drug-resistant virus variants (OMIM MIM Number: 176948: Oct. 27, 2005). Erk2 is involved in cytokine signaling and is a target for treating inflammation. Ramesh and Philipp state that lipoproteins are the key inflammatory molecule type of *Borrelia burgdorferi*, the spirochete that causes Lyme disease. They investigated whether specific inhibition of p38 and Erk1/2 MAPK would inhibit TNF-alpha and IL-6 production and thus astrocyte apoptosis, and proliferation, respectively. Lipoprotein-stimulated IL-6 production was unaffected by the MAPK inhibitors. In contrast, inhibition of both p38 and Erk1/2 significantly diminished TNF-alpha production, and totally abrogated production of this cytokine when both MAPK pathways were inhibited simultaneously. MAPK inhibition thus may be considered as a strategy to control inflammation and apoptosis in Lyme neuroborreliosis (Ramesh and Philipp, Neurosci Lett 2005, 384(1-2):112-6). The role of Erk2 in signaling of cell differentiation, proliferation and survival suggests that inhibition of Erk2 may be therapeutic for several types of cancer. Husain et al. studied the effect of NSAIDs on MAPK activity and phosphorylation in gastric cancer. They conclude that NS-398 (a selective COX-2 inhibitor) and indomethacin (a non-selective NSAID) significantly inhibit proliferation and growth of human gastric cancer cell line MKN28. This effect is mediated by NSAID-induced inhibition of MAPK (ERK2) kinase signaling pathway, essential for cell proliferation (Husain et al., Life Sci 2001, 69(25-6):3045-54). Erk2 inhibitors may be useful in treating cancer, including gastric cancer, and in treating inflammation, including control of inflammation and apoptosis in Lyme neuroborreliosis.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

In certain embodiments, one or more solid, crystalline or polymorphs of Compound I as disclosed herein are active in an assay measuring B-Raf protein kinase activity. It has an $IC_{50}$ less than 0.1 µM as determined in a generally accepted B-Raf kinase activity assay and in a generally accepted mutant B-Raf kinase (such as V600A, V600M, V600R, V600E, V600K or V600G) activity assay. In some embodiments the assay for measuring B-Raf kinase activity and/or mutant B-Raf kinase (such as V600A, V600M, V600R, V600E, V600K or V600G) activity includes an assay (e.g., biochemical or cell-bases assays) such as described in U.S. Pub. No. 2014/0128373.

Methods for Treating Conditions Mediated by Kinases

In another aspect, the present disclosure provides a method for treating a subject suffering from or at risk of a protein kinase mediated diseases or conditions. The method includes administering to the subject an effective amount of a compound of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M or Compound I Form O as described herein, or a composition thereof or a pharmaceutically acceptable salt thereof. In certain embodiments, the method involves administering to the subject an effective amount of any one or more solid, crystalline or polymorphs of Compound I or Compound II as described herein in combination with one or more other therapies for the disease or condition.

In some embodiments, the diseases or conditions treatable with the compounds of the present disclosure include, but are not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In other embodiments, the diseases or condictions treatable with the compounds of the present disclosure include, but are not limited to, ischemic stroke, cerebrovascular ischemia, multi-infarct dementia, head injury, spinal cord injury, Alzheimer's disease, Parkinson's disease, amyotrophic lateral sclerosis, dementia, senile chorea, Huntington's disease, neoplastic disease, complications with neoplastic disease, chemotherapy-induced hypoxia, gastrointestinal stromal tumors, prostate tumors, mast cell tumors, canine mast cell tumors, acute myeloid leukemia, acute lymphocytic leukemia, chronic myeloid leukemia, chronic lymphocytic leukemia, multiple myeloma, melanoma, mastocytosis, glioma, glioblastoma, astrocytoma, neuroblastoma, sarcomas, sarcomas of neuroectodermal origin, leiomyosarcoma, lung carcinoma, breast carcinoma, pancreatic carcinoma, colon carcinoma, hepatocellular carcinoma, renal carcinoma, carcinoma of the female genital tract, squamous cell carcinoma, carcinoma in situ, lymphoma, histiocytic lymphoma, non-Hodgkin's lymphoma, MEN2 syndromes, neurofibromatosis, Schwann cell neoplasia, myelodysplastic syndrome, leukemia, tumor angiogenesis, thyroid cancer, liver cancer, bone cancer, skin cancer, brain cancer, cancer of the central nervous system, pancreatic cancer, lung cancer, small cell lung cancer, non small cell lung cancer, breast cancer, colon cancer, bladder cancer, prostate cancer, gastrointestinal tract cancer, cancer of the endometrium, fallopian tube cancer, testicular cancer, ovarian cancer, pain of neuropathic origin, pain of inflammatory origin, acute pain, chronic pain, migraine, cardiovascular disease, heart failure, cardiac hypertrophy, thrombosis, thrombotic microangiopathy syndromes, atherosclerosis, reperfusion injury, ischemia, cerebrovascular ischemia, liver ischemia, inflammation, polycystic kidney disease, age-related macular degeneration, rheumatoid arthritis, allergic rhinitis, inflammatory bowel disease, ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, dermal scarring, tissue scarring, vascular restenosis, fibrotic disorders, hypereosinophilia, CNS inflammation, pancreatitis, nephritis, atopic dermatitis, hepatitis, immunodeficiency diseases, severe combined immunodeficiency, organ transplant rejection, graft versus host disease, renal disease, prostatic disease, diabetic nephropathy, nephrosclerosis, glomerulonephritis, interstitial nephritis, Lupus nephritis, prostate hyperplasia, chronic renal failure, tubular necrosis, diabetes-associated renal complication, associated renal hypertrophy, type 1 diabetes, type 2 diabetes, metabolic syndrome, obesity, hepatic steatosis, insulin resistance, hyperglycemia, lipolysis obesity, infection, *Helicobacter pylori* infection, Influenza virus infection, fever, sepsis, pulmonary diseases, chronic obstructive pulmonary disease, acute respiratory distress syndrome, asthma, allergy, bronchitis, emphysema, pulmonary fibrosis, genetic developmental diseases, Noonan's syndrome, Crouzon syndrome, acrocephalo-syndactyly type I, Pfeiffer's syndrome, Jackson-Weiss syndrome, Costello syndrome, faciocutaneoskeletal syndrome, leopard syndrome, cardio-faciocutaneous syndrome, neural crest syndrome abnormalities causing cardiovascular, skeletal, intestinal, skin, hair or endocrine diseases, disorders of bone structure or mineralization, osteoporosis, increased risk of fracture, hypercalcemia, bone metastases, Grave's disease, Hirschsprung's disease, lymphoedema, selective T-cell defect, X-linked agammaglobulinemia, diabetic retinopathy, alopecia, erectile dysfunction, and tuberous sclerosis.

In some embodiments, the disease is a cancer selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. In certain instances, the disease is a B-Raf V600, such as V600A, V600E, V600G, V600K, V600M or V600R mutant-mediated disease. In one embodiment, the disease is a V600E mutant mediated disease. In one embodiment, the disease is a cancer, preferably selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In one embodiment, the cancer is melanoma, colorectal cancer, thyroid cancer or lung cancer. In another embodiment, the cancer is papillary thyroid cancer or anaplastic thyroid cancer. In another embodiment, the cancer is hairy cell leukemia.

In another embodiment, the disease or condition is a B-Raf V600 mutant mediated disease selected from the group consisting of melanoma, colorectal cancer, papillary thyroid cancer, anaplastic thyroid cancer, ovarian cancer, non-small-cell lung cancer, gastric cancer, cholangiocarcinoma, Barrett's esophageal cancer, head and neck cancer, hepatocellular carcinoma, Langerhan's cell histiocytosis, gastrointestinal stromal cell tumours, multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester disease, inflammatory and autoimmune disease (such as rheumatoid arthritis), tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenoma, choloangiocarcinoma, B-cell chronic lymphoproliferative disorder, dendritic cell sarcomas, histiocytic sarcomas, and lymphoma.

In some embodiments, the disclosure provides methods for treating any B-Raf protein kinase mediated disease or condition, including any B-Raf mutant kinase mediated disease or condition in an animal subject in need thereof, wherein the method involves administering to the subject an effective amount of any one or more solid, crystalline or polymorphs of Compound I or Compound II as described herein. In certain embodiments, the method involves administering to the subject an effective amount of any one or more solid, crystalline or polymorphs of Compound I or Compound II as described herein in combination with one or more other therapies for the disease or condition.

In some embodiments, the disclosure provides methods for treating any B-Raf V600 mutant protein kinase, such as V600A, V600E, V600G, V600K, V600M or V600R mutant protein kinase mediated disease or condition in an animal subject in need thereof, wherein the method involves administering to the subject an effective amount of any one or more solid, crystalline or polymorphs of Compound I or Compound II as described herein. In certain embodiments, the method involves administering to the subject an effective amount of any one or more solid, crystalline or polymorphs of Compound I or Compound II as described herein in combination with one or more other therapies for the disease or condition.

In some embodiments, the disclosure provides a method for inhibiting a B-Raf V600 mutant protein kinase, such as V600A, V600E, V600G, V600K, V600M or V600R mutant protein kinase. The method includes contacting Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N or Compound I Form O as described herein, or a composition thereof or a pharmaceutically acceptable salt or a solvate thereof with a cell or a B-Raf V600 mutant protein kinase either in vitro or in vivo.

In certain embodiments, the disclosure provides use of Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N or Compound I Form O, or a compound as described herein, or a composition thereof or a pharmaceutically acceptable salt or thereof in the manufacture of a medicament for the treatment of a disease or condition as described herein. In other embodiments, the disclosure provides Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N or Compound I Form O and any of the compounds described herein or a pharmaceutically acceptable salt thereof for use in treating a disease or condition as described herein.

In some embodiments, the disclosure provides a method for suppressing UV induced cell apoptosis. The method includes contacting a cell with Compound I Form A, Compound I Form B, Compound I Form D, Compound I Form E, Compound I Form F, Compound I Form G, Compound I Form H, Compound I Form I, Compound I Form J, Compound I Form K, Compound I Form L, Compound I Form M, Compound II Form N or Compound I Form O as described herein, or a composition thereof or a pharmaceutically acceptable salt thereof prior to subject the cell to UV exposure or radiation.

Combination Therapy

Protein kinase modulators may be usefully combined with another pharmacologically active compound, or with two or more other pharmacologically active compounds, particularly in the treatment of cancer. In one embodiment, the composition includes any one or more solid, crystalline or polymorphs of Compound I or Compound II as described herein along with one or more compounds that are therapeutically effective for the same disease indication, wherein the compounds have a synergistic effect on the disease indication. In one embodiment, the composition includes one or more solid, crystalline or polymorphs of Compound I or Compound II as described herein effective in treating a cancer and one or more other compounds that are effective in treating the same cancer, further wherein the compounds are synergistically effective in treating the cancer.

In some embodiments, the disclosure provides a composition comprising one or more solid, crystalline or polymorphs of Compound I or Compound II as described herein. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); MEK inhibitors (e.g., AS703026, AZD6244 (selumetinib), AZD8330, BIX02188, CI1040 (PD184352), D-87503, GSK1120212 (JTP-74057), PD0325901, PD318088, PD98059, PDEA119 (BAY 869766), TAK-733). Preferably, the method of treating a cancer involves administering to the subject an effective amount of a composition including any one or more solid, crystalline or polymorphs of Compound I or Compound II as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-a, interleukin-2, or erlotinib.

In one embodiment, the disclosure provides methods for treating a disease or condition mediated by B-Raf kinase, including mutations thereof, by administering to the subject an effective amount of a composition including any one or more solid, crystalline or polymorphs of Compound I or Compound II as described herein in combination with one or more other suitable therapies for treating the disease.

In one embodiment, the disclosure provides methods for treating a disease or condition mediated by B-Raf V600 mutant kinases, such as V600A, V600E, V600G, V600K, V600M or V600R mutant kinase, by administering to the subject an effective amount of a composition including one or more solid, crystalline or polymorphs of Compound I or Compound II as described herein in combination with one or more other suitable therapies for treating the disease. In one embodiment, the disclosure provides methods for treating a cancer mediated by B-Raf mutant kinases, such as V600A, V600E, V600G, V600M or V600R mutant by administering to the subject an effective amount of a composition comprising one or more solid, crystalline or polymorphs of Compound I or Compound II as described herein. In one embodiment, the disclosure provides methods for treating a cancer mediated by B-Raf mutant kinases, such as V600A, V600E, V600G, V600K, V600M or V600R mutant by administering to the subject an effective amount of a composition including one or more solid, crystalline or polymorphs of Compound I or Compound II as described herein, such as one or more chemotherapeutic drugs. In one instance, the B-Raf mutant kinase is V600A. In another instance, the B-Raf mutant kinase is V600E. In yet another instance, the B-Raf mutant kinase is V600G. In another instance, the B-Raf mutant kinase is V600K. In another instance, the B-Raf mutant kinase is V600M. In another instance, the B-Raf mutant kinase is V600R.

In one embodiment, the disclosure provides a method of treating a cancer in a subject in need thereof by administering to the subject an effective amount of a composition including any one or more solid, crystalline or polymorphs of Compound I or Compound II as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. X-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In certain aspects, one or more solid, crystalline or polymorphs of Compound I or solid, crystalline or polymorphs of Compound II as described herein can be used for the treatment of melanoma.

In certain aspects, one or more solid, crystalline or polymorphs of Compound I or solid, crystalline or polymorphs of Compound II as described herein can be used for the treatment of thyroid cancer.

In certain aspects, one or more solid, crystalline or polymorphs of Compound I or solid, crystalline or polymorphs of Compound II as described herein can be used for the treatment of papillary thyroid cancer.

In certain aspects, one or more solid, crystalline or polymorphs of Compound I or solid, crystalline or polymorphs of Compound II as described herein can be used for the treatment of anaplastic thyroid cancer.

In certain aspects, one or more solid, crystalline or polymorphs of Compound I or solid, crystalline or polymorphs of Compound II as described herein can be used for the treatment of colorectal cancer.

In certain aspects, one or more solid, crystalline or polymorphs of Compound I or solid, crystalline or polymorphs of Compound II as described herein can be used for the treatment of hairy cell leukemia.

Kit

In another aspect, the disclosure provides kits that include a compound of any of formulas (I) to (In) or a compound as described herein or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the disclosure kit may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

EXAMPLES

A. Experimental Methods

Solubility Estimates

Aliquots of various solvents were added to measured amounts of Compound I with agitation (typically sonication) at ambient temperature until complete dissolution was achieved, as judged by visual observation. Solubilities were calculated based on the total solvent used to give a solution; actual solubilities may be greater because of the volume of solvent portions utilized or a slow rate of dissolution. If dissolution did not occur as determined by visual assessment, the value was reported as "<". If dissolution occurred at the first aliquot the value was reported as ">".

| Term | Definition |
| --- | --- |
| Low solubility | <1 mg/mL |
| Limited solubility | 1-20 mg/mL |
| Intermediate solubility | 20-100 mg/mL |
| Good solubility | 100-200 mg/mL |
| High solubility | >200 mg/mL |

Crash Cool (CC)

Concentrated solutions of Compound I were prepared in various solvents at an elevated temperature and filtered warm typically through a 0.2 µm nylon filter into a warm vial. The vial was capped and immediately placed in a bath of isopropanol and dry ice for crash cooling. If no solids were observed after cooling, the sample was placed in the refrigerator (approximately 2 to 8° C.) or freezer (approximately −25 to −10° C.) in an attempt to facilitate precipitation. Solids were collected by vacuum filtration and analyzed.

Fast Evaporation (FE)

Solutions of Compound I were prepared in various solvents. Once a mixture reached complete dissolution as judged by visual observation, the solution was filtered through a 0.2 µm nylon filter. The solution was allowed to evaporate from an open vial under ambient conditions or under nitrogen gas stream. The designation as fast was based on the relative time to form solids. If the solids were formed in less than one day, then the experiment was designated as "FE". Solutions were allowed to evaporate to dryness unless designated as partial evaporations. The solids were isolated and analyzed.

Milling

Compound I solids were transferred to an agate milling container. An agate milling ball was added to the container, which was then attached to a Retsch mill. The mixture was milled for approximately 1 hour at 30 Hz, solids were scraped from the sides of the milling jar after approximately 15 minutes. The resulting solids were transferred to a clean vial and analyzed.

Relative Humidity (RH) Stressing

Solids of Compound I were placed in an RH chamber of approximately 75% RH containing a saturated aqueous solution of an NaCl with excess salt present. The chamber was sealed and left at ambient temperature or placed in an oven at elevated temperature.

Slow Cool (SC)

Concentrated solutions of Compound I were prepared in various solvents with stirring in an oil bath at elevated temperatures. The temperature of the oil bath was slowly reduced to ambient temperature. Solids were collected by vacuum filtration and analyzed.

Slow Evaporation (SE)

Solutions of Compound I were prepared in various solvents at elevated temperature. Once a mixture reached complete dissolution, as judged by visual observation, the solution was filtered through a 0.2 µm nylon filter. The solution was allowed to evaporate from an open vial at ambient temperature or from a vial that was covered with perforated film until evaporation was complete and the solids were observed to be dry. The designation as fast was based on the relative time to form solids. If the solids were formed at a time period longer than one day, then the experiment was designated as "SE". The solids were isolated and analyzed.

Slurry

Solutions of Compound I were prepared by adding sufficient solids to a given solvent or solvent system at ambient conditions such that undissolved solids were present. The mixture was then agitated in a closed vial at ambient or elevated temperature for an extended period of time. Solids were collected by vacuum filtration and analyzed.

Solvent/Antisolvent (S/AS) Precipitation

Solutions of Compound I were prepared in various solvents and filtered through a 0.2 µm nylon filter. Aliquots of various antisolvents were dispensed with stirring until precipitation occurred. Solids were collected by vacuum filtration and analyzed.

Sonication

Solutions of Compound I were prepared in various solvents and filtered through a 0.2 µm nylon filter. The solution was sonicated for approximately 30 mins. If no solids were present after sonication, the sample was placed in the refrigerator (approximately 2 to 8° C.). Solids were collected by vacuum filtration and analyzed.

Temperature Stress

Solids of Compound I were transferred to a vial, which was then placed uncapped, covered with porous paper and placed inside an oven maintained at approximately 50° C. Solids were then analyzed.

Vapor Diffusion (VD)

Concentrated solutions of Compound I were prepared in various solvents and filtered through a 0.2 μm nylon filter. The filtered solution was dispensed into a vial, which was then placed, uncapped inside a jar containing antisolvent. The jar was capped to allow vapor diffusion to occur. Solids were collected by vacuum filtration or by decanting the solvent and allowing the solids to air dry at ambient conditions prior to analysis.

Vapor Stress (VS)

Solids of Compound I were transferred to a vial, which was then placed uncapped inside a jar containing solvent. The jar was capped to allow vapor stressing to occur. Vapor stressing experiments were conducted at ambient temperature. Solids were then analyzed.

Instrumental Techniques

Differential Scanning Calorimetry (DSC)

DSC was performed using a TA Instruments Q2000 and 2920 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min". The following table summarizes the abbreviations used in each image for pan configurations:

| Abbreviation (in comments) | Meaning |
| --- | --- |
| T0C | Tzero crimped pan |
| HS | Lid hermetically sealed |
| HSLP | Lid hermetically sealed and perforated with a laser pinhole |
| C | Lid crimped |
| NC | Lid not crimped |

Proton Solution Nuclear Magnetic Resonance Spectroscopy ($^1$H NMR)

Proton solution NMR spectra were acquired at Spectral Data Solutions (subcontractor) at ambient temperature on a Varian $^{UNITY}$INOVA-400 spectrometer ($^1$H Larmor Frequency=399.8 MHz). The samples were dissolved in NMR-grade DMSO-$d_6$. Each $^1$H NMR spectrum represents 40 co-added transients collected with a 6 μsec pulse and a relaxation delay time of 5 seconds. The free induction decay (FID) was exponentially multiplied with a 0.2 Hz Lorentzian line broadening factor to improve the signal-to-noise ratio.

Thermogravimetric Analysis (TGA)

TG analyses were performed using a TA Instruments 2950 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram in the Data section of this report. The method code on the thermogram is an abbreviation for the start and end temperature as well as the heating rate; e.g., 25-350-10 means "from 25° C. to 350° C., at 10° C./min".

X-Ray Powder Diffraction (XRPD)

X-ray powder diffraction patterns were collected using a PANalytical X'Pert PRO MPD diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated parallel to the diffraction vector to optimize orientation statistics. A beam-stop, short antiscatter extension, antiscatter knife edge, and helium purge were used to minimize the background generated by air scattering. Soller slits were used for the incident and diffracted beams to minimize axial divergence. Diffraction patterns were collected using a scanning position-sensitive detector (X'Celerator) located 240 mm from the specimen. Prior to the analysis a silicon specimen (NIST standard reference material 640d) was analyzed to verify the position of the silicon 111 peak.

The data presented contain X-ray diffraction patterns with tables with peak lists. The range of data collected is instrument dependent. Under most circumstances, peaks within the range of up to about 30° 2θ were selected. Rounding algorithms were used to round each peak to the nearest 0.1° or 0.01° 2θ, depending upon the instrument used to collect the data and/or the inherent peak resolution. The location of the peaks along the x-axis (° 2θ) in both the figures and the tables were determined using proprietary software (TRIADS, version 2) and rounded to one or two significant figures after the decimal point based upon the above criteria. Peak position variabilities are given to within ±0.2° 2θ based upon recommendations outlined in the USP discussion of variability in X-ray powder diffraction (United States Pharmacopeia, USP 37, NF 32, through S2 <941>, 503, Dec. 1, 2014). The accuracy and precision associated with any particular measurement reported herein has not been determined. Moreover, third party measurements on independently prepared samples on different instruments may lead to variability which is greater than ±0.2° 2θ. For d-space listings, the wavelength used to calculate d-spacings was 1.5405929 Å, the Cu—K$_{α1}$ wavelength (Phys. Rev. A56(6) 4554-4568 (1997). Variability associated with d-spacing estimates was calculated from the USP recommendation, at each d-spacing, and provided in the respective data tables.

Per USP guidelines, variable hydrates and solvates may display peak variances greater than 0.2° 2θ and therefore peak variances of 0.2° 2θ are not applicable to these materials.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

Example 1: Preparation of Compound I Form A

A glass vial was charged with 80.2 mg of Compound I Form B and 3.0 mL of dichloromethane. The sample was heated to approximately 30° C. The resulting solution was filtered through a 0.2 μm nylon filter into a glass vial. The sample was placed into a larger vessel containing approximately 10 mL of acetone. The large container was sealed and left at ambient temperature. After 11 days the solids were harvested by vacuum filtration and air dried. It was characterized by XRPD. Major peaks are listed in Table 1.

Example 2: Preparation of Compound I Form B

A glass vial was charged with 153.8 mg of Compound I Form B (+trace Compound I Material C, it is a mixture of Forms) and 5.0 mL of a 75:25 (v:v) ethanol/water solvent system. The sample was heated to approximately 65° C. resulting in a clear solution. The solution was filtered through a 0.2 μm nylon filter into a glass vial. The sample was sonicated for approximately 20 minutes in an ambient temperature sonication bath resulting in nucleation. The solids were harvested, by vacuum filtration, and air dried. It was characterized by XRPD. Major peaks are listed in Table 2.

Alternatively, under identical conditions as discussed in the above paragraph, using Compound I (as synthesized according to the synthetic scheme discussed in this application) as the starting material, provides pure Compound I Form B.

Example 3: Preparation of Compound I Material C

Traces of Compound I Material C was observed, as a mixture with Form B, in the above-mentioned starting material.

Example 4: Preparation of Compound I Form D

A glass vial was charged with 98.4 mg of Compound I Form B and 1.0 mL of tetrahydrofuran and sonicated. The sample was then filtered through a 0.2 μm nylon filter into a glass vial. The sample was evaporated under nitrogen resulting in white solids. It was characterized by XRPD. Major peaks are listed in Table 3.

Example 5: Preparation of Compound I Form E

A glass vial was charged with 99.5 mg of Compound I Form B and 1.0 mL of dioxane and agitated. The sample was then filtered through a 0.2 μm nylon filter into a glass vial. The sample was evaporated under nitrogen for approximately 3 minutes until a paste was formed. The material was then dried at ambient for approximately 10 minutes. It was characterized by XRPD. Major peaks are listed in Table 4.

Example 6: Preparation of Compound I Form F

A glass vial was charged with 98.3 mg of Compound I Form B and 0.7 mL of dioxane and stirred. The sample was then filtered through a 0.2 μm nylon filter into a glass vial. The vial opening was covered with Parafilm® and pierced 5 to 6 times. The sample was left at ambient to evaporate to dryness. It was characterized by XRPD. Major peaks are listed in Table 5.

Example 7: Preparation of Compound I Form G

A glass vial was charged with 78.8 mg of Compound I Form B and 7.0 mL of ethyl acetate. The sample was heated to approximately 70° C. with stirring until few solids remained. The sample was filtered through a 0.2 μm nylon filter into a glass vial, stirring continued, and cooled from 70° to 24° C. over the course of a day. The sample was refrigerated overnight and the solids were harvested, by vacuum filtration, and air dried. It was characterized by XRPD. Major peaks are listed in Table 6.

Example 8: Preparation of Compound I Form H

A glass vial was charged with 102.5 mg of Compound I Form B (+trace Compound I Material C) and 6.0 mL of acetonitrile. The sample was heated to approximately 80° C. with stirring in an oil bath. The sample was filtered through a 0.2 μm nylon filter into a glass vial, stirring continued, and cooled in the oil bath from 80° C. to 24° C. overnight. Solids were harvested by vacuum filtration and air dried. It was characterized by XRPD. Major peaks are listed in Table 7.

Example 9: Preparation of Compound I Form I

A glass vial was charged with 99.0 mg of Compound I Form B (+trace Compound I Material C) and 1.0 mL of tetrahydrofuran. The sample was briefly agitated and filtered through a 0.2 μm nylon filter into a glass vial and stirred. To the stirring solution 5.0 mL of methyl tert-butyl ether was added and allowed to continue agitation for approximately 4 hours; fines were observed after approximately 15 minutes. The sample was refrigerated (2 to 8° C.) overnight prior to harvesting by vacuum filtration and air dried. It was characterized by XRPD. Major peaks are listed in Table 8.

Example 10: Preparation of Compound I Form J

A glass vial was charged with 177.9 mg of Compound I Form B and 1.6 mL of dimethylformamide. The sample was heated to approximately 40° C. The resulting solution was filtered through a 0.2 μm nylon filter into a glass vial. The sample was refrigerated (2 to 8° C.) for approximately 10 days with intermittent removal and reduction of volume at ambient conditions or under nitrogen. The solution was evaporated to dryness under nitrogen. It was characterized by XRPD. Major peaks are listed in Table 10.

Example 11: Preparation of Compound I Form K (+Compound I Form H)

A glass vial was charged with 45.9 mg of Compound I Form G. The sample was slurried for 3 days, at ambient temperature, prior to harvesting by vacuum filtration and air drying. The solids were determined to be a mixture with Form H. It was characterized by XRPD. Major peaks are listed in Table 11.

Example 12: Preparation of Compound I Form L

A glass vial was charged with 104.6 mg of Compound I Form B and 6.0 mL of acetonitrile. The sample was heated to approximately 80° C. with stirring until clear. The sample was filtered through a 0.2 μm nylon filter into a glass vial and placed into an isopropyl alcohol ice bath resulting in solid formation. The sample was warmed to ambient resulting in reduction of solids. The sample was transferred to a cold room (2 to 8° C.) and stirred for 1 day. The solids were then harvest by vacuum filtration and air dried. It was characterized by XRPD. Major peaks are listed in Table 12.

Example 13: Preparation of Compound I Form M

A glass vial was charged with 204.2 mg of Compound I Form B and 1.0 mL of dimethylsulfoxide. The sample was heated to approximately 60° C. The resulting solution was filtered through a 0.2 μm nylon filter into a glass vial. The sample was refrigerated (2 to 8° C.) for approximately 15 days with intermittent removal and reduction of volume at ambient conditions or under nitrogen until crystallization was observed. It was characterized by XRPD. Major peaks are listed in Table 13.

Example 14: Preparation of Compound II Form N

A sample of the S-enantiomer of Compound I was designated Compound II Form N based on XRPD analysis. It was characterized by XRPD. Major peaks are listed in Table 14.

Example 15: Preparation of Compound I Form O

A glass vial was charged with 136.5 mg of Compound I which is a mixture of Form B and Form O and 15 mL of a 98:2 (v:v) water/ethanol solvent system. The sample was slurried for 8 days, at ambient temperature, prior to harvesting by vacuum filtration. It was characterized by XRPD. Major peaks are listed in Table 14.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the disclosure using one of the terms, the disclosure also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described disclosure.

Thus, additional embodiments are within the scope of the disclosure and within the following claims.

What is claimed is:
1. A crystalline form of Compound I:

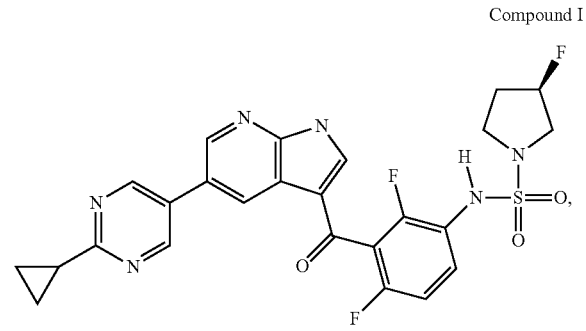 [SMILES: O=C(c1c(F)ccc(NS(=O)(=O)N2CC[C@@H](F)C2)c1F)c1c[nH]c2ncc(-c3cnc(C4CC4)nc3)cc12]

Compound I which is Compound I Form B, characterized by an X-ray powder diffractogram comprising peaks (±0.2°) at 10.4, 16.0, and 18.0 °2θ as determined on a diffractometer using Cu—Kα radiation.

2. A crystalline form of Compound I:

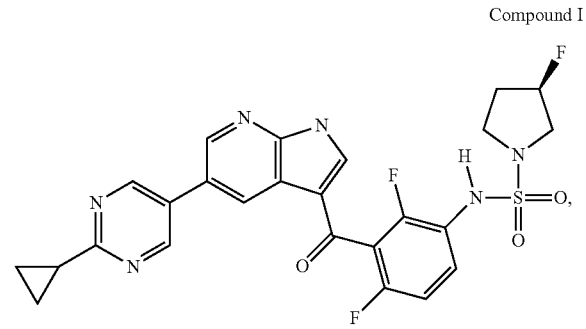 [SMILES: O=C(c1c(F)ccc(NS(=O)(=O)N2CC[C@@H](F)C2)c1F)c1c[nH]c2ncc(-c3cnc(C4CC4)nc3)cc12]

Compound I which is Compound I Form H, characterized by an X-ray powder diffractogram comprising peaks (±0.2°) at 8.5, 17.0, and 23.7 °2θ as determined on a diffractometer using Cu—Kα radiation.

3. A composition comprising the crystalline form of Compound I according to claim 1.

4. A composition comprising at least about 50% w/w of the crystalline form of Compound I according to claim 1.

5. A pharmaceutical composition comprising the crystalline form of Compound I according to claim 1 and a pharmaceutically acceptable excipient.

* * * * *